United States Patent [19]

Koda et al.

[11] Patent Number: 5,344,845
[45] Date of Patent: Sep. 6, 1994

[54] COMPOUND AND USE OF THE SAME AS MEDICINE

[75] Inventors: Akihide Koda, Gifu; Koji Waragai, Ibaraki; Yutaka Ono, Ibaraki; Hideyuki Ozawa, Ibaraki; Hideki Kawamura, Ibaraki; Masao Maruno, Ibaraki; Takeshi Wakamatsu, Ibaraki, all of Japan

[73] Assignee: Tsumura & Co., Tokyo, Japan

[21] Appl. No.: 938,170

[22] PCT Filed: Apr. 10, 1992

[86] PCT No.: PCT/JP92/00451
§ 371 Date: Dec. 4, 1992
§ 102(e) Date: Dec. 4, 1992

[87] PCT Pub. No.: WO92/18463
PCT Pub. Date: Oct. 29, 1992

[30] Foreign Application Priority Data

Apr. 10, 1991 [JP] Japan .................. 3-103558
Feb. 27, 1992 [JP] Japan .................. 4-75678

[51] Int. Cl.$^5$ ............... A61K 31/165; A61K 31/495; C07C 103/82; C07D 213/75

[52] U.S. Cl. .................. 514/614; 564/168; 549/491; 544/391; 544/398; 546/216; 546/236; 560/104; 514/485; 514/486; 514/683; 514/317; 514/330; 514/255; 514/464

[58] Field of Search .......... 564/168; 514/617

[56] References Cited

U.S. PATENT DOCUMENTS 4,673,684  6/1987  Wakabayashi et al. ........... 514/327

FOREIGN PATENT DOCUMENTS 55-130949  10/1980  Japan .
60-214766  10/1985  Japan .
3-86853    4/1991   Japan .

OTHER PUBLICATIONS

Johnson et al., Journal of the American Chemical Society, 92(19) (1971), 4880–4883.
Eckhardt et al., Chemical Abstracts 89(3) 23, 2924, 1978.

*Primary Examiner*—Mukund J. Shah
*Assistant Examiner*—Matthew V. Grumbling
*Attorney, Agent, or Firm*—Nixon & Vanderhye

[57] ABSTRACT

Disclosed herein is a specific cinnamic acid derivative such as methyl 4-(4-acetoxy-3-methoxycinnamanide)-1-cyclohexanecarboxylate, or a pharmaceutically acceptable salt thereof. These compounds are useful as IV-type allergic reaction-suppressive drugs.

7 Claims, No Drawings

COMPOUND AND USE OF THE SAME AS MEDICINE

TECHNICAL FIELD

The present invention relates to a novel compound which has IV-type allergic reaction-suppressive function and which is useful as a medicine such as IV-type allergy suppressive drug.

BACKGROUND ART

It has been reported that IV-type allergic reaction is greatly responsible for the pathopoiesis of refractory diseases such as refractory asthma, chronic hepatitis and nephrotic syndrome. To cure these refractory diseases, immunosuppressive agents, a typical example of which is asteroid drug, are used. However, the use of the immunosuppressive agents is limited, inevitably because of their strong side effects.

DISCLOSURE OF INVENTION

Therefore it has been demanded that a IV-type allergic reaction-suppressive agent be developed in place of the immunosuppressive agents hitherto known.

In order to meet the demand described above, the inventors hereof have been making research and study, in search for a substance which works against IV-type allergic reaction in its effector phase. They successfully synthesized the compounds represented by the following formulas I, II, III, IV and V, and examined these compounds for their pharmacological activities to find that these compounds have desired IV-type allergic reaction-suppressive function, thus completing the present invention.

The present invention provides the compounds represented by the formulas I, II, III, IV and V or pharmaceutically acceptable salts thereof, and IV-type allergic reaction-suppressive agents containing, as effective components, the compounds represented by the formula I, II, III, IV and V, or pharmaceutically acceptable salts thereof.

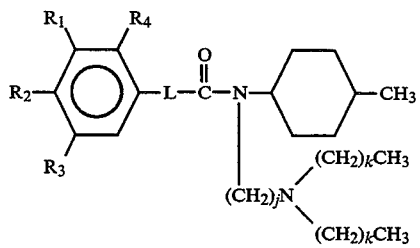

(I)

where L represents —(CH=CH)$_k$— or —(CH$_2$)$_k$—; j represents an integer of 1 to 6; k represents represents an integer of 0 to 5; R$_1$, R$_2$, R$_3$ and R$_4$ are either identical or different, and each represents a hydrogen atom, an amino group, an acylamino group (preferably, one in which the acyl moiety has 1 to 3 carbon atoms), a dialkylamino group in which each alkyl moiety has 1 to 5 carbon atoms, a halogen atom, a hydroxyl group, an acetoxy group, an alkoxy group having 1 to 3 carbon atoms, a trifluoromethyl group, a nitro group, tetrahydropyranyloxy group, or a benzyloxy group; and R$_1$ and R$_2$ may combine together to form a methylenedioxy group.

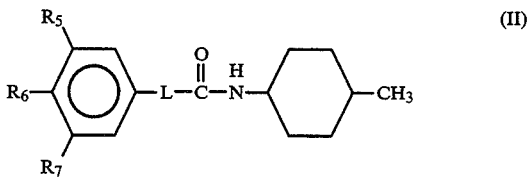

(II)

where L represents —(CH=CH)$_k$— or —(CH$_2$)$_k$—; each k represents an integer of 0 to 5; R$_5$, R$_6$ and R$_7$ are either identical or different, and each represents a hydrogen atom, a hydroxyl group, an acetoxy group, an amino acid ester group in which the amino moiety may be protected by a protective group, an alkoxy group having 1 to 3 carbon atoms, or —O—(CH$_2$)$_j$—Y$_1$; R$_5$ and R$_6$ may combine together to form a methylenedioxy group. j represents an integer of 1 to 6, and Y$_1$ is a halogen atom, an amino group, an amino group substituted with 1 or 2 thioethanol groups, an amino group substituted with 1 or 2 allyl groups, a monoalkylamino group having 1 to 10 carbon atoms, a dialylamino group in which each alkyl moiety has 1 to 10 carbon atoms, an imidazole group substituted with 1 to 3 substituent groups (e.g., a nitro group, a cyano group, a phenyl group, an alkoxy group having 1 to 3 carbon atoms, a halogen atom, or an alkyl group having 1 to 3 carbon atoms), a benzimidazole group substituted with 1 to 3 substituent groups (e.g., a nitro group, a cyano group, a phenyl group, an alkoxy group having 1 to 3 carbon atoms, a halogen atom, or an alkyl group having 1 to 3 carbon atoms), a diazole group, a triazole group, a tetrazole group, a piperidine group, a piperidinopiperidine group, an isonipecotic acid group or an ester thereof with an alkyl group having 1 to 5 carbon atoms, a thiazolidine group, a pyrrolidine group, a morpholine group, a 4-methylpiperazine group, a carboxyl group (—COOH), a carboxylic acid alkylester group in which the alkyl moiety has 1 to 5 carbon atoms (—COO—C$_1$ to C$_5$ alkyl) or a carboxamide group.

In the formula (II), the amino acid ester groups represented by R$_5$, R$_6$, and/or R$_7$ are groups formed by removing hydrogen from the carboxyl group of an amino acid. Examples of the amino acid are glycine, alanine, leucine, and proline. Examples of the protective group for the amino group of the amino acid ester group are acetyl group, benzyloxycarbonyl group, and t-butoxycarbonyl group.

Also in the formula (II), the carboxylic carboxamide group represented by Y$_1$ is a group which is formed by reaction of a carboxylic acid group (—COOH) with a primary or secondary amine, HN(R')R", and which can be represented by —COON(R')R", where R' and R" are either identical or different, and each represents, e.g., a hydrogen atom, a piperidinopiperidine group, or 4-methylpiperazine group.

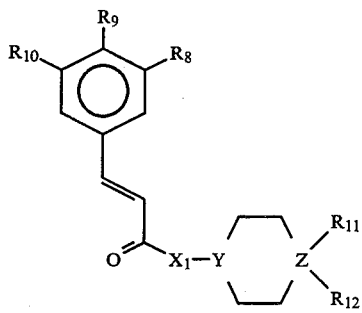

(III)

where $X_1$ is an oxygen atom, $>NH$, $>N$-alkyl group (e.g., one in which the alkyl moiety has 1 to 5 carbon atoms), or $-NHCH_2-$; Y is a nitrogen atom, CH, or C—OH; Z is a nitrogen atom or a carbon atom; $R_8$, $R_9$ and $R_{10}$ are either identical or different, and each represents a hydrogen atom, a hydroxyl group, an acetoxy group, an alkoxy group having 1 to 3 carbon atoms, or $-O-(CH_2)_j-Y_2$; $R_{11}$ and $R_{12}$ are either identical or different, and each represents a hydrogen atom, an alkyl group having 1 to 6 carbon atoms, —COOH, —COO-alkyl group, or —COO-allyl group if Z is a carbon atom, or $R_{11}$ and $R_{12}$ represents one hydrogen atom, one alkyl group having 1 to 6 carbon atoms, one —COOH group, one —COO-alkyl group, or one —COO-allyl group if Z is a nitrogen atom; j is an integer of 1 to 6; and $Y_2$ is a chlorine atom, a dialkylamino group in which each alkyl moiety has 1 to 6 carbon atoms, an imidazole group, a piperidine group, a pyrrolidine group, a morpholine group, or a 4-methylpiperazine group.

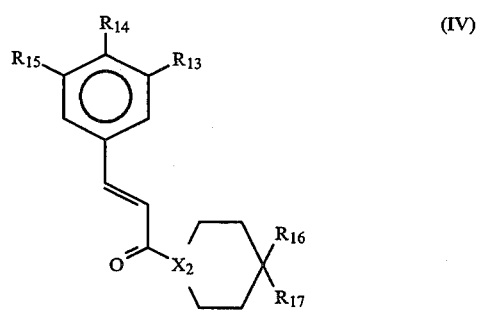

(IV)

where $X_2$ is CH or a nitrogen atom; $R_{13}$, $R_{14}$ and $R_{15}$ are either identical or different, and each represents a hydrogen atom, a hydroxyl group, a acetoxy group, an alkoxy group having 1 to 3 carbon atoms, or an —O—allyl group; and $R_{16}$ and $R_{17}$ are either identical or different, and each represents a hydrogen atom, an alkyl group having 1 to 6 carbon atoms, a carboxylic acid group (—COOH), a carboxylic acid alkylester group in which the alkyl group has 1 to 5 carbon atoms (—COO—$C_1$ to C5-alkyl), or a carboxylic acid allylester group (—COO-allyl).

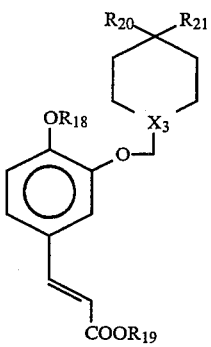

(V)

where $X_3$ is CH or C—OH; $R_{18}$ is a hydrogen atom or an alkyl group having 1 to 6 carbon atoms; $R_{19}$ is a hydrogen atom, an alkyl group having 1 to 6 carbon atoms, or an allyl group; $R_{20}$ and $R_{21}$ are either identical or different, and each represents a hydrogen atom, an alkyl group having 1 to 6 carbon atoms, a carboxylic acid group (—COOH), a carboxylic acid alkylester group in which the alkyl group has 1 to 5 carbon atoms (—COO—$C_1$ to C5-alkyl), or a carboxylic acid allylester group (—COO—allyl).

Hereinafter, the compounds represented by the formulas I, II, III, IV, and V shall be referred to as the "compounds of the present invention."

BEST MODE OF CARRYING OUT THE INVENTION

The compounds of the present invention can be obtained by performing the following reactions 1 to 17, in an appropriate combination, on the compounds known hitherto:

1. Acetalization
2. Alkylation
3. Reduction
4. Esterification and amidation
5. Halogenation
6. Conversion into azide
7. Hydrolysis
8. Reductive amination
9. Vinylation
10. Aldol condensation
11. Olefination
12. Hydroboration
13. Conversion into imine or oxime
14. Iodolactonization
15. Knoevenagel condensation
16. Amination
17. Conversion into non-toxic salts The reactions mentioned above may be carried out in ordinary manners. These reactions will be each explained below.

1. Acetalization is achieved by reacting a carbonyl compound with an alcohol. In this case, the alcohol ranges from lower alcohol having 1 to 6 carbon atoms, to one having two or more hydroxyl groups, and is used in an amount equal to or greater than the equivalent amount of the carbonyl compound.

As a solvent, use may be made of a hydrocarbon such as benzene, toluene and xylene, ether, dimethylformamide (DMF), or the like. The lower alcohol involving in the reaction with the carbonyl compound may be used as a solvent. A temperature of $-10°$ C. to $150°$ C. is sufficient as the reaction temperature. Preferably, the temperature is $80°$ C. to $110°$ C.

During the reaction, use can be made, if necessary, of an acid catalyst such as hydrochloric acid, sulfuric acid, calcium chloride, ammonium chloride, p-toluic acid, hydrogen bromide, boron trifluoride, a carboxylic acid, selenium oxide, phosphoric acid or the like, or a dehydrating agent such as ion-exchange resin, molecular sieves, aluminum chloride, a polymer complex or molecular sieves. Also, during the reaction, a Dean-Stark trap can be used to remove the water formed, out of the system.

2. Alkylation is accomplished by using a base such as sodium carbonate, potassium carbonate, sodium hydride, lithium diisopropylamide (LDA), sodium hexamethyldisilazide, sodium hydroxide, or the like, in an amount equal to or greater than the equivalent amount of the substrate used, thereby generating anions, and by reacting the anions with one equivalent amount or more of alkyl halide or allyl halide.

As a solvent, use may be made of at least one selected from a hydrocarbon, methylene chloride, chloroform, carbon tetrachloride, ether, tetrahydrofuran (THF), DMF, dimethylsulfoxide (DMSO), a lower alcohol, and water. The reaction may be performed at a temperature of −78° C. to 150° C., in accordance with the reagent used.

3. Reduction may be achieved by: (i) a reduction by an alkali metal such as sodium or lithium, an alkaline earth metal such as calcium or magnesium, a metal such as aluminum, zinc, iron or copper, or a salt of any one of these metals is used as a reducing agent; (ii) a reduction by a metal hydride such as diisobutylaluminum hydride, organic tin hydride or hydrosilane, a metal hydrogen complex compound such as lithium aluminum hydride or sodium borohydride, or a complex thereof with borane or diborane; or (iii) a reduction in which a metal, such as nickel, cobalt, palladium, rhodium, copper or platinum, or an oxide, chloride or salt of any of these metals is used as a catalyst.

In the reduction methods (i), (ii), and (iii), the reaction may be effected with the reducing agent in an amount equal to or greater than an equivalent amount of the substrate, or the metal or the oxide, chloride or salt thereof in a catalytic amount, in at least one solvent selected from water and an organic solvent such as a lower alcohol, acetic acid, hydrochloric acid, ammonia, a primary, secondary or tertiary amine, a hydrocarbon, methylene chloride, chloroform, ether, and THF, under air an inert gas or hydrogen gas, at an atmospheric pressure or an elevated pressure, and at a temperature of −78° C. to 150° C. in accordance with the reagent used.

In the reduction method (iii), a salt of formic acid, for example, can be used as a hydrogen source.

4. Esterification and amidation may be performed by reacting sulfonic acid, carboxylic acid, or an acid chloride or acid anhydride thereof with a compound having a hydroxyl group, such as a phenol or an alcoholic compound, or having primary or secondary amine, at a temperature of −78° C. to 150° C., using, as a solvent, a hydrocarbon, methylene chloride, chloroform, carbon tetrachloride, ether, tetrahydrofuran (THF), DMF, dimethylsulfoxide (DMSO), a lower alcohol, water, or an amine such as pyridine.

If necessary, use can be made of a condensating agent such as diethyl chlorophosphate, diethyl cyanophosphate or dicyclohexylcarbodiimide, and a catalytic amount of dimethylaminopyridine. Also, if necessary, use can be made of the dehydrating agent described above, the dehydrating apparatus, an acid catalyst, and a deacidifyer such as a tertiary amine.

5. Halogenation may be accomplished by reacting a sulfonic acid ester with a halogen or a salt thereof at −78° C. to 150° C. in the solvent specified above.

6. Conversion into azide may be achieved by reacting an alkyl halide or a sulfonic acid ester with a salt such as hydrogen azide or sodium azide, or by reacting an alcoholic compound with a salt such as hydrogen azide or sodium azide, using an azo compound such as diethyl azodicarboxylate or using triphenylphosphine or the like.

If necessary, 15-crown-5-ether can be used together.

In this case, the solvent specified above is used, and the reaction temperature is −78° C. to 150° C., preferably 0° C. to 50° C.

7. Hydrolysis may be performed by reacting an acetal, a lactone or an ester with an acid such as hydrochloric acid, sulfuric acid or p-toluenesulfonic acid, an alkali such as sodium hydroxide or potassium carbonate, or boron halide such as boron tribromide, in the above-mentioned solvent at a temperature of −78° C. to 150° C.

8. Reductive amination may be effected by reacting a carbonyl compound with a primary amine, followed by a reaction with a metal hydrogen complex compound such as sodium cyanoborohydride or the like.

Lower alcohols or the ordinary solvents specified above may be used singly or in combination as a solvent. The reaction temperature is −78° C. to 150° C., preferably 0° C. to 30° C.

The reaction will proceed readily if the primary amine or the metal hydrogen complex compound is used in an amount equal to or greater than an equivalent amount of the substrate and is neutralized with an acid such as hydrochloric acid when the reaction is effected.

9. Vinylation may be accomplished by reacting a carbonyl compound with a sulfonic acid such as trifluorosulfonic acid, an anhydride or acid chloride thereof, in air or inert gas and in, if necessary, a sealed reaction system, in the presence of a tertiary amine, thereby forming enolsulfonate, which is then reacted with a vinyl ether compound, using a complex of a metal such as palladium as a catalyst.

The ordinary solvents specified above may be used singly or in combination as a solvent. The reaction temperature is −78° C. to 150° C., preferably 50° C. to 80° C.

10. Aldol condensation may be performed by reacting carbonyl compounds with one another, in the presence of a base such as sodium hydride, sodium hydroxide, potassium t-butoxide or sodium methoxide.

Lower alcohols, and the ordinary solvents specified above may be used singly or in combination as a solvent. The reaction temperature is −78° C. to 150° C., depending on the reagent used.

11. Olefination may be achieved by reacting a carbonyl compound with a ylide of, e.g., phosphorus or sulfur, an organosilicon compound or an alkyl dihalide at −78° C. to 150° C., in one of the ordinary solvents specified above or a mixture of thereof.

In this case, a metal such as zinc or a Lewis acid such as titanium tetrachloride may be used as a catalyst. If necessary, a base such as potassium carbonate, LDA or sodium hydride may be used. Further, if necessary, 18-crown-6-ether or a lithium salt may be used together.

12. Hydroboration may be achieved by reacting an olefin with borane, diborane or a complex thereof in one of the above-mentioned ordinary solvents or a mixture thereof at −78° C. to 150° C., followed by oxidization with a peroxide such as hydrogen peroxide in an alkali such as sodium hydride, thereby introducing a hydroxyl group.

13. Conversion into imine or oxime may be effected by reacting a carbonyl compound with a primary amine, a hydroxyamine or a salt thereof, in one of the abovementioned ordinary solvents or a mixture of the ordinary solvents.

14. Iodolactonization may be accomplished by adding, if necessary, a salt such as potassium iodide or the like used as a catalyst, to a compound having olefin or carboxylic acid, and then reacting this compound with with iodine. The reaction is performed in one of the abovementioned ordinary solvents or a mixture thereof at −78° C. to 150° C.

15. Knoevenagel condensation may be achieved by reacting a carbonyl compound with an equivalent amount or more of a reactive methylene compound such as malonic acid, cyanoacetic acid or an ester thereof, in one of the above-specified ordinary solvents, a mixture thereof or a tertiary amine at 0° C. to 150° C. The reaction can be performed by using, if necessary, a catalytic amount of a primary or secondary amine, or the dehydrating agent specified above, or the apparatus for removing the water formed.

16. Amination may be performed by reacting an alkyl halide with ammonia or a primary or secondary amine such as dimethylamine or piperidine. If necessary, use may be made of a base such as sodium hydride.

The ordinary solvents specified above or water may be used singly or in combination as a solvent. The reaction temperature may be 0° C. to 150° C.

17. Conversion into non-toxic salts can be accomplished by reacting a compound having amine, alcohol, phenol or carboxylic acid, with an amino acid, potassium hydride, hydrogen chloride, hydrogen sulfide, phosphoric acid, maleic acid, fumaric acid, succinic acid, tartaric acid, salicylic acis, p-toluenesulfonic acid, citric acid, sodium methoxide, or a primary, secondary or tertiary amine such as ammonium, trishydroxymethylaminomethane or N-methyldiethanolamine, in one of the ordinary solvents specified above, water, an alcohol, or a mixture thereof, at a temperature of 0° C. to 150° C.

In this case, the salt formed must be pharmaceutically acceptable.

One skilled in the art will understand the application of these reactions and the details thereof, from the Examples of the invention which shall be described later.

Next, the experiments will be described to show that the compounds of the present invention has IV-type allergic reaction-suppressive function.

EXPERIMENTS

Procedure of the Experiments

Reaction in the sole of the foot, caused by sheep's red blood cells (hereinafter referred to as "SRBC") was used as model of IV-type allergic reaction. To be specific, SRBC was adjusted to $2.5 \times 10^6$/ml with physiological saline, and 0.2 ml thereof was injected into the tail veins of BALB/c mice (7-week old, male) and thus sensitized. Four days later, SRBC of the same lot was adjusted to $4 \times 10^9$/ml, and 0.025 ml thereof was injected into the skin of the right-foot soles, thereby provoking the reaction. The volume of the right-foot sole of each mouse, measured prior to the provocation of the reaction, was subtracted from the volume of the right-foot sole measured 24 hours after the provocation of the reaction, thus obtaining a difference. From this difference, the degree of the IV-type allergic reaction was determined.

The compounds obtained in the Examples were dissolved in purified water or distilled water, and each was orally administered to a group of mice twice, first immediately before the provocation of the reaction, and then 16 hours thereafter.

The administered amount of the compounds obtained in the Examples was $3.37 \times 10^{-4}$ mol/kg in Experiments 1 to 8, and $3.46 \times 10^{-4}$ mol/kg in Experiments 9 to 21.

The results are shown in the following tables, in terms of suppression rate (%) in comparison with a control.

TABLE 1

| | Supression Rate (%) | Number of Mice |
|---|---|---|
| Control | | 8 |
| Sodium salt obtained in Example 65 | 28.2 | 8 |
| Sodium salt obtained in Example 68 | 46.4 | 8 |
| Sodium salt obtained in Example 60 | 41.7 | 8 |

TABLE 2

| | Supression Rate (%) | Number of Mice |
|---|---|---|
| Control | | 8 |
| Sodium salt obtained in Example 54 | 39.6 | 8 |
| Sodium salt obtained in Example 65 | 34.7 | 8 |
| Sodium salt obtained in Example 68 | 51.8 | 8 |
| Sodium salt obtained in Example 60 | 35.9 | 8 |

TABLE 3

| | Supression Rate (%) | Number of Mice |
|---|---|---|
| Control | | 7 |
| Sodium salt obtained in Example 62 | 40.0 | 7 |
| Sodium salt obtained in Example 56 | 20.7 | 8 |

TABLE 4

| | Supression Rate (%) | Number of Mice |
|---|---|---|
| Control | | 7 |
| Sodium salt obtained in Example 62 | 46.2 | 7 |

TABLE 5

| | Supression Rate (%) | Number of Mice |
|---|---|---|
| Control | | 8 |
| Sodium salt obtained in Example 40 | 31.8 | 8 |
| Sodium salt obtained in Example 49 | 50.7 | 8 |

TABLE 6

|  | Supression Rate (%) | Number of Mice |
|---|---|---|
| Control |  | 8 |
| Sodium salt obtained in Example 64 | 41.6 | 8 |
| Sodium salt obtained in Example 52 | 22.2 | 8 |

TABLE 7

|  | Supression Rate (%) | Number of Mice |
|---|---|---|
| Control |  | 10 |
| Sodium salt obtained in Example 105 | 69.6 | 9 |
| Sodium salt obtained in Example 131 | 67.5 | 8 |

TABLE 8

|  | Supression Rate (%) | Number of Mice |
|---|---|---|
| Control |  | 9 |
| Sodium salt obtained in Example 105 | 36.2 | 9 |

TABLE 9

|  | Suppression Rate (%) | Number of Mice |
|---|---|---|
| Control |  | 8 |
| Hydrochloride salt obtained in Example 107 | 77.8 | 7 |
| Hydrochloride salt obtained in Example 139 | 60.0 | 8 |

TABLE 10

|  | Suppression Rate (%) | Number of Mice |
|---|---|---|
| Control |  | 8 |
| Hydrochloride salt obtained in Example 112 | 45.3 | 8 |
| Hydrochloride salt obtained in Example 80 | 47.6 | 8 |
| Hydrochloride salt obtained in Example 108 | 22.4 | 8 |
| Hydrochloride salt obtained in Example 157 | 69.6 | 8 |

TABLE 11

|  | Suppression Rate (%) | Number of Mice |
|---|---|---|
| Control |  | 8 |
| Hydrochloride salt obtained in Example 79 | 28.6 | 8 |
| Hydrochloride salt obtained in Example 112 | 74.9 | 8 |
| Hydrochloride salt obtained in Example 80 | 60.9 | 8 |
| Hydrochloride salt obtained in Example 108 | 77.8 | 7 |
| Hydrochloride salt obtained in Example 157 | 72.5 | 8 |

TABLE 12

|  | Suppression Rate (%) | Number of Mice |
|---|---|---|
| Control |  | 8 |
| Hydrochloride salt obtained in Example 107 | 65.3 | 8 |
| Hydrochloride salt obtained in Example 139 | 82.9 | 7 |
| Hydrochloride salt obtained in Example 112 | 80.3 | 8 |
| Hydrochloride salt obtained in Example 80 | 82.4 | 7 |
| Hydrochloride salt obtained in Example 108 | 68.7 | 7 |

TABLE 13

|  | Suppression Rate (%) | Number of Mice |
|---|---|---|
| Control |  | 7 |
| Hydrochloride salt obtained in Example 81 | 81.9 | 5 |

TABLE 14

|  | Suppression Rate (%) | Number of Mice |
|---|---|---|
| Control |  | 9 |
| Hydrochloride salt obtained in Example 81 | 97.9 | 4 |
| Hydrochloride salt obtained in Example 95 | 54.1 | 5 |

TABLE 15

|  | Suppression Rate (%) | Number of Mice |
|---|---|---|
| Control |  | 8 |
| Hydrochloride salt obtained in Example 86 | 31.9 | 7 |
| Hydrochloride salt obtained in Example 88 | 51.5 | 7 |
| Hydrochloride salt obtained in Example 87 | 27.8 | 8 |
| Hydrochloride salt obtained in Example 89 | 22.7 | 8 |
| Hydrochloride salt obtained in Example 90 | 36.7 | 7 |

TABLE 16

|  | Suppression Rate (%) | Number of Mice |
|---|---|---|
| Control |  | 8 |
| Hydrochloride salt | 42.4 | 8 |

TABLE 16-continued

| | Suppression Rate (%) | Number of Mice |
|---|---|---|
| obtained in Example 142 | | |
| Hydrochloride salt obtained in Example 143 | 52.5 | 8 |
| Hydrochloride salt obtained in Example 145 | 66.2 | 8 |
| Hydrochloride salt obtained in Example 146 | 72.8 | 8 |
| Hydrochloride salt obtained in Example 152 | 20.5 | 5 |
| Hydrochloride salt obtained in Example 154 | 55.8 | 7 |
| Hydrochloride salt obtained in Example 156 | 54.4 | 7 |

TABLE 17

| | Suppression Rate (%) | Number of Mice |
|---|---|---|
| Control | | 7 |
| Hydrochloride salt obtained in Example 144 | 82.7 | 7 |
| Hydrochloride salt obtained in Example 137 | 61.9 | 6 |
| Hydrochloride salt obtained in Example 136 | 54.0 | 7 |
| Hydrochloride salt obtained in Example 135 | 78.6 | 7 |
| Hydrochloride salt obtained in Example 155 | 47.9 | 7 |
| Hydrochloride salt obtained in Example 150 | 37.3 | 7 |
| Hydrochloride salt obtained in Example 149 | 75.7 | 7 |
| Hydrochloride salt obtained in Example 82 | 75.2 | 7 |

TABLE 18

| | Suppression Rate (%) | Number of Mice |
|---|---|---|
| Control | | 7 |
| Hydrochloride salt obtained in Example 115 | 26.3 | 7 |
| Hydrochloride salt obtained in Example 116 | 47.9 | 7 |
| Hydrochloride salt obtained in Example 75 | 53.3 | 7 |
| Hydrochloride salt obtained in Example 140 | 61.2 | 5 |
| Hydrochloride salt obtained in Example 151 | 66.2 | 7 |
| Hydrochloride salt obtained in Example 92 | 88.7 | 6 |
| Hydrochloride salt obtained in Example 93 | 41.8 | 6 |

TABLE 18-continued

| | Suppression Rate (%) | Number of Mice |
|---|---|---|
| Hydrochloride salt obtained in Example 92 | 50.2 | 7 |

TABLE 19

| | Suppression Rate (%) | Number of Mice |
|---|---|---|
| Control | | 8 |
| Hydrochloride salt obtained in Example 100 | 58.4 | 8 |
| Hydrochloride salt obtained in Example 141 | 36.1 | 8 |
| Hydrochloride salt obtained in Example 97 | 100.0 | 6 |
| Hydrochloride salt obtained in Example 98 | 48.6 | 8 |
| Hydrochloride salt obtained in Example 114 | 92.0 | 6 |
| Hydrochloride salt obtained in Example 129 | 30.8 | 8 |
| Hydrochloride salt obtained in Example 120 | 63.6 | 7 |

TABLE 20

| | Suppression Rate (%) | Number of Mice |
|---|---|---|
| Control | | 7 |
| Hydrochloride salt obtained in Example 158 | 25.8 | 7 |
| Hydrochloride salt obtained in Example 162 | 59.6 | 7 |
| Hydrochloride salt obtained in Example 182 | 21.3 | 7 |
| Hydrochloride salt obtained in Example 184 | 11.2 | 7 |

TABLE 21

| | Suppression Rate (%) | Number of Mice |
|---|---|---|
| Control | | 7 |
| Sodium salt obtained in Example 172 | 10.9 | 7 |
| Trishydroxymethyl-aminomethane salt obtained in Example 172 | 14.1 | 7 |
| Sodium salt obtained in Example 173 | 13.5 | 7 |
| Hydrochloride salt obtained in Example 188 | 34.5 | 7 |
| Hydrochloride salt obtained in Example 190 | 11.3 | 7 |

From the results shown above, it was confirmed that the compounds of the present invention had excellent effect of suppressing IV-type allergic reaction in its effector phase.

Also, from results of the acute toxicity performed, the safety of the compounds of the present invention was confirmed.

Hence, the compounds of the present invention are useful as antiallergic drugs, effective against IV-type allergy and the like.

The dose amount and the preparation into formulations of the compounds of the invention will now be described.

The compounds of the invention can be administered to animal and man, directly or together with a vehicle commonly used. The dose form is not particularly limited, and is selected appropriately as needed on use, including oral drugs such as tablets, capsules, granules, grains and powder, or non-oral drugs such as injection and suppository.

In order to obtain the desired effect from the oral drugs, it is believed appropriate to administer the compound of the present invention to an ordinary adult in an amount of 1 mg to 600 mg per day, at several times, though the amount depends on the age and weight of the patient and the degree of the disease.

The oral drugs are prepared by ordinary methods, using starch, lactose, sucrose, mannitol, carboxymethylcellulose, corn starch, or inorganic salts.

In the drugs of this type, use can be made of a binder, a disintegrator, a surfactant, a lubricant, a fluidity-promoting agent, a flavor, a tinction, a perfume and the like, in addition to the vehicle mentioned above. Specific examples of some of these substances will be given below:

Binder

Starch, dextrin, powdered acasia, gelatin, hydroxypropylstarch, methylcellulose, carboxymethylcellulose sodium, hydroxypropylcellulose, crystalline cellulose, ethylcellulose, polyvinylpyrrolidone, and macrogol.

Disintegrator

Starch, hydroxypropylstarch, carboxymethylcellulose sodium, carboxymethylcellulose calcium, carboxymethylcellulose, and low-substituted hydroxypropylcellulose.

Surfactant

Sodium laurylsulfate, soybean lecithin, succharose fatty acid ester, and polysorbate 80.

Lubricant

Talc, waxes, hydrogenated vegetable oil, succharose fatty acid ester, magnesium stearate, calcium stearate, aluminum stearate, and polyethylene glycol.

Fluidity-Promoting Agent

Light anhydrous silicic acid, dry aluminum hydroxide gel, synthetic aluminum silicate, and magnesium silicate.

The compounds of the present invention can also be administered in the form of suspension, emulsion, syrup or elixir. These forms of drugs may also contain flavor, perfume and tinction.

In order to obtain the desired effect from the non-oral drugs, it is believed appropriate to administer the compound of the present invention to an ordinary adult in an amount of 1 mg to 200 mg per day in the form of phleboclysis, intravenous drip, hypodermic injection, or intramuscular injection, though the amount depends on the age and weight of the patient, and the degree of the disease.

The non-oral drugs can be prepared by ordinary methods, and use may be made of an attenuant such as distilled water for injection, physiological saline, aqueous solution of glucose, vegetable oil for injection, sesame oil, peanut oil, soybean oil, corn oil, propylene glycol, or polyethylene glycol. If necessary, germicide, preservative, and stabilizer may be added. The non-oral drugs can be filled in a vial or the like and frozen, and then be removed of water by the ordinary freeze-dry technique. A liquid drug can be reformulated from the freeze-dried drug immediately before administration. Further, an isotonic, a stabilizer, a preservative, an antiseptic, a sedative, and the like may be added.

Examples of other non-oral drugs include a lotion, an ointment, and a suppository for intrarectal administration, which are prepared by ordinary methods.

The present invention will be described in greater detail, with reference to examples. The invention is not limited to these examples, nonetheless.

EXAMPLE 1

Acetalization

A solution of 15.3 g of ethyl 4-oxo-1-cyclohexanecarboxylate, 500 ml of ethylene glycol, and 1.8 g of p-toluenesulfonic acid, mixed in 150 ml of toluene, was refluxed and reacted for 3 hours, while the water generated was being removed from the system by a Dean-Stark trap. After reaction, 200 ml of an aqueous sodium chloride solution was added to the ethylene glycol layer. The ethylene glycol layer was extracted three times, with 100 ml of ethyl acetate. The resultant organic layer was combined with the toluene layer, washed three times with an aqueous sodium chloride solution, and then dried over magnesium sulfate. Thereafter, the solvent was removed in vacuo. The oily substance obtained was refined by vacuum distillation, yielding 11.1 g of ethyl 1,4-dioxaspiro 4.5decane-8-carboxylate as a colorless oil, which had the following physiochemical properties:

Boiling point: 114°–116° C./0.6 mmHg

Proton nuclear magnetic resonance spectrum ($\delta$ ppm in CDCl$_3$): 1.21 (3H, t, J=7Hz), 0.8–2.4 (9H, m), 3.94 (4H, s), 4.07 (2H, q, J=7Hz)

IR$_{max}$ (neat, cm$^{-1}$): 3448, 2952, 1730

MS (M+): 214

EXAMPLE 2

Alkylation 4.8 ml of methyl iodide was added to a solution of 11.1 g of ethyl 1,4-dioxaspiro[4.5]decane-8-carboxylate (Example 1) and 11.5 g of sodium hexamethyldisilazide in 300 ml of THF. The solution was reacted at room temperature for 2 hours under an argon stream. After reaction, 200 ml of an aqueous ammonium chloride solution was added to the reaction solution, and the solution was extracted three times with 70 ml of ethyl acetate. The resultant organic layer was washed twice with an aqueous sodium thiosulfate solution and once with an aqueous sodium chloride solution, and was then dried over magnesium sulfate. Thereafter, the solvent was removed in vacuo. The oily substance obtained was refined by vacuum distillation (Kugelrohl), yielding 5.81 g of ethyl 8-methyl-1,4-dioxaspiro 4.5decane-8-carboxylate as a colorless oil, which had the following physiochemical properties:

Boiling point: 200° C./0.3 mmHg (Kugelrohl)
Proton nuclear magnetic resonance spectrum (δ ppm in CDCl$_3$): 1.19 (3H, s), 0.8–2.2 (9H, m), 1.22 (3H, t, J=7Hz), 3.93 (4H, s), 4.09 (2H, q, J=7Hz)
IR$_{max}$ (neat, cm$^{-1}$): 2952, 1726
MS (M+): 227

EXAMPLE 3

Hydrolysis 5.81 g of ethyl 8-methyl-1,4-dioxaspiro[4.5]-decane-8-carboxylate (Example 2) was dissolved in 200 ml of methanol. Then, 30 ml of concentrated hydrochloric acid was added to the solution under ice-cooling, and was stirred at room temperature for one hour.

After reaction, 300 ml of an aqueous sodium hydrogencarbonate solution was added to the reaction solution. The resultant solution was extracted three times with 70 ml of ethyl acetate. The resultant organic layer was washed once with each of an aqueous sodium chloride solution and an aqueous sodium hydrogen-carbonate solution, and was then dried over magnesium sulfate. Thereafter, the solvent was removed in vacuo. The oily substance obtained was refined by vacuum distillation (Kugelrohl), yielding 3.4 g of ethyl 1-methyl-4-oxo-1-cyclohexanecarboxylate as a colorless oil, which had the following physiochemical properties:

Boiling point: 170° C./0.4 mmHg (Kugelrohl)
Proton nuclear magnetic resonance spectrum (δ ppm in CDCl$_3$): 0.8–2.5 (9H,m), 1.26 (3H, t, J=7Hz), 1.30 (3H, s), 4.17 (2H, q, J=7Hz)
IR$_{max}$ (neat, cm$^{-1}$): 2964, 1724
MS (M+): 184

EXAMPLE 4

Reduction 1.6 g of sodium boron hydride was added to a solution of 3.4 g of ethyl 1-methyl-4-oxo-1-cyclohexanecarboxylate (Example 3) in 70 ml of isopropyl alcohol. The resultant solution was reacted at room temperature for 4 hours. After reaction, 2N hydrochloric acid was added to the reaction solution, acidifying the solution. The solution was extracted three times with 30 ml of ethyl acetate. The resultant organic layer was washed three times with an aqueous sodium chloride solution, and was then dried over magnesium sulfate. Thereafter, the solvent was removed in vacuo. To the crude product, 30 ml of 2N aqueous solution of sodium hydroxide and 50 ml of methanol were added. The resultant solution was reacted for 2 hours, while being heated and refluxed. After the reaction, 2N hydrochloric acid was added to the reaction solution, acidifying the solution. The solution was stirred at room temperature for 2 hours. After reaction, the solution was extracted three times with 50 ml of ethyl acetate. The resultant organic layer was washed three times with 30 ml of an aqueous sodium hydrogencarbonate solution, and once with an aqueous sodium chloride solution, and was dried over magnesium sulfate. The solvent was removed in vacuo, yielding 1.2 g of white crystal of 4-methyl-2-oxabicyclo[2.2.2]octan-3-one, which had the following physiochemical properties:

Melting point: 56.8°–57.2° C.
Proton nuclear magnetic resonance spectrum (δ ppm in CDCl$_3$): 1.4–2.1 (8H, m), 1.18 (3H, s), 4.70 (1H, m)
IR$_{max}$ (nujol, cm$^{-1}$): 1766
MS (M+): 140
Elemental analysis (C$_8$H$_{12}$O$_2$):
Theoretical value; C: 68.84, H: 8.63.
Measured value; C: 68.71, H: 8.59.

EXAMPLE 5

Extraction 2N hydrochloric acid was added to 90 ml of the aqueous sodium hydrogencarbonate layer obtained in Example 4, acidifying the layer. The solution was extracted three times with 50 ml of ethyl acetate. The resultant organic layer was washed once with an aqueous sodium chloride solution and was then dried over magnesium sulfate. Thereafter, the solvent was removed in vacuo, yielding 0.9 g of trans-4-hydroxy-1-methyl-1cyclohexanecarboxylic acid as white crystal, which had the following physiochemical properties:

Melting point: 137.3°–138.5° C.
Proton nuclear magnetic resonance spectrum (δ ppm in DMSO-d$_6$):
1.11 (3H, s), 1.2–1.9 (8H, m), 3.57 (1H, m)
IR$_{max}$ (nujol, cm$^{-1}$): 3424, 1704
MS (M+): 158
Elemental analysis (C8H1403): Theoretical value; C: 60.74, H: 8.92. Measured value; C: 60.79, H: 9.07.

EXAMPLE 6

Hydrolysis 30 ml of 2N aqueous solution of sodium hydroxide and 50 ml of methanol were added to 1.2 g of 4-methyl-2-oxabicyclo[2.2.2]octan-3-one (Example 4). Then, the resultant solution was reacted, while it was refluxed. After reaction, 2N hydrochloric acid was added to the solution, weakly acidifying the solution. The solution was then extracted three times with 30 ml of ethyl acetate. The resultant organic layer was washed once with an aqueous sodium chloride solution and dried over magnesium sulfate. The solvent was removed in vacuo, yielding 1 g of white crystal of cis-4-hydroxy-1-methyl-1-cyclohexanecarboxylic acid, which had the following physiochemical properties:

Melting point: 162°–163° C.
Proton nuclear magnetic resonance spectrum (δ ppm in DMSO-d$_6$): 1.0–2.2 (8H, m), 1.07 (3H, s), 3.37 (1H, brs)
IR$_{max}$ (nujol, cm$^{-1}$): 3432, 1692
MS (M+): 158
Elemental analysis (C$_8$H$_{14}$O$_3$):
Theoretical value; C: 60.74, H: 8.92
Measured value; C: 60.83, H: 8.97

EXAMPLE 7

Esterification and Amidation 1.8 g of potassium carbonate and 1.2 ml of allyl bromide were added to a solution of 1 g of cis-4-hydroxy-1-methyl-1-cyclohexanecarboxylic acid (Example 6) in 15 ml of DMF. The resultant solution was reacted at room temperature for 4 hours. After reaction, 50 ml of an aqueous sodium chloride solution was added to the reaction solution. The solution was extracted three times with 20 ml of methylene chloride. The resultant organic layer was washed with an aqueous sodium chloride solution and dried over magnesium sulfate. The solvent was removed in vacuo.

The oily substance, thus obtained, was subjected to column chromatography using 10 g of silica gel. From the fraction eluted with hexane and ethyl acetate=3:1, the solvent was removed in vacuo, yielding 1.1 g of allyl cis-4-hydroxy-1-methyl-1-cyclohexanecarboxylate as a colorless oil, which had the following physiochemical properties:

Proton nuclear magnetic resonance spectrum ($\delta$ ppm in CDCl$_3$): 1.18 (3H, s), 1.4–2.4 (8H, m), 3.61 (1H, m), 4.58 (2H, m), 5.26 (2H, m), 5.96 (1H, m)

MS (M+): 198

EXAMPLE 8

Esterification and Amidation

Using 0.9 g of trans-4-hydroxy-1-methyl-1cyclohexanecarboxylic acid (Example 5), 1.8 g of potassium carbonate, 1.2 ml of allyl bromide, and 15 ml of DMF, a reaction was performed in the same way as in Example 7. As a result, 0.9 g of allyl trans-4-hydroxy-1-methyl-1-cyclohexanecarboxylate was obtained as a colorless oil, which had the following physiochemical properties:

Proton nuclear magnetic resonance spectrum ($\delta$ ppm in CDCl$_3$): 1.23 (3H, s), 1.5–2.3 (8H, m), 3.84 (1H, m), 4.57 (2H, m), 5.26 (2H, m), 5.96 (1H, m)

MS (M+): 198

EXAMPLE 9

Esterification and Amidation 2.3 g of 4-acetoxy-3-methoxycinnamoyl chloride, disclosed in the literature [K. Freudenberg and R. Dillenburg, Chem. Ber., 84, 67–70 (1951), was added to a solution of 1.8 g of allyl cis-4-hydroxy-1-methyl-1-cyclohexanecarboxylic acid (Example 7) in 70 ml of pyridine. The resultant solution was reacted at room temperature for 18 hours. After reaction, the solvent was removed in vacuo. To the residue, 150 ml of 2N hydrochloric acid was added. The resultant solution was extracted three times with 50 ml of ethyl acetate. The organic layer obtained was washed three times with 2N hydrochloric acid, once with an aqueous sodium hydrogencarbonate solution and once with an aqueous sodium chloride solution, and dried over magnesium sulfate. Thereafter, the solvent was removed in vacuo. The resultant oily substance was subjected to column chromatography using 50 g of silica gel. From the fraction eluted with hexane and ethyl acetate=2:1, the solvent was removed in vacuo, yielding 1.6 g of allyl cis-4—(4-acetoxy-3-methoxycinnamoyloxy)-1-methyl-1-cyclohexanecarboxylate (a compound of the present invention) as a pale yellow oil, which had the following physiochemical properties:

Proton nuclear magnetic resonance spectrum ($\delta$ ppm in CDCl$_3$): 1.22 (3H, s), 1.6–2.4 (8H, m), 2.32 (3H, s), 3.86 (3H, s), 4.61 (2H, m), 4.83 (1H, m), 5.28 (2H, m), 5.93 (1H, m), 6.31 (1H, d, J=16Hz), 7.0–7.1 (3H, m), 7.57 (1H, d, J=16Hz)

MS (M+): 416

EXAMPLE 10

Hydrolysis 5 g of potassium carbonate was added to a solution of 1.6 g of allyl cis-4-(4-acetoxy-3-methoxycinnamoyloxy)-1-methyl-1-cyclohexanecarboxylate (Example 9) in 80 ml of methanol. The resultant solution was stirred for 2 hours at room temperature. After reaction, 2N hydrochloric acid was added to the reaction solution, acidifying the solution. The solution was extracted three times with 50 ml of ethyl acetate. The organic layer obtained was washed once with an aqueous sodium hydrogencarbonate solution and once with an aqueous sodium chloride solution, and was then dried over magnesium sulfate. The solvent was removed in vacuo, yielding 0.62 g of allyl cis-4—(4-hydroxy-3-methoxycinnamoyloxy)-1-methyl-1cyclohexanecarboxylate (a compound of the present invention) as white crystal, which had the following physiochemical properties:

Proton nuclear magnetic resonance spectrum ($\delta$ ppm in CDCl$_3$): 1.21 (3H, s), 1.3–2.4 (8H, m), 3.92 (3H, s), 4.61 (2H, m), 4.85 (1H, m), 5.27 (2H, m), 5.94 (1H, m), 6.22 (1H, d, J=16Hz), 6.93 (1H, d, J=21Hz) 7.09 (2H, brs), 7.59 (2H, d, J=16Hz)

MS (M+): 374

EXAMPLE 11

Reduction 0.2 g of bis(triphenylphosphine)palladium dichloride and 4 g of ammonium formate were added to a solution of 6.2 g of allyl cis-4-(4-hydroxy-3-methoxycinnamoyloxy)-1-methyl-1-cyclohexanecarboxylate (Example 10) in 80 ml of THF. The solution was reacted for 20 hours under an argon stream, while it was refluxed. After reaction, 150 ml of an aqueous sodium chloride solution was added to the reaction solution. The solution was extracted three times with 70 ml of ethyl acetate. The organic layer obtained was washed three times with an aqueous sodium chloride solution and dried over magnesium sulfate. Then, the solvent was removed in vacuo. The oily substance obtained was subjected to column chromatography using 50 g of silica gel. From the fraction eluted with hexane and ethyl acetate=1:2, the solvent was removed in vacuo, yielding 0.8 g of cis-4-(4-hydroxy-3-methoxy-cinnamoyloxy)-1-methyl-1-cyclohexanecarboxylic acid (a compound of the present invention) as a pale yellow oil, which had the following physiochemical properties:

Proton nuclear magnetic resonance spectrum ($\delta$ ppm in CDCl$_3$): 1.27 (3H, s), 1.3–2.4 (8H, m), 3.90 (3H, s), 4.91 (1H, m), 6.22 (1H, d, J=16Hz), 6.92 (1H, d, J=21Hz), 7.03 (2H, m), 7.55 (1H, d, J=16Hz)

MS (M+): 334

IR$_{max}$ (KBr, cm$^{-1}$): 3444, 2956, 1740 1696, 1666

HRMS (C$_{18}$H$_{22}$O$_6$): Theoretical value: 334.1416. Measured value: 334.14205.

EXAMPLE 12

Esterification and Amidation 2.3 g of 4-acetoxy-3-methoxycinnamoyl chloride was added to a solution of 1.8 g of allyl trans-4-hydroxy-1-methyl-1-cyclohexanecarboxylate (Example 8) in 70 ml of pyridine. The resultant solution was reacted at room temperature for 18 hours. After reaction, the solvent was removed in vacuo. To the residue, 150 ml of 2N hydrochloric acid was added. The resultant solution was extracted three times with 50 ml of ethyl acetate. The organic layer obtained was washed three times with 2N hydrochloric acid, once with an aqueous sodium hydrogencarbonate solution and once with aqueous sodium chloride solution, and then was dried over magnesium sulfate. Thereafter, the solvent was removed in vacuo. The resultant oily substance was subjected to column chromatography using 50 g of silica gel. From the fraction eluted with hexane and ethyl acetate=2:1, the solvent was removed in vacuo, yielding 1.4 g of allyl trans-4-(4-acetoxy-3-methoxycinnamoyloxy)-1-methyl-1-cyclohexanecarboxylate (a compound of the present invention) as a pale yellow oil, which had the following physiochemical properties:

Proton nuclear magnetic resonance spectrum ($\delta$ ppm in CDCl$_3$): 1.26 (3H, s), 1.3–2.4 (8H, m), 2.32 (3H, s), 3.87 (3H, s), 4.64 (2H, m), 5.05 (1H, m), 5.21 (2H, m), 5.29 (2H, m), 5.38 (2H, m), 5.94 (1H, m), 6.34 (1H, d, J=16Hz), 7.06 (1H, d, J=21Hz), 7.09 (2H, m), 7.59 (1H, d, J=16Hz)

MS (M+): 416

EXAMPLE 13

Hydrolysis 5 g of potassium carbonate was added to a solution of 1.4 g of allyl trans-4-(4-acetoxy-3-methoxycinnamoyloxy)-1-methyl-1-cyclohexanecarboxylate (Example 12) in 70 ml of methanol. The resultant solution was stirred for 2 hours at room temperature. After reaction, 2N hydrochloric acid was added to the solution, acidifying the solution. The solution was extracted three times with 50 ml of ethyl acetate. The organic layer obtained was washed once with an aqueous sodium hydrogencarbonate solution and once with an aqueous sodium chloride solution, and then dried over magnesium sulfate. The solvent was removed in vacuo, yielding 1.09 g of allyl trans-4-(4-hydroxy-3-methoxycinnamoyloxy)-1-methyl-1-cyclohexanecarboxylate (a compound of the present invention) as white crystal, which had the following physiochemical properties:

Proton nuclear magnetic resonance spectrum ($\delta$ ppm in CDCl$_3$): 1.26 (3H, s), 1.3–2.4 (8H, m), 3.94 (3H, s), 4.62 (2H, m), 5.04 (1H, m), 5.2–5.4 (2H, m), 5.94 (1H, m) 6.25 (1H, d, J=16Hz), 6.90 (1H, d, J=21Hz), 7.06 (2H, m), 7.56 (1H, d, J=16Hz)

MS (M+): 374

EXAMPLE 14

Reduction 0.2 g of bis(triphenylphosphine)palladium dichloride and 4 g of ammonium formate were added to a solution of 1.09 g of white crystal of allyl trans-4-(4-hydroxy-3-methoxycinnamoyloxy)-1-methyl-1-cyclohexanecarboxylate (Example 13) in 70 ml of THF. The solution was reacted for 20 hours under an argon stream, while it was refluxed. After reaction, 150 ml of an aqueous sodium chloride solution was added to the reaction solution. The solution was extracted three times with 50 ml of ethyl acetate. The organic layer obtained was washed three times with an aqueous sodium chloride solution, and was dried over magnesium sulfate. Thereafter, the solvent was removed in vacuo. The oily substance obtained was subjected to column chromatography using 50 g of silica gel. From the fraction eluted with hexane and ethyl acetate=1:2, the solvent was removed in vacuo, yielding 0.7 g of trans-4-(4-hydroxy-3-methoxycinnamoyloxy)-1-methyl-1-cyclohexanecarboxylic acid (a compound of the present invention) as white crystal, which had the following physiochemical properties:

Melting point: 172.8°–174.3° C.

Proton nuclear magnetic resonance spectrum ($\delta$ ppm in CDCl$_3$): 1.26 (3H, s), 1.3–2.4 (8H, m), 3.91 (3H, s), 5.04 (1H, m), 6.22 (1H, d, J=16Hz), 6.92 (1H, d, J=21Hz), 7.03 (2H, m), 7.55 (1H, d, J=16Hz)

IR$_{max}$ (KBr, cm$^{-1}$): 3430, 2952, 1730, 1702, 1632

MS (M+): 334

Elemental analysis (C$_{18}$H$_{22}$O$_6$): Theoretical value; C: 64.70, H: 6.60 Measured value; C: 64.71, H: 6.35

EXAMPLE 15

Reductive Amidation 5N hydrochloric acid-methanol was added to a solution of 19.6 ml of benzylamine in 75 ml of methanol under ice-cooling, neutralizing the solution. Then, 5.1 g of methyl 1-methyl-4-oxo-1-cyclohexanecarboxylate and 1.13 g of sodium cyanoborohydride were added to the mixture solution. The solution was reacted at room temperature for 26 hours. After reaction, concentrated hydrochloric acid was added to the reaction solution, adjusting the pH value to 2 or less. The solution was washed three times with 30 ml of methylene chloride. Further, a 2N aqueous sodium hydroxide solution was added to the aqueous layer formed, adjusting the pH value to 10 or more. The solution was extracted three times with 30 ml of ethyl acetate. The organic layer obtained was washed twice with an aqueous sodium chloride solution and dried over magnesium sulfate. The solvent was removed in vacuo. The oily substance, thus obtained, was subjected to column chromatography using 50 g of silica gel. From the fraction eluted with hexane and ethyl acetate=4:1, the solvent was removed in vacuo, yielding 3.1 g of methyl 4-(N-benzylamino)-1-methyl-1-cyclohexanecarboxylate as a colorless oil, which had the following physiochemical properties:

Proton nuclear magnetic resonance spectrum ($\delta$ ppm in CDCl$_3$): 1.18 (3H, s), 1.2–2.3 (9H, m), 3.72 (2H, s), 3.93 (3H, s), 7.2–7.5 (5H, m)

MS [(M+H)+]: 262

EXAMPLE 16

Reduction 0.2 g of 10% palladium-carbon was added to a solution of 3.1 g of methyl 4-(N-benzylamino)-1-methyl-1-cyclohexanecarboxylate (Example 15) in 200 ml of methanol. The solution was reacted at room temperature under normal-pressure hydrogen gas. The reaction was stopped after 20 hours, the catalyst was filtered out, and the solvent was removed in vacuo from the filtrate. As a result, 1.4 g of methyl 4-amino-1-methyl-1-cyclohexanecarboxylate was obtained as a pale yellow oil, which had the following physiochemical properties:

Proton nuclear magnetic resonance spectrum ($\delta$ ppm in CDCl$_3$): 1.19 (3H, s), 1.2–2.2 (11H, m), 3.92 (3H, s)

MS (M+): 173

EXAMPLE 17

Esterification and Amidation 4.2 g of 4-acetoxy-3-methoxycinnamoyl chloride was added to a solution of 1.4 g of methyl 4-amino-1-methyl-1-cyclohexanecarboxylate (Example 16) in 80 ml of pyridine. The resultant solution was reacted at room temperature for 48 hours. After reaction, the solvent was removed in vacuo. To the residue, 150 ml of 2N hydrochloric acid was added. The resultant solution was extracted three times with 50 ml of ethyl acetate. The organic layer obtained was washed twice with 2N hydrochloric acid, once with an aqueous sodium hydrogencarbonate solution, and once with an aqueous sodium chloride solution, and then was dried over magnesium sulfate. Thereafter, the solvent was removed in vacuo. The oily substance obtained was subjected to column chromatography using 50 g of silica gel. From the fraction eluted with hexane and ethyl acetate=2:1, the was solvent removed in vacuo, yielding 1.7 go of methyl 4-(4-acetoxy-3-methoxycinnamamide)-1-methyl-1-cyclohexanecarboxylate (a compound of the present invention) as a pale yellow oil, which had the following physiochemical properties:

Proton nuclear magnetic resonance spectrum ($\delta$ ppm in $CDCl_3$):
1.19 (3/2H, s), 1.23 (3/2H, s),
1.2–2.3 (8H, m), 2.32 (3H, s),
3.7–3.9 ((1H, s), 3.86 (3/2H, s),
3.87 (3/2H, s), 4.88 (1/2H, m),
5.05 (1/2H, brs),
6.31 (1/2H, d, J=16 Hz),
6.34 (1/2H, d, J=16 Hz),
7.0–7.2 (3H, m),
7.61 (1/2H, d, J=16 Hz),
7.69 (1/2H, d, J=16 Hz)
MS [(M+H)+]: 390

EXAMPLE 18

Hydrolysis 1 g of potassium t-butoxide was added to a solution of 1.7 g of methyl 4-(4-acetoxy-3-methoxycinnamamide)-1-methyl-1-cyclohexanecarboxylate (Example 17) in 30 ml of DMSO. The resultant solution was reacted for 24 hours, while being heated to 50° C. After reaction, 100 ml of 2N hydrochloric acid was added to the reaction solution. The solution was extracted five times with 30 ml of ethyl acetate. The organic layer obtained was washed twice with 2N hydrochloric acid, and also twice with an aqueous sodium chloride solution, and then was dried over magnesium sulfate. Thereafter, the solvent was removed in vacuo. The resultant oily substance was subjected to column chromatography using 50 g of silica gel. From the fraction eluted with hexane and ethyl acetate=1:1, the solvent was removed in vacuo, yielding 1.1 g of 4-(4-hydroxy-3-methoxycinnamamido)-1-methyl-1-cyclohexanecarboxylic acid (a compound of the present invention) as a yellow oil, which had the following physiochemical properties:

Proton nuclear magnetic resonance spectrum ($\delta$ ppm in DMSO-$d_6$):
1.16 (3/2H, s), 1.20 (3/2H, s),
1.2–2.3 (8H, m), 3.6–3.8 (1H, m),
3.84 (3/2H, s), 3.85 (3/2H, s),
4.86 (1/2H, m), 5.03 (1/2H, m),
6.30 (1/2H, d, J=16 Hz),
6.32 (1/2H, d, J=16 Hz),
6.9–7.2 (3H, s),
7.59 (1/2H, d, J=16 Hz),
7.67 (1/2H, d, J=16 Hz)
MS [(M+H)+]: 335

EXAMPLE 19

Conversion into Azide 9.5 g of triphenylphosphine and 5.7 ml of diisopropyl azodicarboxylate were added to a solution of 5.2 g of methyl cis-4-hydroxy-1-methyl-1-cyclohexanecarboxylate, disclosed in the literature [T. Sohda, K. Meguro, and Y. Kawamatsu, Chem. Pharm. Bull., 32, 2267–2278 (1984)], in 100 ml of THF. The resultant solution was stirred for 30 minutes at room temperature. Then, 3 g of sodium azide was added to the solution. The solution was reacted further for 4 hours at room temperature. After reaction, 200 ml of 2N hydrochloric acid was added to the solution. The solution was extracted five times with 50 ml of ethyl acetate. The organic layer obtained was washed once with an aqueous sodium hydrogencarbonate solution and twice with an aqueous sodium chloride solution, and was then dried over magnesium sulfate. Thereafter, the solvent was removed in vacuo. The resultant oily substance was subjected to column chromatography using 30 g of silica gel. From the fraction eluted with hexane and ethyl acetate=5:1, the solvent was removed in vacuo, yielding 3.8 g of methyl trans-4-azido-1-methyl-1-cyclohexanecarboxylate as a colorless oil, which had the following physiochemical properties:

Proton nuclear magnetic resonance spectrum ($\delta$ ppm in $CDCl_3$):
1.21 (3H, s), 1.5–2.3 (8H, m),
3.70 (3H, s), 4.17 (1H, m),
$IR_{max}$ (neat, $cm^{-1}$): 3320, 2980, 2100, 1730
MS (M+): 197
Elemental analysis ($C_9H_{15}N_3O_2$):
Theoretical value: 197.11642.
Measured value: 197.11652.

EXAMPLE 20

Hydrolysis 50 ml of a 3N aqueous sodium hydroxide solution was added to a solution of 3.8 g of methyl trans-4-azido-1-methyl-1-cyclohexanecarboxylate (Example 19) in 100 ml of methanol. The resultant solution was reacted for 2 hours, while it was refluxed. After reaction, 2N hydrochloric acid was added to the reaction solution, acidifying the solution. The solution was extracted three times with 50 ml of ethyl acetate. The organic layer obtained was washed twice with an aqueous sodium chloride solution and dried over magnesium sulfate. The solvent was removed in vacuo, yielding 3.6 g of trans-4-azido-1-methyl-1-cyclohexanecarboxylic acid as a colorless oil, which had the following physiochemical properties:

Proton nuclear magnetic resonance spectrum ($\delta$ ppm in $CDCl_3$):
1.20 (3H, s), 1.5–2.3 (8H, m),
3.70 (3H, s), 4.18 (1H, m),
$IR_{max}$ (nujol, $cm^{-1}$): 3276, 2980, 2096, 1712
MS (M+): 179

EXAMPLE 21

Reduction 0.2 g of platinum dioxide was added to a solution of 3.6 g of trans-4-azido-1-methyl-1-cyclohexanecarboxylic acid (Example 20) in 100 ml ethanol. The resultant solution was reacted at room temperature for 18 hours under 3.5 atom hydrogen gas. After reaction, the catalyst was filtered out, and the solvent was removed in vacuo from the filtrate. As a result, 2.6 g of trans-4-amino-1-methyl-1-cyclohexanecarboxylic acid was obtained as a colorless oil, which had the following physiochemical properties:

Proton nuclear magnetic resonance spectrum ($\delta$ ppm in $CDCl_3$):
1.21 (3H, s), 1.4–2.0 (8H, m),
3.96 (1H, br)
MS (M+): 157
HRMS ($C_8H_{15}NO_2$):
Theoretical value: 157.10341.
Measured value: 157.10681.

EXAMPLE 22

Esterification and Amidation 50 ml of allyl alcohol and 0.5 g of p-toluenesulfonic acid were added to a solution of 3.6 g of trans-4-amino-1-methyl-1-cyclohexanecarboxylic acid (Example 21) in 100 ml of toluene. The solution obtained was refluxed and reacted for 6 hours, while the water formed was being removed from the system by a Dean-Stark trap. After reaction, the solution was washed three times with an aqueous sodium chloride solution and dried over magnesium sulfate. The solvent was removed in vacuo, yielding 3.5 g of allyl trans-4-amino-1-methyl-1-cyclcohexanecarboxylate as a colorless oil, which had the following the physiochemical properties:

Proton nuclear magnetic resonance
spectrum ($\delta$ ppm in $CDCl_3$):
1.22 (3H, s), 1.3–2.0 (8H, m),
3.94 (1H, br),
4.54 (2H, d, J=6 Hz),
5.1–5.4 (2H, m), 5.8–6.1 (1H, m)
MS (M+): 197
HRMS ($C_{11}H_{19}NO_2$):
Theoretical value: 197.14160.
Measured value: 197.14240.

EXAMPLE 23

Esterification and Amidation 4.5 g of 4-acetoxy-3-methoxycinnamoyl chloride was added to a solution of 3.5 g of allyl trans-4-amino-1-methyl-1-cyclohexanecarboxylate (Example 22) in 100 ml of pyridine. The resultant solution was reacted at room temperature for 16 hours. After reaction, the solvent was removed in vacuo. To the residue, 150 ml of 2N hydrochloric acid was added. The resultant solution was extracted three times with 50 ml of ethyl acetate. The organic layer obtained was washed three times with 2N hydrochloric acid, once with an aqueous sodium hydrogencarbonate solution and once with an aqueous sodium chloride solution, and then was dried over magnesium sulfate. Thereafter, the solvent was removed in vacuo. The oily substance obtained was subjected to column chromatography using 50 g of silica gel. From the fraction eluted with hexane and ethyl acetate=2:1, the solvent was removed in vacuo, yielding 4.4 g of allyl trans-4-(4-acetoxy-3-methoxycinnamamido)-1-methyl-1-cyclohexanecarboxylate (a compound of the present invention) as a pale yellow oil, which compound had the following physiochemical properties:

Proton nuclear magnetic resonance
spectrum ($\delta$ ppm in $CDCl_3$):
1.21 (3H, s), 1.4–2.1 (8H, m),
2.32 (3H, s), 3.86 (3H, s),
3.89 (1H, m),
4.52 (2H, dd, J=6, 2 Hz),
4.84 (1H, br), 5.1–5.4 (2H, m),
5.8–6.0 (1H, m),
6.34 (1H, d, J=16 Hz),
7.0–7.2 (3H, m),
7.61 (1H, d, J=16 Hz)
MS [(M+H)+]: 416

EXAMPLE 24

Hydrolysis 10 g of potassium carbonate was added to a solution of 4.4 g of allyl trans-4-(4-acetoxy-3-methoxycinnamamido)-1-methyl-1-cyclohexanecarboxylate (Example 23) in 100 ml of methanol. The resultant solution was stirred for 2 hours at room temperature. After reaction, 2N hydrochloric acid was added to the reaction solution, acidifying the solution. The solution was extracted three times with 50 ml of ethyl acetate. The organic layer obtained was washed once with an aqueous sodium hydrogencarbonate solution and once with an aqueous sodium chloride solution, and was then dried over magnesium sulfate. Thereafter, the solvent was removed in vacuo, yielding 2.81 g of allyl trans-4-(4-hydroxy-3-methoxycinnamamido)-1-methyl-1-cyclohexanecarboxylate (a compound of the present invention) as a yellow oil, which had the following physiochemical properties:

Proton nuclear magnetic resonance
spectrum ($\delta$ ppm in $CDCl_3$):
1.21 (3H, s), 1.4–2.1 (8H, m),
3.89 (3H, s), 3.90 (1H, m),
4.54 (2H, dd, J=6, 2 Hz),
4.84 (1H, br),
5.1–5.4 (2H, m), 5.8–6.0 (1H, m),
6.28 (1H, d, J=16 Hz),
6.9–7.1 (3H, s),
7.62 (1H, d, J=16 Hz)
MS [(M+H)+]: 374

EXAMPLE 25

Reduction and Conversion into Non-Toxic Salt 0.5 of bis(triphenylphosphine)palladium dichloride and 7.5 g of ammonium formate were added to a solution of 2.81 g of allyl trans-4-(4-hydroxy-3-methoxycinnamamido)-1-methyl-1-cyclohexanecarboxylate (Example 24) in 100 ml of THF. The solution was reacted for 18 hours under an argon stream, while it was refluxed. After reaction, 150 ml of an aqueous sodium chloride solution was added to the reaction solution. The solution was extracted three times with 50 ml of ethyl acetate. The organic layer obtained was washed three times with an aqueous sodium chloride solution, was then dried over magnesium sulfate. Then, the solvent was removed in vacuo. The oil substance thus obtained was subjected to column chromatography using 50 g of silica gel. From the fraction eluted with hexane and ethyl acetate=1:2, the solvent was removed in vacuo, yielding 1.7 g of trans-4-(4-hydroxy-3-methoxycinnamamido)-1-methyl-1-cyclohexanecarboxylic acid (a compound of the present invention) as a pale yellow oil, which had the following physiochemical properties:

Proton nuclear magnetic resonance
spectrum ($\delta$ ppm in $DMSO-d_6$):
1.20 (3H, s), 1.2–2.3 (8H, m),
3.85 (3H, m), 3.91 (1H, br),
4.86 (1H, br),
6.30 (1H, d, J=16 Hz),
6.9–7.1 (3H, m),
7.59 (1H, d, J=16 Hz),
MS [(M+H)+]: 334

The compound described above was reacted by the ordinary method, converting it into sodium trans-4-(3-methoxy-4-oxidocinnamamido)-1-methyl-1-cyclohexanecarboxylate, which had the following physiochemical properties:

Proton nuclear magnetic resonance
spectrum ($\delta$ ppm in $D_2O$):
1.18 (3H, s), 1.2–2.2 (8H, m), 3.83 (3H, s), 3.90 (1H, brs),
6.29 (1H, d, J=16 Hz),
6.7–7.0 (3H, m),
7.55 (1H, d, J=16 Hz),
MS [(M+H)+]: 378
HRMS ($C_{18}H_{22}NO_5Na_2$):
Theoretical value: 378.12567.
Measured value: 378.12520.

EXAMPLE 26

Hydrolysis 50 ml of a 3N aqueous sodium hydroxide solution was added to a solution of 5 g of methyl 1-methyl-4-oxo-1-cyclohexanecarboxylate, which is disclosed in a literature [T. Sohda, K. Meguro, and Y. Kawamatsu, Chem. Pharm. Bull., 32, 2267–2278 (1984)], in 150 ml of methanol. The resultant solution was reacted for 2 hours, while it was refluxed. After reaction, 2N hydrochloric acid was added to the solution, acidifying the solution. The solution was extracted five times with 50 ml of ethyl acetate. The organic layer obtained was washed three times with an aqueous sodium chloride solution and was then dried over magnesium sulfate. Thereafter, the solvent was removed in vacuo. The oily substance obtained was subjected to column chromatography using 50 g of silica gel. From the fraction eluted with hexane and ethyl acetate=2:1, the solvent was removed in vacuo, yielding 4.1 g of 1-methyl-4-oxo-1-cyclohexanecarboxyic acid as a colorless oil, which had the following physiochemical properties:

Proton nuclear magnetic resonance
spectrum ($\delta$ ppm in $CDCl_3$):
1.38 (3H, s), 1.6–2.6 (8H, m),
MS (M+): 156
HRMS ($C_8H_{12}O_3$):
Theoretical value: 156.07866.
Measured value: 156.07936.

EXAMPLE 27

Olefination

Under an argon stream, 3 ml of dibromomethane and 30 ml of titanium tetrachloride (methylene chloride 2M solution) were added to a solution of 7 g of zinc suspended in 200 ml of THF, under ice-cooling. The resultant solution was stirred for one hour. Then, a solution of 4.1 g of 1-methyl-4-oxo-1-cyclohexanecarboxylic acid (Example 26) in 40 ml of THF was added to the solution. The resultant solution was reacted for 12 hours. After reaction, 500 ml of an aqueous sodium chloride solution was added to the reaction solution. The solution was extracted three times with 100 ml of ethyl acetate. The organic layer obtained was washed three times with an aqueous solution of sodium chloride and dried over magnesium sulfate. The solvent was removed in vacuo. The oily substance formed was subjected to column chromatography using 20 g of silica gel. From the fraction eluted with hexane and ethyl acetate=2:1, the solvent was removed in vacuo, yielding 1.3 g of 1-methyl-4-methylene-1-cyclohexanecarboxylic acid as a colorless oil, which had the following physiochemical properties:

Proton nuclear magnetic resonance
spectrum ($\delta$ ppm in $CDCl_3$):
1.26 (3H, s), 1.25–1.5 (2H, m),
2.0–2.3 (6H, m), 4.64 (2H, s)
Ms [(M+H)+]: 155

EXAMPLE 28

Iodolactonization 7.5 g of iodine was added to a solution of 1.3 g of 1-methyl-4-methylene-1-cyclohexanecarboxylic acid in 50 ml of acetonitrile. The solution was reacted for 3 hours at room temperature. After reaction, 100 ml of an aqueous solution of sodium thiosulfate was added to the reaction solution. The solution was extracted five times with 30 ml of ethyl acetate. The organic layer obtained was washed three times with aqueous sodium thiosulfate solution and two times with an aqueous sodium chloride solution, and was dried over magnesium sulfate. The solvent was removed in vacuo. The oily substance obtained was subjected to column chromatography using 10 g of silica gel. From the fraction eluted with hexane and ethyl acetate=1:1, the solvent was removed in vacuo, yielding 1.1 g of 1-iodomethyl-4-methyl-2-oxabicyclo[2.2.2]octan-3-one as a pale yellow oil, which had the following physiochemical properties:

Proton nuclear magnetic resonance
spectrum ($\delta$ ppm in $CDCl_3$):
1.20 (3H, s), 1.6–2.0 (8H, m),
3.35 (2H, s)
MS (M+): 279
HRMS ($C_9H_{13}O_2I$):
Theoretical value: 279.99628.
Measured value: 279.99848.

EXAMPLE 29

Conversion into Azide 2.6 g of sodium azide was added to a solution of 1.1 g of 1-iodomethyl-4-methyl-2-oxabicyclo[2.2.2]-octan-3-one (Example 28) in 10 ml of DMF. The solution was reacted for 15 hours, while being heated to 100° C. After reaction, 50 ml of an aqueous sodium chloride solution was added to the reaction solution. The solution was then extracted three times with 30 ml of ethyl acetate. The organic layer obtained was washed twice with an aqueous sodium chloride solution and dried over magnesium sulfate. Thereafter, the solvent was removed in vacuo. The oily substance formed was subjected to column chromatography using 5 g of silica gel. From the fraction eluted with hexane and ethyl acetate=1:1, the solvent was removed in vacuo, yielding 0.6 g of 1-azidomethyl-4-methyl-2-oxabicyclo[2.2.2]octan-3-one as a pale yellow oil, which had the following physiochemical properties:

Proton nuclear magnetic resonance
spectrum ($\delta$ppm in $CDCl_3$):
1.20 (3H, s), 1.6–2.0 (8H, m),
3.42 (2H, s)
MS (M+): 195
HRMS ($C_9H_{13}O_2N_3$):
Theoretical value: 195.10077.
Measured value: 195.10227.

EXAMPLE 30

Reduction 0.025 g of platinum dioxide was added to a solution of 0.6 g of 1-azidomethyl-4-methyl-2-oxabicyclo[2.2.2]octan-3-one (Example 29) in 30 ml of ethanol. The resultant solution was reacted for 14 hours under 3.5 atom hydrogen gas. After reaction, the catalyst was filtered out, and the solvent was removed in vacuo from the filtrate. As a result, 0.44 g of 1-aminomethyl-4-methyl- 2-oxabicyclo[2.2.2]-octan-3-one was obtained as a pale yellow oil, which had the following physiochemical properties:
  Proton nuclear magnetic resonance
  spectrum (δ ppm in CDCl$_3$):
  1.21 (3H, s), 1.5–2.0 (8H, m),
  2.52 (2H, brs),
  2.88 (2H, d, J=6 Hz)
  MS (M+): 169
  Elemental analysis (C$_9$H$_{15}$NO$_2$):
  Theoretical value: 169.11017.
  Measured value: 169.10917.

EXAMPLE 31

Esterification and Amidation 0.65 g of 4-acetoxy-3-methoxycinnamoyl chloride was added to a solution of 0.44 g of 1-aminomethyl-4-methyl-2-oxabicyclo[2.2.2]-octan-3-one (Example 30) in 10 ml of pyridine. The resultant solution was stirred at room temperature for 16 hours. After reaction, 30 ml of 2N hydrochloric acid was added to the reaction solution. The resultant solution was extracted five times with 20 ml of ethyl acetate. The organic layer obtained was washed three times with 2N hydrochloric acid, twice with an aqueous sodium hydrogencarbonate solution and once with an aqueous sodium chloride solution, and then was dried over magnesium sulfate. Thereafter, the solvent was removed in vacuo, yielding 0.58 g of N-[1-(4-methyl-2-oxo-3-oxabicyclo[2.2.2]octanyl)methyl]-4-acetoxy-3-methoxycinnamamide (a compound of the present invention) as a pale yellow oil, which had the following physiochemical properties:
  Proton nuclear magnetic resonance
  spectrum (δ ppm in CDCl$_3$):
  1.20 (3H, s), 1.5–1.9 (8H, m),
  2.32 (3H, s), 3.62 (2H, d, J=6 Hz),
  3.87 (3H, s), 6.13 (1H, brs),
  6.34 (1H, d, J=16 Hz),
  7.0–7.2 (3H, m),
  7.55 (1H, d, J=16 Hz)
  MS (M+): 387

EXAMPLE 32

Hydrolysis and Conversion into Non-toxic Salt 5 ml of a 3N aqueous sodium hydroxide solution was added to a solution of 0.58 g of N-[1-(4-methyl-2-oxo-3-oxabicyclo[2.2.2]octanyl)methyl]-4-acetoxy-3-methoxycinnamamide (Example 31) in 10 ml of methanol. The solution formed was reacted for 2 hours, while it was refluxed. After reaction, 2N hydrochloric acid was added to the reaction solution, acidifying the solution, and the solution was extracted five times with 20 ml of ethyl acetate. The organic layer obtained was washed twice with an aqueous sodium chloride solution and dried over magnesium sulfate. Thereafter, the solvent was removed in vacuo. The oily substance formed was subjected to column chromatography using 5 g of silica gel. From the fraction eluted with hexane and ethyl acetate=1:2, the solvent was removed in vacuo, yielding 0.45 g of cis-4-hydroxy-4-[N-(4-hydroxy-3-methoxycinnamoyl)aminomethyl]-1-methyl-1-cyclohexanecarboxylic acid (a compound of the present invention) as a pale yellow oil, which had the following physiochemical properties:
  Proton nuclear magnetic resonance
  spectrum (δ ppm in DMSO-d$_6$):
  1.10 (3H, s), 1.1–2.0 (8H, m),
  3.23 (2H, d, J=5 Hz), 3.82 (3H, s),
  4.42 (1H, s),
  6.60 (1H, d, J=16 Hz),
  6.77 (1H, d, J=8 Hz),
  6.97 (1H, d, J=8 Hz), 7.13 (1H, s),
  7.29 (1H, d, J=16 Hz),
  7.74 (1H, brs), 9.37 (1H, s),
  12.13 (1H, s)
  MS [(M+H)+]: 364

The compound described above was reacted by the ordinary method, converting it into disodium cis-4-hydroxy-4-[N-(3-methoxy-4-oxidocinnamoyl)aminomethyl]-1-methyl-1-cyclohexanecarboxylate, which had the following physiochemical properties:
  Proton nuclear magnetic resonance
  spectrum (δ ppm in D$_2$O):
  1.08 (3H, s), 1.1–2.0 (8H, m),
  3.21 (2H, d, J=5 Hz), 3.80 (3H, s),
  4.40 (1H, s),
  6.57 (1H, d, J=16 Hz),
  6.74 (1H, d, J=8 Hz),
  6.96 (1H, d, J=8 Hz),
  7.10 (1H, s), 7.27 (1H, d, J=16 Hz)
  MS [(M+H)+]: 408
  HRMS (C$_{19}$H$_{24}$NO$_6$Na$_2$):
  Theoretical value: 408.13548.
  Measured value: 408.13676.

EXAMPLE 33

Esterification and Amidation

Under an argon stream, 16 ml of n-butyl lithium (hexane 1.6M solution) was added to a solution of 5 ml bis(trimethylsilyl)amine in 10 ml of THF cooled to −78° C. The resultant solution was stirred for 10 minutes. Then, a solution of 3.4 g of methyl 1-methyl-4-oxo-1-cyclohexanecarboxylate and 8 g of N-phenyl-trifluoromethanesulfonimide in 10 ml of THF was added to the solution, and the temperature was raised to −30° C. The solution was reacted for 1.5 hours. After reaction, the solvent was removed in vacuo. To the residue, 100 ml of aqueous ammonium chloride solution was added. The solution was extracted three times with 50 ml of ethyl acetate. The organic layer obtained was washed twice with 2N hydrochloric acid and twice with an aqueous sodium chloride solution, and was dried over magnesium sulfate. Thereafter, the solvent was removed in vacuo. The oily substance obtained was subjected to column chromatography using 55 g of silica gel. From the fraction eluted with hexane and ethyl acetate=100:1, the solvent was removed in vacuo, yielding 6 g of methyl 1-methyl-4-(trifluoromethanesulfonyloxy)-3-cyclohexene-1-carboxylate as a pale yellow oil, which had the following physiochemical properties:
  Boiling point: 80°–81.1° C./6 mmHg
  Proton nuclear magnetic resonance
  spectrum (δ ppm in CDCl$_3$):
  1.26 (3H, s), 1.3–2.9 (6H, m),
  3.70 (3H, s), 5.72 (1H, brs)
  IR$_{max}$ (neat, cm$^{-1}$): 1734, 1418, 1210
  MS [(M+H)+]: 303
  HRMS (C$_{10}$H$_{14}$O$_5$F$_3$S):
  Theoretical value: 303.05137.
  Measured value: 303.05067.

EXAMPLE 34

Vinylation

A mixed solution of 6 g of methyl 1-methyl-4-(trifluoromethanesulfonyloxy)-3-cyclohexene-1-carboxylate (Example 33), 13 ml of ethylvinylether, 5.5 ml of triethylamine, 0.18 g of palladium diacetate, and 50 ml of DMSO was sealed and reacted at 65° C. under an argon stream. After 3.5 hours, the reacted solution was allowed to cool, and poured into 300 ml of 2N hydrochloric acid. The solution was extracted five times with 100 ml of ether. The organic layer obtained was washed once with an aqueous sodium hydrogencarbonate solution and once with an aqueous sodium chloride solution, treated with activated carbon, and was dried over magnesium sulfate. The solvent was removed in vacuo.

The oily substance obtained was refined by vaccum distillation (Kugelrohl), yielding 2.1 g of methyl 4-acetyl-1-methyl-3-cyclohexene-1-carboxylate as a colorless oil, which had the following physiochemical properties:

Boiling point: 110°–115° C./5 mmHg (Kugelrohl)
Proton nuclear magnetic resonance
spectrum ($\delta$ ppm in $CDCl_3$):
1.23 (3H, s), 1.5–2.9 (6H, m),
2.29 (3H, s), 3.67 (3H, s),
6.88 (1H, brs)
$IR_{max}$ (neat, $cm^{-1}$): 1730, 1668
MS [(M+H)+]: 197
HRMS ($C_{11}H_{17}O_3$):
Theoretical value: 197.11778.
Measured value: 197.11788.

EXAMPLE 35

Reduction 0.1 g of 10% palladium-carbon was added to a solution of 2.1 g of methyl 4-acetyl-1-methyl-3-cyclohexene-1-carboxylate (Example 34) in 50 ml of ethanol. The solution was reacted for 18 hours under normal-pressure hydrogen gas. After reaction, the catalyst was filtered out, and the solvent was removed in vacuo from the filtrate. The oily substance obtained was refined by vacuum distillation (Kugelrohl), yielding 2.1 g of methyl 4-acetyl-1-methyl-1-cyclohexanecarboxylate as a colorless oil, which had the following physiochemical properties:

Boiling point: 125° C./5 mmHg (Kugelrohl)
Proton nuclear magnetic resonance
spectrum ($\delta$ ppm in $CDCl_3$):
1.16 (3H, s), 1.2–2.4 (9H, m),
2.12 (3H, s), 3.68 (3H, s),
$IR_{max}$ (neat, $cm^{-1}$): 1730, 1710
MS [(M+H)+]: 199
HRMS ($C_{11}H_{19}O_3$):
Theoretical value: 199.13331.
Measured value: 199.13271.

EXAMPLE 36

Hydrolysis 20 ml of a 2N aqueous sodium hydroxide solution was added to a solution of 2.1 g of methyl 4-acetyl-1-methyl-1-cyclohexanecarboxylate (Example 35) in 20 ml of ethanol. The solution was reacted for 4 hours, while it was refluxed. After reaction, 2N hydrochloric acid was added to the reaction solution, acidifying the solution. The solution was extracted three times with 50 ml of ethyl acetate. The organic layer obtained was washed twice with an aqueous sodium chloride solution and dried over magnesium sulfate. The solvent was removed in vacuo, and the product obtained was recrystallized from ethyl acetate/hexane, yielding 1.4 g of 4-acetyl-1-methyl-1-cyclohexanecarboxylic acid as white crystal, which had the following physiochemical properties:

Melting point: 104°–107° C.
Proton nuclear magnetic resonance
spectrum ($\delta$ ppm in $CDCl_3$):
1.24 (3H, s), 1.4–2.4 (9H, m),
2.14 (3H, s)
MS (M+): 184
HRMS ($C_{10}H_{16}O_3$):
Theoretical value: 184.10096.
Measured value: 184.11026.

EXAMPLE 37

Esterification and Amidation 1.4 g of 4-acetyl-1-methyl-1-cyclohexanecarboxylic acid (Example 36) was dissolved in 50 ml of DMF, and 5 g of potassium carbonate and 3 ml of allyl bromide were added to the resultant solution. The solution was reacted for 6 hours at room temperature. After reaction, 100 ml of an aqueous sodium chloride solution was added to the reaction solution. The solution was extracted three times with 30 ml of methylene chloride. The organic layer obtained was washed three times with an aqueous sodium chloride solution and dried over magnesium sulfate. Thereafter, the solvent was removed in vacuo. The oily substance obtained was subjected to column chromatography using 20 g of silica gel. From the fraction eluted with hexane and ethyl acetate=10:1, the solvent was removed in vacuo, yielding obtaining 1.5 g of allyl 4-acetyl-1-methyl-1-cyclohexanecarboxylate as a colorless oil, which had the following physiochemical properties:

Proton nuclear magnetic resonance
spectrum ($\delta$ ppm in $CDCl_3$):
1.18 (3H, s), 1.3–2.4 (9H, m),
2.12 (3H, s), 4.57 (2H, d, J=6 Hz),
5.27 (2H, m), 5.30 (2H, m),
5.36 (2H, m), 5.87 (1H, m)
$IR_{max}$ (nujol, $cm^{-1}$): 1730, 1712
MS (M+): 224
HRMS ($C_{13}H_{20}O_3$):
Theoretical value: 224.14112.
Measured value: 224.14112.

EXAMPLE 38

Aldol Condensation

A solution of 1.5 g of 3-methoxy-4-(2-tetrahydropyranyloxy)benzaldehyde, derived from vanillin by the introduction of tetrahydropyranyl group thereinto, 1.5 g of allyl 4-acetyl-1-methyl-1-cyclohexanecarboxylate (Example 37), and 8 ml of sodium hexamethyldisilazide (THF 1M solution), mixed in 50 ml of THF, was reacted for 4 hours under an argon stream, while it was refluxed. After reaction, 100 ml of an aqueous ammonium chloride solution was added to the reaction solution. The solution was extracted three times with 50 ml of ethyl acetate. The organic layer obtained was washed three times with an aqueous sodium chloride solution and dried over magnesium sulfate. Thereafter, the solvent was removed in vacuo. The oily substance obtained was subjected to column chromatography using 50 g of silica gel. From the fraction eluted with hexane and ethyl acetate=4:1, the solvent was removed in vacuo, yielding 1.1 g of allyl 4-[3-methoxy-4-(2-tetrahydropyranyloxy)cinnamoyl]-1-methyl-1-cyclohexanecarboxylate (a compound of the present invention) as a yellow oil, which had the following physiochemical properties:
Proton nuclear magnetic resonance
spectrum ($\delta$ ppm in CDCl$_3$):
1.21 (3/2H, s), 1.25 (3/2H, s),
1.3–2.8 (17H, m),
3.68 (1H, brs), 3.90 (3H, s),
4.58 (2H, dd, J=2, 1 Hz),
5.2–5.4 (2H, m), 5.94 (1H, m),
6.63 (1/2H, d, J=16 Hz).
6.64 (1/2H, d, J=16 Hz),
7.12 (3H, m),
7.49 (1/2H, d, J=16 Hz),
7.50 (1/2H, d, J=16 Hz)
MS [(M+H)+]: 443

EXAMPLE 39

Hydrolysis 10 ml of 2N hydrochloric acid - methanol was added to a solution of 1.1 g of allyl 4-[3-methoxy-4-(2-tetrahydropyranyloxy)cinnamoyl]-1-methyl-1-cyclohexanecarboxylate (Example 38) in 30 ml of methanol. The solution was stirred for 0.5 hours at room temperature. After reaction, 100 ml of an aqueous sodium chloride solution was added to the reaction solution. The solution was extracted three times with 50 ml of ethyl acetate. The organic layer obtained was washed twice with an aqueous sodium chloride solution and dried over magnesium sulfate. Thereafter, the solvent was removed in vacuo, yielding 0.85 g of allyl 4-(4-hydroxy3-methoxycinnamoyl)-1-methyl-1-cyclohexanecarboxylate (a compound of the present invention) as a pale yellow oil, which had the following physiochemical properties:
Proton nuclear magnetic resonance
spectrum ($\delta$ ppm in CDCl$_3$):
1.21 (3/2H, s), 1.26 (3/2H, s),
1.3–2.8 (9H, m), 3.94 (3H, s),
4.55 (2H, dd, J=2, 1 Hz),
5.18 (2H, m),
5.29 (2H, m), 5.4 (2H, m),
5.95 (1H, m),
6.54 (1/2H, d, J=16 Hz),
6.56 (1/2H, d, J=16 Hz),
6.77 (1H, d, J=21 Hz),
7.06 (2H, brs),
7.43 (1/2H, d, J=16 Hz),
7.44 (1/2H, d, J=16 Hz)
MS (M+): 358
HRMS (C$_{21}$H$_{26}$O$_5$):
Theoretical value: 358.17801.
Measured value: 358.17811.

EXAMPLE 40

Reduction and Conversion into Non-toxic Salt 0.1 g of bis(triphenylphosphine)palladium dichloride and 1.5 g of ammonium formate were added to a solution of 0.85 g of allyl 4-(4-hydroxy-3-methoxycinnamoyl)-1-methyl-1-cyclohexanecarboxylate (Example 39) in 80 ml of THF. The solution was reacted for 20 hours under an argon stream, while it was refluxed. After reaction, 150 ml of an aqueous sodium chloride solution was added to the reaction solution. The solution was extracted four times with 50 ml of ethyl acetate. The organic layer formed was washed three times with an aqueous sodium chloride solution and dried over magnesium sulfate. Thereafter, the solvent was removed in vacuo.

The oily substance obtained was subjected to column chromatography using 5 g of silica gel. From the fraction eluted with hexane and ethyl acetate=2:1, the solvent was removed in vacuo, yielding 0.53 g of 4-(4-hydroxy-3-methoxycinnamoyl)-1-methyl-1-cyclohexanecarboxylic acid (a compound of the present invention) as a pale yellow oil, which had the following physiochemical properties:
Proton nuclear magnetic resonance
spectrum ($\delta$ ppm in CDCl$_3$):
1.27 (3/2H, s), 1.29 (3/2H, s),
1.2–2.8 (9H, m), 3.94 (3/2H, s),
3.95 (3/2H, s), 5.94 (1H, brs),
6.70 (1/2H, d, J=16 Hz),
6.72 (1/2H, d, J=16 Hz),
6.95 (1H, dd, J=21, 1 Hz),
7.10 (2H, m),
7.49 (1/2H, d, J=16 Hz),
7.51 (1/2H, d, J=16 Hz)
MS (M+): 318
HRMS (C$_{18}$H$_{22}$O$_5$):
Theoretical value: 318.14674.
Measured value: 318.14754.

The compound described above was reacted in the ordinary method, converting it into disodium 4-(3-methoxy-4-oxidocinnamoyl)-1-methyl-1-cyclohexanecarboxylate, which had the following physiochemical properties:
Proton nuclear magnetic resonance
spectrum ($\delta$ ppm in D$_2$O):
1.26 (3/2H, s), 1.27 (3/2H, s),
1.1–2.8 (9H, m), 3.92 (3/2H, s),
3.94 (3/2H, s), 5.92 (1H, br),
6.68 (1/2H, d, J=16 Hz),
6.70 (1/2H, d, J=16 Hz),
6.91 (1H, d, J=21 Hz),
7.08 (2H, m),
7.47 (1/2H, d, J=16 Hz),
7.49 (1/2H, d, J=16 Hz)
MS [(M+H)+]: 363
HRMS (C$_{18}$H$_{21}$O$_5$Na$_2$):
Theoretical value: 363.10994.
Measured value: 363.11509.

EXAMPLE 41

Olefination

Under an argon stream, 5.3 ml of dibromomethane and 28 ml of titanium tetrachloride (methylene chloride 2M solution) were added to a solution of 15 g of zinc suspended in 250 ml of THF, under ice cooling. The resultant solution was stirred for one hour. Then, a solution of 8.5 g of methyl 1-methyl-4-oxo-1-cyclohexanecarboxylate in 50 ml of THF was added to the solution. The solution was reacted for 15 hours. After reaction, 500 ml of an aqueous sodium chloride solution was added to the reaction solution. The solution was extracted three times with 100 ml of ethyl acetate. The organic layer obtained was washed three times with an aqueous sodium chloride solution and dried over magnesium sulfate. The solvent was removed in vacuo. The oily substance formed was subjected to column chromatography using 100 g of silica gel. From the fraction eluted with hexane and ethyl acetate=50:1, the solvent was removed in vacuo, yielding 7 g of methyl 1-methyl-4-methylene-1-cyclohexanecarboxylate as a colorless oil, which had the following physiochemical properties:

Proton nuclear magnetic resonance
spectrum (δ ppm in CDCl$_3$):
1.19 (3H, s), 1.2–1.4 (8H, m),
2.0–2.4 (8H, m), 3.70 (3H, s),
4.62 (2H, brs)
IR$_{max}$ (neat, cm$^{-1}$): 1732
MS [(M+H)+]: 169

EXAMPLE 42

Hydroboration

Under an argon stream, 12 ml of borane-dimethy sulfide complex (THF 2M solution) was added to a solution of 7 g of methyl 1-methyl-4-methylene-1-cyclohexanecarboxylate (Example 41) in 200 ml of THF, under ice-cooling. The resultant solution was reacted for 2.5 hours at room temperature. Then, 100 ml of purified water was added to the reaction solution. After hydrogen gas ceases to be generated, 50 ml of 3N aqueous sodium hydroxide solution was added to the solution under ice-cooling. Ten minutes later, 50 ml of an aqueous hydrogen peroxide solution was added, and the resultant solution was stirred for 1 hour at 50° C. After reaction, 500 ml of an aqueous sodium chloride solution was added to the reaction solution, thereby isolating the THF layer, which was dried over magnesium sulfate. Thereafter, the solvent was removed in vacuo. The oily substance obtained was subjected to column chromatography using 50 g of silica gel. From the fraction eluted with hexane and ethyl acetate=2:1, the solvent was removed in vacuo, yielding 4.5 g of methyl 4-hydroxymethyl-1-methyl-1-cyclohexanecarboxylate as a colorless oil, which had the following physiochemical properties:

Proton nuclear magnetic resonance
spectrum (δ ppm in CDCl$_3$):
0.9–2.2 (9H, m), 1.16 (3/2H, s),
1.20 (3/2H, s),
3.41 (2H, dd, J=9, 7 Hz),
3.68 (3H, s)
IR$_{max}$ (neat, cm$^{-1}$): 3416, 1730
MS [(M+H)+]: 187

EXAMPLE 43

Hydrolysis 50 ml of 3N aqueous sodium hydroxide solution was added to a solution of 4.5 g of methyl 4-hydroxymethyl-1-methyl-1-cyclohexanecarboxylate (Example 42) in 100 ml of methanol. The solution was reacted for 2 hours, while it was refluxed. After reaction, 2N hydrochloric acid was added to the reaction solution, acidifying the solution. The solution was extracted five times with 50 ml of ethyl acetate. The organic layer obtained was washed three times with an aqueous sodium chloride solution and dried over magnesium sulfate. Thereafter, the solvent was removed in vacuo. The oily substance obtained was subjected to column chromatography using 50 g of silica gel. From the fraction eluted with hexane and ethyl acetate=1:1, the solvent was removed in vacuo, yielding 2.5 g of 4-hydroxymethyl-1-methyl-1-cyclohexanecarboxylic acid as a pale yellow oily, which had the following physiochemical properties:

Proton nuclear magnetic resonance
spectrum (δ ppm in CDCl$_3$):
1.22 (3/2H, s), 1.24 (3/2H, s),
1.0–2.3 (9H, m), 2.05 (3H, s),
3.44 (2H, dd, J=7, 6 Hz)
IR$_{max}$ (neat, cm$^{-1}$): 3420, 2936, 1702
MS [(M+H)+]: 173
HRMS (C$_9$H$_{17}$O$_3$):
Theoretical value: 173.11777.
Measured value: 173.11660.

EXAMPLE 44

Esterification and Amidation 2.2 g of sodium hydrogencarbonate and 1.5 ml of methyl iodide were added to a solution of 2.5 g of 4-hydroxymethyl-1-methyl-1-cyclohexanecarboxylic acid (Example 43) in 100 ml of DMF. The solution was reacted for 15 hours at room temperature. After reaction, 200 ml of 2N hydrochloric acid was added to the reaction solution. The solution was extracted five times with 50 ml of ethyl acetate. The organic layer obtained was washed twice with an aqueous sodium hydrogencarbonate solution and twice with an aqueous sodium chloride solution, and was dried over magnesium sulfate. Thereafter, the solvent was removed in vacuo. The oily substance obtained was subjected to column chromatography using 10 g of silica gel. From the fraction eluted with hexane and ethyl acetate=2:1, the solvent was removed in vacuo, yielding 2.1 g of allyl 4-hydroxymethyl-1-methyl-1-cyclohexanecarboxylate as a pale yellow oil, which had the following physiochemical properties:

Proton nuclear magnetic resonance
spectrum (δ ppm in CDCl$_3$):
0.8–2.3 (9H, m), 1.18 (3/2H, s),
1.22 (3/2H, s),
3.42 (2H, dd, J=9, 6 Hz ),
4.57 (2H, dd, J=2, 1 Hz),
5.2–5.4 (2H, m), 5.88 (1H, m)
IR$_{max}$ (neat, cm$^{-1}$): 3452, 2936, 1728
MS (M+): 212
HRMS (C$_{12}$H$_{20}$O$_2$):
Theoretical value: 212.14126.
Measured value: 212.14216.

EXAMPLE 45

Esterification and Amidation 4.5 ml of mesyl chloride was added to a solution of 2.1 g of allyl 4-hydroxymethyl-1-methyl-1-cyclohexanecarboxylate (Example 44) in 50 ml of pyridine. The solution was reacted for 3 hours at room temperature. After reaction, 100 ml of 2N hydrochloric acid was added to the reaction solution. The solution was extracted three times with 30 ml of ethyl acetate. The organic layer obtained was washed once with an aqueous sodium hydrogencarbonate solution and twice with an aqueous sodium chloride solution, and was dried over magnesium sulfate. Thereafter, the solvent was removed in vacuo. The oily substance obtained was subjected to column chromatography using 20 g of silica gel. From the fraction eluted with hexane and ethyl acetate=2:1, the solvent was removed in vacuo, yielding 2 g of allyl 4-mesyloxymethyl-1-methyl-1-cyclohexanecarboxylate as a pale yellow oil, which had the following physiochemical properties:

Proton nuclear magnetic resonance
spectrum (δ ppm in CDCl$_3$):
0.9–2.3 (9H, m), 1.19 (3/2H, s),
1.22 (3/2H, s), 2.99 (3/2H, s), 3.01 (3/2H, s),
3.98 (2H, dd, J=11, 6 Hz),
4.57 (2H, dd, J=2 Hz),
5.2–5.3 (2H, brs), 5.85 (1H, m)
MS [(M+H)+]: 291
HRMS (C$_{13}$H$_{23}$O$_5$S):
Theoretical value: 291.12662.
Measured value: 291.12480.

EXAMPLE 46

Halogenation 5 g of sodium iodide was added to a solution of 2 g of allyl 4-mesyloxymethyl-1-methyl-1-cyclohexanecarboxylate (Example 45) in 50 ml of acetone. The solution was reacted for 4 hours, while it was refluxed. After reaction, 100 ml of an aqueous sodium thiosulfate solution was added to the reaction solution. The solution was extracted three times with 30 ml of ethyl acetate. The organic layer obtained was washed twice with an aqueous sodium thiosulfate solution and twice with an aqueous sodium chloride solution, and was dried over magnesium sulfate. Thereafter, the solvent was removed in vacuo. The oily substance obtained was subjected to column chromatography using 10 g of silica gel. From the fraction eluted with hexane and ethyl acetate=2:1, the solvent was removed in vacuo, yielding 1.1 g of allyl 4-iodomethyl-1-methyl-1-cyclohexanecarboxylate as a pale yellow oil, which had the following physiochemical properties:

Proton nuclear magnetic resonance
spectrum (δ ppm in CDCl$_3$):
0.9–2.3 (9H, m), 1.18 (3/2H, s),
1.21 (3/2H, s),
3.04 (2H, dd, J=13, 6 Hz),
4.57 (2H, m), 5.20 (2H, m),
5.25 (2H, m), 5.27 (2H, m),
5.85 (1H, m),
MS [(M+H)+]): 323
HRMS (C$_{12}$H$_{20}$O$_2$I):
Theoretical value: 323.05081.
Measured value: 323.04990.

EXAMPLE 47

Alkylation 5 g of potassium carbonate and 1.1 g of allyl 4-iodomethyl-methyl-1-cyclohexanecarboxylate (Example 46) were added to a solution of 0.8 g of allyl 3-hydroxy-4-methoxycinnamate, derived from 3-hydroxy-4-methoxycinnamic acid by the allyl-esterification thereof, in 50 ml of DMF. The solution was reacted for 18 hours at 100° C. After reaction, 100 ml of an aqueous sodium chloride solution was added to the reaction solution. The solution was extracted three times with 50 ml of ethyl acetate. The organic layer obtained was washed three times with an aqueous sodium chloride solution and was dried over magnesium sulfate. Thereafter, the solvent was removed in vacuo. The oily substance obtained was subjected to column chromatography using 5 g of silica gel. From the fraction eluted with hexane and ethyl acetate=2:1, the solvent was removed in vacuo, yielding 0.7 g of allyl 3-[1-(4-allyloxycarbonyl-4-methylcyclohexyl)methoxy]-4-methoxycinnamate (a compound of the present invention) as a pale yellow oil, which had the following physiochemical properties:

Proton nuclear magnetic resonance
spectrum (δ ppm in CDCl$_3$):
1.1–2.4 (9H, m), 1.21 (3/2H, s),
1.23 (3/2H, s),
3.76 (2H, dd, J=13, 6 Hz),
3.89 (3/2H, s), 3.90 (3/2H, s),
4.58 (2H, dd, J=2, 1 Hz),
4.70 (2H, d, J=2 Hz),
5.2–5.5 (4H, m), 5.8–6.1 (2H, m),
6.29 (1/2H, d, J=16 Hz),
6.31 (1/2H, d, J=16 Hz),
6.85 (1H, dd, J=6, 2 Hz),
7.09 (2H, m),
7.61 (1/2H, d, J=16 Hz),
7.62 (1/2H, d, J=16 Hz)
MS (M)+): 428
HRMS:
Theoretical value: 428.21983.
Measured value: 428.21963.

EXAMPLE 48

Hydrolysis

At −78° C., 0.3 ml of boron tribromide was added to a solution of 0.7 g of allyl 3-[1-(4-allyloxycarbonyl-4-methylcyclohexyl)methoxy]-4-methoxycinnamate (Example 47) in 10 ml of methylene chloride. The solution was reacted for 20 minutes in this state. After reaction, 20 ml of an aqueous ammonium chloride solution was added to the reaction solution. The solution was extracted three times with 30 ml of ethyl acetate. The oily substance obtained was washed three times with an aqueous sodium chloride solution and was dried over magnesium sulfate. Thereafter, the solvent was removed in vacuo, yielding 0.26 g of allyl 3-{1-[4-(allyloxycarbonyl)-4-methylcyclohexyl]methoxy}-4-hydroxycinnamate (a compound of the present invention) as a pale yellow oil, which had the following physiochemical properties:

Proton nuclear magnetic resonance
spectrum (δ ppm in CDCl$_3$):
1.1–2.4 (9H, m), 1.21 (3/2H, m),
1.23 (3/2H, s),
3.75 (2H, dd, J=13, 6 Hz),
4.57 (2H, dd, J=2, 1 Hz)
4.70 (2H, dd, J=2, 1 Hz),
5.2–5.5 (4H, m), 5.8–6.1 (2H, m),
6.28 (1/2H, d, J=16 Hz),
6.30 (1/2H, d, J=16 Hz),
6.83 (1H, dd, J=6, 2 Hz),
7.11 (2H, m),
7.60 (1/2H, d, J=16 Hz),
7.61 (1/2H, d, 16 Hz)
MS (M)+): 414

EXAMPLE 49

Reduction and Conversion into Non-toxic Salt 0.08 g of bis(triphenylphosphine)palladium dichloride and 1.2 g of ammonium formate were added to a solution of 0.26 g of allyl 3-{1-[4-(allyloxycarbonyl)-4-methylcyclohexyl]methoxy}-4-hydroxycinnamate (Example 48) in 40 ml of THF. Under an argon stream, the solution was reacted for 20 hours, while it was refluxed. After reaction, 100 ml of an aqueous sodium chloride solution was added to the reaction solution. The solution was extracted five times with 30 ml of ethyl acetate. The organic layer obtained was washed three times with an aqueous sodium chloride solution and dried over magnesium sulfate. Thereafter, the solvent was removed in vacuo.

The oily substance obtained was subjected to column chromatography using 5 g of silica gel. From the fraction eluted with hexane and ethyl acetate=1:2, the solvent was removed in vacuo, yielding 0.13 g of 3-[1-(4-carboxy-4-methylcyclohexyl)methoxy]-4-hydroxycinnamic acid (a compound of the present invention) as pale yellow oil, which had the following physiochemical properties:

Proton nuclear magnetic resonance
spectrum ($\delta$ ppm in DMSO-$d_6$):
1.2–2.4 (9H, m), 1.23 (3/2H, s),
1.25 (3/2H, s),
3.77 (2H, dd, J=13, 6 Hz),
6.25 (1/2H, d, J=16 Hz),
6.27 (1/2H, d, J=16 Hz),
6.81 (1H, d, J=6 Hz), 7.03 (2H, m),
7.56 (1/2H, d, J=16 Hz),
7.57 (1/2H, d, J=16 Hz)
MS (M+): 334

The compound described above was reacted in the ordinary method, converting it into trisodium 3-[1-(4-carboxylato-4-methylcyclohexyl)methoxy]-4-oxidocinnamate, which had the following physiochemical properties:

Proton nuclear magnetic resonance
spectrum ($\delta$ ppm in $D_2O$):
1.1–2.4 (9H, m), 1.21 (3/2H, s),
1.22 (3/2H, s),
3.75 (2H, dd, J=13, 16 Hz),
6.21 (1/2H, d, J=16 Hz),
6.25 (1/2H, d, J=16 Hz),
6.79 (1H, d, J=6 Hz), 7.00 (2H, m),
7.54 (1/2H, d, J=16 Hz),
7.55 (1H, d, J=16 Hz)
MS [(M+H)+]: 401
HRMS ($C_{18}H_{20}O_6Na_3$):
Theoretical value: 401.08981.
Measured value: 401.09038.

EXAMPLE 50

Alkylation 0.09 g of sodium hydride and 1.1 g of 1-iodomethyl-4-methyl-2-oxabicyclo[2.2.2]octan-3-one were added to a solution of 0.8 g of methyl 3-hydroxy-4-methoxycinnamate, derived from 3-hydroxy-4-methoxycinnamic acid by the methyl-esterification thereof, in 50 Ml of DMF. Under an argon stream, the solution was reacted for 16 hours at 50° C. After reaction, 100 ml of an aqueous ammonium chloride solution was added to the reaction solution. The solution was extracted three times with 50 ml of ethyl acetate. The organic layer obtained was washed three times with an aqueous sodium chloride solution and dried over magnesium sulfate. Thereafter, the solvent was removed in vacuo. The oily substance obtained was subjected to column chromatography using 5 g of silica gel. From the fraction eluted with hexane and ethyl acetate=2:1, the solvent was removed in vacuo, yielding 0.68 g of methyl 4-methoxy-3-[1-(4-methyl-2-oxo-3-oxabicyclo[2.2.2]octanyl)methoxy]cinnamate (a compound of the present invention) as a pale yellow, oil, which had the following physiochemical properties:

Proton nuclear magnetic resonance
spectrum ($\delta$ ppm in $CDCl_3$):
1.21 (3H, s), 1.7–2.1 (8H, m),
3.81 (3H, S), 3.88 (2H, S),
3.90 (3H, S),
6.27 (1H, d, J=16HZ),
6.89 (1H, d, J=6HZ),
7.1–7.3 (2H, m),
7.58 (1H, d, J=16 Hz)
MS (M+): 359

EXAMPLE 51

Hydrolysis

At −78° C., 0.3 ml of boron tribromide was added to a solution of 0.68 g of methyl 4-methoxy-3-[1-(4-methyl-2-oxo-3-oxabicyclo[2.2.2]octanyl)methoxy]cinnamate (Example 50) in 10 ml of methylene chloride. The solution was reacted for 15 minutes, as it was. After reaction, 30 ml of an aqueous ammonium chloride solution was added to the reaction solution. The solution was extracted three times with 30 ml of ethyl acetate. The organic layer obtained was washed three times with an aqueous sodium chloride solution and was dried over magnesium sulfate. Thereafter, the solvent was removed in vacuo, yielding 0.21 g of methyl 4-hydroxy-3-[1-(4-methyl-2-oxo-3-oxabicyclo[2.2.2]octanyl)methoxy]cinnamate (a compound of the present invention) as a pale yellow oil, which had the following physiochemical properties:

Proton nuclear magnetic resonance
spectrum ($\delta$ ppm in $CDCl_3$):
1.21 (3H, s), 1.7–2.1 (8H, s),
3.81 (3H, s), 3.87 (3H, s),
6.26 (1H, d, J=16 Hz),
6.87 (1H, d, J=6 Hz),
7.0–7.2 (2H, m),
7.56 (1H, d, J=16 Hz)
MS (M)+): 345

EXAMPLE 52

Hydrolysis and Conversion into Non-toxic Salt 10 ml of 3N aqueous sodium hydroxide solution was added to a solution of 0.21 g of methyl 4-hydroxy-3-[1-(4-methyl-2-oxo-3-oxabicyclo[2.2.2]octanyl)methoxy]-cinnamate (Example 51) in 30 ml of methanol. The solution was reacted for 3 hours, while it was refluxed. After reaction, 100 ml of 2N hydrochloric acid was added to the reaction solution. The solution was extracted five times with 30 ml of ethyl acetate. The organic layer obtained was washed three times with an aqueous sodium chloride solution and dried over magnesium sulfate. Thereafter, the solvent was removed in vacuo.

The oily substance obtained was subjected to column chromatography using 5 g of silica gel. From the fraction eluted with hexane and ethyl acetate=1:2, the solvent was removed in vacuo, yielding 0.16 g of 4-hydroxy-3-[1-(4-carboxy-1-hydroxy-4-methylcyclohexyl)methoxy]cinnamic acid (a compound of the present invention) as a pale yellow oil, which had the following physiochemical properties:

Proton nuclear magnetic resonance
spectrum ($\delta$ ppm in DMSO-$d_6$):
1.23 (3H, s), 1.6–2.2 (8H, m),
3.86 (2H, s),
6.25 (1H, d, J=16 Hz),
6.87 (1H, d, J=6 Hz),
7.1–7.4 (2H, m),
7.56 (1H, d, J=16 Hz)
MS [(M+H)+]: 350

The compound described above was reacted in the ordinary method, converting it into irisodium 3-[1-(4- carboxylato-1-hydroxy-4-methylcyclohexyl)methoxy]-4-oxidocinnamate, which had the following physiochemical properties:

Proton nuclear magnetic resonance
spectrum (δ ppm in D$_2$O):
1.21 (3H, s), 1.5-2.1 (8H, m),
3.84 (2H, s),
6.21 (1H, d, J=16 Hz),
6.85 (1H, d, J=7 Hz),
7.0-7.3 (2H, m),
7.54 (1H, d, J=16 Hz)
MS [(M+H)+]: 417
HRMS (C$_{18}$H$_{20}$O$_7$Na$_3$):
Theoretical value: 417.08501.
Measured value: 417.08530.

EXAMPLE 53

Esterification and Amidation 2 ml of piperidine was added to a solution of 5.09 g of 4-acetoxy-3-methoxycinnamoyl chloride in 100 ml of pyridine. The solution was reacted for hours at room temperature. After reaction, 200 ml of 2N hydrochloric acid was added to the reaction solution. The solution was extracted three times with 100 ml of ethyl acetate. The organic layer obtained was washed three times with 2N hydrochloric acid, twice with an aqueous sodium hydrogencarbonate solution and twice with an aqueous sodium chloride solution, and then was dried over magnesium sulfate. Thereafter, the solvent was removed in vacuo, and the product obtained was recrystallized from methylene chloride/hexane, yielding 1.88 g of 1-(4-acetoxy-3-methoxycinnamoyl)piperidine (a compound of the present invention) as pale yellowish white crystal, which had the following physiochemical properties:

Melting point: 129.6°-130.3° C.
Proton nuclear magnetic resonance
spectrum (δ ppm in CDCl$_3$):
1.6-1.8 (6H, br), 2.32 (3H, s),
3.6-3.8 (4H, br), 3.87 (3H, s),
6.80 (1H, d, J=16 Hz),
7.1-7.3 (3H, m),
7.55 (1H, d, J=16 Hz)
IR$_{max}$ (KBr, cm$^{-1}$): 2936, 1760, 1648
MS (M+): 303
Elemental analysis (C$_{17}$H$_{21}$NO$_4$):
Theoretical value; C: 67.31, H: 6.98, N: 4.62.
Measured value; C: 67.36, H: 6.96, N: 4.81.

EXAMPLE 54

Hydrolysis and Conversion into Non-toxic Salt 5 g of potassium carbonate was added a solution of 1.88 g 1-(4-acetoxy-3-methoxycinnamoyl)piperidine (Example 53) in 70 ml of methanol. The solution was vigorously stirred for 2.5 hours at room temperature.

After reaction, 2N hydrochloric acid was added to the reaction solution, acidifying the solution. The solution was extracted three times with 50 ml of ethyl acetate. The organic layer obtained was washed twice with an aqueous sodium chloride solution and dried over magnesium sulfate. Thereafter, the solvent was removed in vacuo, and the product obtained was recrystallized from ethyl acetate/hexane, yielding 1.51 g of 1-(4-hydroxy-3-methoxycinnamoyl)piperidine (a compound of the present invention) as pale yellow crystal, which had the following physiochemical properties:

Melting point: 136.6°-137.1° C.
Proton nuclear magnetic resonance
spectrum (δ ppm in CDCl$_3$):
1.5-1.8 (6H, br), 3.5-3.8 (4H, br),
3.92 (3H, s), 6.27 (1H, s),
6.71 (1H, d, J=16 Hz),
6.89 (1H, d, J=8 Hz),
6.08 (1H, d, J=2 Hz),
7.06 (1H, dd, J=2, 6 Hz),
7.55 (1H, d, J=16 Hz)
IR$_{max}$ (KBr, cm$^{-1}$): 3268, 2936, 1640, 1620
MS (M+): 261
Elemental analysis (C$_{15}$H$_{19}$NO$_3$):
Theoretical value; C: 68.94, H: 7.33, N: 5.36.
Measured value; C: 68.77, H: 7.34, N: 5.50.

The compound described above was reacted in the ordinary method, converting it into sodium 1-(3-methoxy-4-oxidocinnamoyl)piperidine, which had the following physiochemical properties:

Melting point: 270°-271° C.
Proton nuclear magnetic resonance
spectrum (δ ppm in D$_2$O):
1.4-1.7 (6H, m), 3.5-3.7 (5H, m),
3.82 (3H, s), 6.63 (1H, d, J=8 Hz),
6.75 (1H, d, J=16 Hz),
7.09 (1H, d, J=8 Hz),
7.15 (1H, s), 7.40 (1H, d, J=16 Hz)
MS [(M+H)+]: 284
HRMS (C$_{15}$H$_{19}$NO$_3$Na):
Theoretical value: 284.12629.
Measured value: 284.12470.

EXAMPLE 55

Esterification and Amidation

Using 5.09 g of 4-acetoxy-3-methoxycinnamoyl chloride, 2.4 ml of 4-methylpiperidine, and 100 ml of pyridine, a reaction similar to that conducted in Example 53 was carried out. As a result, 5.2 g of 1-(4-acetoxy-3-methoxycinnamoyl)-4-methylpiperidine (a compound of the present invention) was obtained as an orange-yellow oil, which had the following physiochemical properties:

Proton nuclear magnetic resonance
spectrum (δ ppm in CDCl$_3$):
0.95 (3H, d, J=6 Hz),
1.1-1.8 (5H, m),
2.32 (3H, s), 2.5-3.1 (2H, m),
3.87 (3H, s), 3.9-4.7 (2H, m),
6.79 (1H, d, J=16 Hz),
7.01 (1H, d, J=8 Hz),
7.07 (1H, d, J=2 Hz),
7.11 (1H, dd, J=6, 2 Hz),
7.55 (1H, d, J=16 Hz)
MS (M+): 317
HRMS (C$_{18}$H$_{23}$NO$_4$):
Theoretical value: 317.16277.
Measured value: 317.16327.

EXAMPLE 56

Hydrolysis and Conversion into Non-toxic Salt

Using 5.2 g of 1-(4-acetoxy-3-methoxycinnamoyl)-4-methylpiperidine (Example 55), 70 ml of methanol, and 5 g of potassium carbonate, a reaction similar to that conducted in Example 54 was carried out. As a result, 3.4 g of 1-(4-hydroxy-3-methoxycinnamoyl)-4-methylpiperidine (a compound of the present invention) was obtained as a yellow oil, which had the following physiochemical properties:

Proton nuclear magnetic resonance
spectrum (δ ppm in CDCl$_3$):
0.95 (3H, d, J=6 Hz),
1.1–1.8 (5H, m),
2.6–3.2 (2H, m), 3.92 (3H, s),
4.12 (1H, m), 4.68 (1H, m),
6.27 (1H, br),
6.70 (1H, d, J=16 Hz),
6.78 (1H, d, J=8 Hz),
6.98 (1H, d, J=2 Hz),
7.06 (1H, dd, J=6, 2 Hz),
7.54 (1H, d, J=16 Hz)
MS (M+): 275
HRMS (C$_{16}$H$_{21}$NO$_3$):
Theoretical value: 275.15203.
Measured value: 275.15163.

The compound described above was reacted in the ordinary method, converting it into sodium 1-(3-methoxy-4-oxidecinnamoyl)-4-methylpiperidine, which had the following physiochemical properties:
Melting point: 251.1°–253.1° C.
Proton nuclear magnetic resonance
spectrum (δ ppm in D$_2$O):
0.90 (3H, d, J=6 Hz),
0.9–1.8 (5H, m),
2.6–3.2 (2H, m), 3.68 (1H, m),
3.81 (3H, s), 4.0–4.4 (2H, m),
6.61 (1H, d, J=8 Hz),
6.71 (1H, d, J=16 Hz), 7.12(1H, s),
7.07 (1H, d, J=8 Hz),
7.39 (1H, d, J=16 Hz)
MS [(M+H)+]: 298
HRMS (C$_{16}$H$_{21}$NO$_3$Na):
Theoretical value: 298.14194.
Measured value: 298.14150.

EXAMPLE 57

Esterification and Amidation

Using 3 g of 4-acetoxy-3-methoxycinnamoyl chloride, 1.4 ml of cyclohexylamine, and 100 ml of pyridine, a reaction similar to that conducted in Example 53 was carried out. As a result, 2.64 g of N-cyclohexyl-4-acetoxy-3-methoxycinnamamide (a compound of the present invention) was obtained as white crystal, which had the following physiochemical properties:
Melting point: 173.8°–174.2° C.
Proton nuclear magnetic resonance
spectrum (δ ppm in CDCl$_3$):
1.1–2.1 (10H, m), 2.32 (3H, s),
3.08 (1H, br), 3.09 (3H, s),
5.49 (1H, m),
6.26 (1H, d, J=16 Hz),
7.0–7.2 (3H, m),
7.52 (1H, d, J=16 Hz)
IR$_{max}$ (nujol, cm$^{-1}$): 3288, 1762, 1616
MS (M+): 317

EXAMPLE 58

Hydrolysis and Conversion into Non-toxic Salt

Using 2.64 g of N-cyclohexyl-4-acetoxy-3-methoxycinnamamide (Example 57), 70 ml of methanol, and 5 g of potassium carbonate, a reaction similar to that conducted in Example 54 was carried out. As a result, 2.32 g of N-cyclohexyl-4-hydroxy-3-methoxycinnamamide (a compound of the present invention) was obtained as white crystal, which had the following physiochemical properties:

Melting point: 173.8°–174.2° C.
Proton nuclear magnetic resonance
spectrum (δ ppm in CDCl$_3$):
1.1–2.1 (10H, m), 3.90 (1H, br),
3.91 (3H, s), 5.48 (1H, m),
5.83 (1H, s),
6.18 (1H, d, J=16 Hz),
6.88 (1H, d, J=8 Hz),
6.98 (1H, d, J=2 Hz),
7.03 (1H, dd, J=6, 2 Hz),
7.49 (1H, d, J=16 Hz)
IR$_{max}$ (KBr, cm$^{-1}$): 3440, 2936, 1652, 1620
MS (M+): 275

The compound described above was reacted in the ordinary method, converting it into sodium N-cyclohexyl-methoxy-4-oxidocinnamamide, which had the following physiochemical properties:
Proton nuclear magnetic resonance
spectrum (δ ppm in D$_2$O):
1.0–1.9 (10H, m), 3.64 (1H, m),
3.80 (3H, s),
6.23 (1H, d, J=16 Hz),
6.60 (1H, d, J=8 Hz),
7.06 (1H, d, J=8 Hz),
7.09 (1H, s), 7.35 (1H, d, J=16 Hz)
MS [(M+H)+]: 298
HRMS (C$_{16}$H$_{21}$NO$_3$Na):
Theoretical value: 298.14194.
Measured value: 298.14190.

EXAMPLE 59

Esterification and Amidation

Using 2.5 g of 4-acetoxy-3-methoxycinnamoyl chloride, 3.7 g of ethyl 4-amino-1-cyclohexanecarboxylate described in the literature [V. Skaric, M. Kovacevic, and D. Skaric, J. Chem. Soc. Perkin I, 1199–1201 (1976)], and 100 ml of pyridine, a reaction similar to that conducted in Example 53 was carried out. As a result, 2.3 g of ethyl 4-(4-acetoxy-3-methoxycinnamamido)-1-cyclohexanecarboxylate (a compound of the present invention) was obtained as pale yellowish white crystal, which had the following physiochemical properties:
Melting point: 183.1°–184.1° C.
Proton nuclear magnetic resonance
spectrum (δ ppm in CDCl$_3$):
1.22 (3/3H, t, J=7 Hz),
1.23 (6/3H, t, J=7 Hz),
1.4–2.5 (9H, m), 2.32 (3H, s),
3.84 (3/3H, s), 3.86 (6/3H, s),
3.8–4.0 (1H, m),
4.08 (⅔H, q, J=7 Hz),
4.10 (4/3H, q, J=7 Hz)
5.49 (⅓H, m), 5.66 (⅔H, m),
6.25 (⅓H, d, J=16 Hz),
6.28 (⅔H, d, J=16 Hz),
6.9–7.1 (3H, m),
7.52 (1H, d, J=16 Hz)
IR$_{max}$ (KBr, cm$^{-1}$): 3268, 2940, 1762, 1720, 1656, 1614
MS (M+): 389
Elemental analysis (C$_{21}$H$_{37}$NO$_6$):
Theoretical value; C: 64.76, H: 6.99, N: 3.60.
Measured value; C: 64.41, H: 6.99, N: 3.91.

EXAMPLE 60

Hydrolysis and Conversion into Non-toxic Salt 30 ml of methanol and 50 ml of 3N aqueous sodium hydroxide solution were added to 2.3 g of ethyl 4-(4-acetoxy-3-methoxycinnamamido)-1-cyclohexanecarboxylate (Example 59). The solution was reacted for 2 hours, while it was refluxed.

After reaction, 2N hydrochloric acid was added to the reaction solution, acidifying the solution. The solution was extracted three times with 50 ml of ethyl acetate. The organic layer obtained was washed twice with an aqueous sodium chloride solution and dried over magnesium sulfate. The solvent was removed in vacuo. The resultant product was recrystallized from ethyl acetate/hexane, yielding 1.12 g of 4-(4-hydroxy-3-methoxycinnamamido)-1-cyclohexanecarboxylic acid (a compound of this invention) as white crystal, which had the following physiochemical properties:

Melting point: 271.3°–271.9° C.
Proton nuclear magnetic resonance
spectrum ($\delta$ ppm in DMSO-$d_6$):
1.0–2.2 (9H, m),
3.33 ($\frac{2}{3}$H, br s), 3.58 ($\frac{1}{3}$H, m),
3.81 (3H, s),
6.38 (1H, d, J=16 Hz),
6.77 (1H, d, J=8 Hz),
6.94 (1H, d, J=8 Hz), 7.08 (1H, s),
7.34 (1H, d, J=16 Hz),
7.82 (1H, d, J=8 Hz), 9.28 (1H, br),
11.97 (1H, br)
$IR_{max}$ (KBr, $cm^{-1}$): 3448, 2948, 1692, 1650, 1618
MS (M+): 319

The compound described above was reacted in the ordinary method, converting it into disodium 4-(3-methoxy-4-oxidocinnamamido)-1-cyclohexanecarboxylate, which had the following physiochemical properties:

Proton nuclear magnetic resonance
spectrum ($\delta$ ppm in $D_2O$):
1.2–2.2 (9H, m), 3.67 (1H, m),
3.81 (3H, s),
6.24 (1H, d, J=16 Hz),
6.62 (1H, d, J=8 Hz),
7.07 (1H, d, J=8 Hz), 7.11 (1H, s),
7.36 (1H, d, J=16 Hz)
MS [(M+H)+]: 364
HRMS ($C_{17}H_{20}NO_5Na_2$):
Theoretical value: 364.11375.
Measured value: 364.11490.

EXAMPLE 61

Esterification and Amidation

Using 5.09 g of 4-acetoxy-3-methoxycinnamoyl chloride, 2.98 g of 4-methylcyclohexylamine hydrochloride, and 100 ml of pyridine, a reaction similar to that conducted in Example 53 was carried out. As a result, 4.31 g of N-(4-methylcyclohexyl)-4-acetoxy-3-methoxycinnamamide was obtained as yellowish white crystal, which had the following physiochemical properties:

Melting point: 193.5°–194.3° C.
Proton nuclear magnetic resonance
spectrum ($\delta$ ppm in DMSO-$d_6$):
0.89 (12/5H, d, J=6 Hz),
0.93 (3/5H, d, J=6 Hz),
1.0–2.1 (9H, m), 2.32 (3H, s)
3.83 (12/5H, br), 3.85 (3/5H,
3.86 (12/5H, s), 4.12 (1/5H, br),
5.46 (4/5H, m), 5.69 (1/5H, m),
6.25 (4/5H, d, J=16 Hz),
6.30 (1/5H, d, J=16 Hz),
6.9–7.1 (3H, m),
7.51 (4/5H, d, J=16 Hz),
7.53 (1/5H, d, J=16 Hz)
$IR_{max}$ (KBr, $cm^{-1}$): 3284, 2936, 1766 1656
MS (M+): 331
Elemental analysis ($C_{19}H_{25}NO_4$)
Theoretical value; C: 68.86, H: 7.60, N: 4.23.
Measured value; C: 68.81, H: 7.41, N: 4.25.

EXAMPLE 62

Hydrolysis and Conversion into Non-toxic Salt

Using 4.31 g of N-(4-methylcyclohexyl)-4-acetoxymethoxycinnamamide (Example 61), 100 ml of methanol, and 10 g of potassium carbonate, a reaction similar to that conducted in Example 54 was carried out. As a result, 3.14 g of N-(4-methylcyclohexyl)-4-hydroxy-3-methoxycinnamamide (a compound of the present invention) was obtained as pale yellowish white crystal, which had the following physiochemical properties:

Melting point: 205.6°–206.2° C.
Proton nuclear magnetic resonance
spectrum ($\delta$ ppm in DMSO-$d_6$):
0.86 (12/5H, d, J=8 Hz),
0.90 (3/5H, d, J=8 Hz),
1.0–1.9 (9H, m), 3.56 (4/5H, m),
3.80 (12/5H, s), 3.82 (3/5H, s),
3.91 (1/5H, m),
6.37 (4/5H, d, J=16 Hz),
6.53 (1/5H, d, J=16 Hz),
6.7–7.1 (3H, m),
7.25 (4/5H, d, J=16 Hz),
7.26 (1/5H, d, J=16 Hz),
7.74 (1/5H, d, J=8 Hz),
7.75 (4/5H, d, J=8 Hz),
9.35 (1H, s)
$IR_{max}$ (KBr, $cm^{-1}$): 3252, 2924, 1650
MS (M+): 289
Elemental analysis ($C_{17}H_{23}NO_3$)
Theoretical value; C: 70.56, H: 8.01, N: 4.84.
Measured value; C: 70.60, H: 7.96, N: 5.04.

The compound described above was reacted in the ordinary method, converting it into sodium N-(4-methylcyclohexyl)-3-methoxy-4-oxidocinnamamide, which had the following physiochemical properties:

Melting point: 233.6°–235.8° C.
Proton nuclear magnetic resonance
spectrum ($\delta$ ppm in $D_2O$):
0.84 (12/5H, d, J=6 Hz),
0.86 (3/5H, d, J=6 Hz),
0.9 2.0 (9H, m), 3.58 (4/5H, m),
3.80 (12/5H, s), 3.81 (3/5H,
3.89 (1/5H, m),
6.23 (4/5H, d, J=16 Hz),
6.38 (1/5H, d, J=16 Hz),
6.6 7.1 (3H, m),
7.35 (4/5H, d, J=16 Hz),
7.42 (1/5H, d, J=16 Hz),
7.71 (1/5H, d, J=8 Hz),
7.73 (4/5H, d, J=8 Hz)
MS [(M+H)+]: 312
HRMS ($C_{17}H_{23}NO_3Na$):
Theoretical value: 312.15759.
Measured value: 312.15480.

EXAMPLE 63

Esterification and Amidation

Using 8.9 g of 4-acetoxy-3-methoxycinnamoyl chloride, 3.81 g of 4,4-dimethyl-1-cyclohexylamine, and 100 ml of pyridine, a reaction similar to that conducted in Example 53 was carried out. As a result, 8.99 g of N-(4,4-dimethylcyclohexyl)-4-acetoxy-3-methoxycinnamamide (a compound of the present invention) was obtained as white crystal, which had the following physiochemical properties:

Melting point: 206.9°–207.5° C.
Proton nuclear magnetic resonance
spectrum ($\delta$ ppm in $CDCl_3$):
0.93 (6H, s), 1.2–1.9 (8H, m),
2.32 (3H, s), 3.84 (1H, br),
3.85 (3H, s), 5.52 (1H, m),
6.27 (1H, d, J=16 Hz),
7.0–7.2 (3H, m),
7.52 (1H, d, J=16 Hz)
$IR_{max}$ (KBr, $cm^{-1}$): 3288, 2936, 1762, 1652
MS ($M^+$): 345
Elemental analysis ($C_0H_{27}NO_4$):
Theoretical value; C: 69.54, H: 7.88, N: 4.05.
Measured value; C: 69.66, H: 7.90, N: 4.33.

EXAMPLE 64

Hydrolysis and Conversion into Non-toxic Salts

Using 8.99 g of N-(4,4-dimethylcyclohexyl)-acetoxy-3-methoxycinnamamide (Example 63), 100 ml of methanol, and 10 g of potassium carbonate, a reaction similar to that conducted in Example 54 was carried out. As a result, 7.34 g of N-(4,4-dimethylcyclohexyl)-4-hydroxy-3-methoxycinnamamide (a compound of the present invention) was obtained as white crystal, which had the following physiochemical properties:

Melting point: 208.0°–208.9° C.
Proton nuclear magnetic resonance
spectrum ($\delta$ ppm in $DMSO-d_6$):
0.91 (6H, s), 1.1–1.7 (8H, m),
3.61 (1H, br), 3.81 (3H, s),
6.39 (1H, d, J=16 Hz),
6.76 (1H, d, J=8 Hz),
6.94 (1H, dd, J=6, 2 Hz),
7.09 (1H, d, J=2 Hz),
7.33 (1H, d, J=16 Hz),
7.78 (1H, d, J=8 Hz), 9.36 (1H, brs)
$IR_{max}$ (KBr, $cm^{-1}$): 3304, 2944, 1660
MS ($M^+$): 303
Elemental analysis ($C_{18}H_{25}NO_3$):
Theoretical value; C: 71.26, H: 8.31, N: 4.62.
Measured value; C: 70.83, H: 8.30, N: 4.94.

The compound described above was reacted in the ordinary method, converting it into sodium N-(4,4-dimethylcyclohexyl)-3-methoxy-4-oxidocinnamamide, which had the following physiochemical properties:

Proton nuclear magnetic resonance
spectrum ($\delta$ ppm in $D_2O$):
0.89 (6H, s), 1.0–1.7 (8H, m),
3.60 (1H, m), 3.80 (3H, s),
6.35 (1H, d, J=16 Hz),
6.71 (1H, d, J=8 Hz),
6.90 (1H, d, J=8 Hz), 7.05 (1H, s),
7.30 (1H, d, J=16 Hz)
MS [(M+H)$^+$]: 326
HRMS ($C_{18}H_{25}NO_3Na$):
Theoretical value: 326.17324.
Measured value: 326.17140.

EXAMPLE 65

Esterification and Amidation, and Hydrolysis and Conversion into Non-toxic Salt 8.1 g of 4-acetoxy-3-methoxycinnamoyl chloride and 15 g of 4-piperidinecarboxylic acid were added to 200 ml of saturated aqueous potassium carbonate. The solution was stirred for 4 hours at room temperature. After reaction, 2N hydrochloric acid was added to the reaction solution, acidifying the solution. 50 ml of ethyl acetate was added to the solution, and the solution was stirred for 1 hour. The crystal precipitated was filtered out and recrystallized from ethyl acetate/hexane, yielding 5.4 g of 1-(4-hydroxy-3-methoxycinnamoyl)piperidine-4-carboxylic acid (a compound of the present invention) as white crystal, which had the following physiochemical properties:

Melting point: 182.2°–182.8° C.
Proton nuclear magnetic resonance
spectrum ($\delta$ ppm in $CD_3OD$):
1.6–2.2 (4H, m), 2.6–3.5 (3H, m),
3.91 (3H, s), 4.1–4.6 (2H, m),
6.79 (1H, d, J=8 Hz),
6.90 (1H, d, J=16 Hz),
7.05 (1H, dd, 8, 2 Hz),
7.19 (1H, d, J=2 Hz),
7.47 (1H, d, J=16 Hz)
$IR_{max}$ (KBr, $cm^{-1}$): 3260, 1730, 1640, 1604
MS ($M^+$): 305
Elemental analysis ($C_{16}H_{19}NO_5$):
Theoretical value; C: 62.94, H: 6.27, N: 4.59.
Measured value; C: 62.85, H: 6.20, N: 4.87.

The compound described above was reacted in the ordinary method, converting it into disodium 1-(3-oxido-4-methoxycinnamoyl)piperidine-4-carboxylate, which had the following physiochemical properties:

Melting point: 243.8°–246.5° C.
Proton nuclear magnetic resonance
spectrum ($\delta$ ppm in $D_2O$):
1.4–3.4 (7H, m), 3.71 (1H, m),
3.84 (3H, s), 4.1–4.5 (2H, m),
6.68 (1H, d, J=8 Hz),
6.78 (1H, d, J=16 Hz),
7.10 (1H, d, J=8 Hz), 7.17 (1H, s),
7.42 (1H, d, J=16 Hz)
MS [(M+H)$^+$]350
HRMS ($C_{16}H_{18}NO_5Na_2$):
Theoretical value: 350.09810.
Measured value: 350.10150.

EXAMPLE 66

Esterification and Amidation

A solution of 6.9 g of 1-(4-hydroxy-3-methoxycinnamoyl)piperidine-4-carboxylic acid (Example 65), 10 g of potassium carbonate and 6.5 ml of allyl bromide, mixed in 250 ml of DMF, was reacted for 7 hours at room temperature. After reaction, 400 ml of an aqueous sodium chloride solution was added to the reaction solution. The solution was extracted three times with 100 ml of ethyl acetate. The organic layer obtained was washed twice with an aqueous sodium chloride solution and dried over magnesium sulfate. Thereafter, the solvent was removed in vacuo. The oily substance obtained was subjected to column chromatography using 100 g of silica gel. From the fraction eluted with hexane and ethyl acetate =3:2, the solvent was removed in vacuo, yielding 7.8 g of allyl 1-(4-allyloxy-3-methoxycinnamoyl)piperidine-4-carboxylate (a compound of the present invention) as a pale yellow oil, which had the following physiochemical properties:

Proton nuclear magnetic resonance spectrum ($\delta$ ppm in $CDCl_3$):
1.6–2.1 (6H, m), 2.5–3.3 (3H, m),
3.92 (3H, s), 4.6–4.7 (4H, m),
5.2–5.5 (4H, m), 5.8–6.2 (2H, m),
6.70 (1H, d, J=16 Hz),
6.84 (1H, d, J=8 Hz),
7.0–7.2 (2H, m),
7.56 (1H, d, J=16 Hz)
MS (M+): 385
HRMS ($C_{22}H_{27}NO_3$):
Theoretical value: 385.18883.
Measured value: 385.18883.

EXAMPLE 67

Alkylation 50 ml of sodium hexamethyldisilazide (1M solution in THF) and 5.3 ml of methyl iodide were added to a solution of 7.8 g of allyl 1-(4-allyloxy-3-methoxycinnamoyl)-piperidine-4-carboxylate (Example 66) in 200 ml of THF. The solution was reacted for 18 hours at room temperature. After reaction, 200 ml of an aqueous ammonium chloride solution was added to the reaction solution. The solution was extracted three times with 100 ml of ethyl acetate. The organic layer obtained was washed twice with an aqueous sodium chloride solution and dried over magnesium sulfate. Thereafter, the solvent was removed in vacuo. The oily substance obtained was subjected to column chromatography using 100 g of silica gel. From the fraction eluted with hexane and ethyl acetate=3:2, the solvent was removed in vacuo, yielding 1.1 g of allyl 1-(4-allyloxy-3-methoxycinnamoyl)-4-methylpiperidine-4-carboxylate (a compound of the present invention) as a pale yellow oil, which had the following physiochemical properties:

Proton nuclear magnetic resonance spectrum ($\delta$ ppm in $CDCl_3$):
1.25 (3H, s), 1.3–1.8 (4H, m),
2.2–3.2 (3H, m), 3.8–4.2 (2H, m),
3.91 (3H, s), 5.7 (1H, m),
6.67 (1H, d, J=16 Hz),
6.87 (1H, d, J=8 Hz), 7.05 (1H, s),
7.11 (1H, d, J=8 Hz),
7.68 (1H, d, J=16 Hz)
MS (M+): 399

EXAMPLE 68

Reduction and Conversion into Non-toxic Salt 0.4 g of bis(triphenylphosphine)palladium dichloride and 5 g of ammonium formate were added to a solution of 1.1 g of allyl 1-(4-allyloxy-3-methoxycinnamoyl)-4-methylpiperidine-4-carboxylate (Example 67) in 100 ml of THF. Under an argon stream, the solution was reacted for hours, while it was refluxed. After reaction, 150 ml of an aqueous sodium chloride solution was added to the reaction solution. The solution was extracted three times with 50 ml of ethyl acetate. The organic layer obtained was washed three times with an aqueous sodium chloride solution and dried over magnesium sulfate. Thereafter, the solvent was removed in vacuo, yielding 1.1 g of 1-(4-hydroxy-3-methoxycinnamoyl)-4-methylpiperidine-4-carboxylic acid (a compound of the present invention) as a pale yellow oil, which had the following physiochemical properties:

Proton nuclear magnetic resonance spectrum ($\delta$ ppm in $CDCl_3$):
1.26 (3H, s), 1.3–2.3 (4H, m),
2.9–3.4 (3H, m), 3.8–4.4 (2H, m),
3.93 (3H, s), 5.78 (1H, m),
6.68 (1H, d, J=16 Hz),
6.89 (1H, d, J=8 Hz),
6.99 (1H, d, J=2 Hz),
7.07 (1H, dd, J=6, 2 Hz)
MS (M+): 319
HRMS ($C_{17}H_{21}NO_5$):
Theoretical value: 319.14191.
Measured value: 319.14111.

The compound described above was reacted in the ordinary method, converting it into disodium 1-(3-methoxy-4-oxidocinnamoyl)-4-methylpiperidine-4-carboxylate, which had the following physiochemical properties:

Proton nuclear magnetic resonance spectrum ($\delta$ ppm in $D_2O$):
1.0–2.2 (4H, m), 3.0–3.6 (2H, m),
3.70 (1H, m), 3.83 (3H, s),
3.8–4.1 (2H, m),
6.58 (1H, d, J=8 Hz),
6.75 (1H, d, J=16 Hz),
7.09 (1H, d, J=8 Hz), 7.29 (1H, s),
7.35 (1H, d, J=16 Hz)
MS [(M+H)+]: 364
HRMS ($C_{17}H_{20}NO_5Na_2$):
Theoretical value: 364.11375.
Measured value: 364.11150.

EXAMPLE 69

Convertion into Imine

A solution prepared by mixing 5.6 g of 4-methylcyclohexanone, 5.35 g of benzylamine, and 50 ml of benzene was reacted, while it was refluxed. The water formed during the reaction was removed from the system by using a Dean-Stark trap. The reaction was performed for 8 hours.

After reaction, the solvent was removed in vacuo, yielding 8.6 g of N-benzyl-4-methylcyclohexaneimine as a colorless oil, which had the following physiochemical properties:

Proton nuclear magnetic resonance spectrum ($\delta$ ppm in $CDCl_3$):
0.95 (3H, d, J=6 Hz),
1.0–2.9 (9H, m),
4.54 (2H, s), 7.1–7.5 (5H, m)
MS (M+): 201
HRMS ($C_{14}H_{19}N$):
Theoretical value: 201.15175.
Measured value: 201.14189.

EXAMPLE 70

Reduction and Hydrolysis 2 g of sodium borohydride was added to a solution of 8.6 g of N-benzyl-4-methylcyclohexaneimine (Example 69) in 50 ml of methanol. The solution was reacted for 2 hours, while it was refluxed.

After reaction, 10 ml of 2N hydrochloric acid was added to the reaction solution under ice-cooling, and 10 ml of ammonia water and 100 ml of 2N aqueous sodium chloride solution were added. The solution was extracted three times with 30 ml of methylene chloride.

The organic layer obtained was washed with an aqueous sodium chloride solution and dried over magnesium sulfate. Thereafter, the solvent was removed in vacuo, yielding 7.1 g of N-benzyl-4-methylcyclohexylamine which was a mixture of cis and trans =about 1:4 and which had the following physiochemical properties:
Proton nuclear magnetic resonance
spectrum (δ ppm in CDCl$_3$):
0.85 (9/4H, d, J=7 Hz),
0;91 (¾H, d, J=7 Hz ),
1.0–2.8 (9H, m), 3.7–3.9 (1H, m),
3.86 (2H, s), 7.2–7.4 (5H, m)
MS (M+): 203

EXAMPLE 71
Reduction 0.1 g of 20% palladium hydroxide-carbon was added to a solution of 7.1 g of N-benzyl-4-methylcyclohexylamine (Example 70) in 50 ml of methanol. Under normal-pressure hydrogen gas, the solution was vigorously stirred for 18 hours. After reaction, the catalyst was filtered out, and hydrogen chloride gas was blown into the filtrate. Thereafter, the methanol was removed in vacuo, yielding 4.5 g of 4-methylcyclohexylammonium chloride which was a mixture of cis and trans =about 1:4 and which had the following physiochemical properties:
Proton nuclear magnetic resonance
spectrum (δ ppm in CDCl$_3$):
0.83 (12/5H, d, J=6 Hz),
0.97 (3/5H, d, J=6 Hz),
0.9–2.2 (11H, m), 3.08 (4/5H, m),
3.39 (1/5H, m)
MS (M+): 149

EXAMPLE 72
Refining 4-methylcyclohexylammonium chloride (Example 71) was suspended in 4 ml of methylene chloride cooled. The crystal obtained was filtered out, yielding 3.2 g of trans-4-methylcyclohexylammonium chloride as white crystal, which had the following physiochemical properties:
Proton nuclear magnetic resonance
spectrum (δ ppm in CDCl$_3$):
0.87 (3H, d, J=6 Hz),
0.9–2.2 (9H, m), 3.0–3.2 (1H, m),
8.22 (2H, br)
MS [(M-Cl)$^{30}$]: 114

EXAMPLE 73
Esterification and Amidation 21 g of 4-dimethylaminobutyric acid hydrochloride was added, under ice-cooling, to a solution of 16 ml of diethyl chlorophosphate, 72 ml of triethylamine and 250 ml of methylene chloride. Then, the solution was restored to room temperature, and stirred for 1 hour. Thereafter, 22 g of trans-4-methylcyclohexylammonium chloride (Example 72), and 0.6 g of 4-dimethylaminopyridine were added to the solution.

After the addition, the solution was restored to room temperature, and was reacted for 6 hours. After reaction, the reaction solution was washed five times with 300 ml of an aqueous sodium hydrogencarbonate. The organic layer obtained was dried over magnesium sulfate. Thereafter, the solvent was removed in vacuo, yielding 13.1 g of N-(trans-4-methylcyclohexyl)-4-dimethylaminobutylamide as white crystal, which had the following physiochemical properties:
Proton nuclear magnetic resonance
spectrum (δ ppm in CDCl$_3$):
0.87 (3H, d, J=6 Hz ),
0.9–2.0 (13H, m), 2.21 (6H, s),
2.27 (2H, t, J=7 Hz), 3.68 (1H, m)
MS [(M+H)+]: 199

EXAMPLE 74
Reduction 13.1 g of N-(trans-4-methylcyclohexyl ) -4-dimethylaminobutylamide (Example 73) was dissolved in 100 ml of THF. Under an argon stream, the solution was added dropwise to a solution of 7.5 g of lithium aluminum hydride suspended in 400 ml of THF under ice-cooling. After the addition, the solution was reacted for 8 hours, while it was refluxed. After reaction, the solution was allowed to cool to room temperature. Then, 22 g of sodium sulfate decahydrate was added to the solution under ice-cooling. The solution was stirred for 1 hour, and the precipitate was filtered out. The solvent was removed in vacuo, yielding an oily substance. This substance was subjected to vacuum distillation, yielding 5.7 g of N-(4-dimethylaminobutyl)-trans-4-methylcyclohexylamine as a colorless oil, which had the following physiochemical properties:
Boiling point: 78°–79.5° C./0.5 mmHg
Proton nuclear magnetic resonance
spectrum (δ ppm in CDCl$_3$):
0.86 (3H, d, J=7 Hz),
0.8–2.4 (16H, m), 2.21 (6H, s),
2.63 (2H, br)
MS [(M+H)+]: 213

EXAMPLE 75
Esterification and Amidation, and Hydrolysis and Conversion into Non-toxic Salt A mixture solution of 2.8 ml of diethyl chlorophosphate, 2.7 ml of triethylamine, 2.3 g of 4-acetoxy-3-methoxycinnamic acid, and 100 ml of methylene chloride was stirred for 1 hour at room temperature. Next, 3.5 ml of N-(4-dimethylaminobutyl)-trans-4-methylcyclohexylamine (Example 74) and 0.5 g of 4-dimethylaminopyridine were added to the solution under ice-cooling. The solution was stirred further for 4 hours at room temperature. Then, 100 ml of methanol and 5 g of potassium carbonate were added to the solution, and the solution was stirred for 1.5 hours at room temperature. After stirring, the reaction solution was neutralized with 2N hydrochloric acid under ice-cooling. The solution was extracted three times with 50 ml of ethyl acetate. The organic layer obtained was washed twice with an aqueous sodium hydrogencarbonate solution and twice with aqueous sodium chloride solution, and was dried over magnesium sulfate. Thereafter, the solvent was removed in vacuo. The product obtained was recrystallized from methylene chloride/either, yielding 1.7 g of N-(4-dimethylaminobutyl)-N-(trans-4-methylcyclohexyl)-4-hydroxy-3-methoxycinnamamide (a compound of the present this invention) as a pale yellow oily oil, which had the following physiochemical properties:
Proton nuclear magnetic resonance
spectrum (δ ppm in CDCl$_3$):
0.89 (3H, d, J=6 Hz),
0.9–1.9 (13H, m), 2.24 (6H, s), 2.28 (2H, t, J=7 Hz),
3.22 (2H, t, J=7 Hz), 3.66 (1H, m),
3.91 (3H, s),
6.71 (1H, d, J=16 Hz),
6.9-7.1 (3H, m),
7.58 (1H, d, J=16 Hz)
MS [(M+H)+]: 389
HRMS ($C_{23}H_{37}N_2O_3$):
Theoretical value: 389.28042.
Measured value: 389.28110.

The compound described above was reacted in the ordinary method, converting it into N-(4-dimethylaminobutyl)-N-(trans-4-methylcyclohexyl)-4-hydroxy-3-methoxycinnamamide hydrochloride, which had the following physiochemical properties:
Proton nuclear magnetic resonance spectrum ($\delta$ ppm in $D_2O$):
0.89 (3H, d, J=6 Hz),
0.9-1.9 (13H, m),
2.51 (2H, t, J=7 Hz), 3.09 (6H, s),
3.61 (2H, t, J=7 Hz), 3.65 (1H, m),
3.90 (3H, s),
6.63 (1H, d, J=16 Hz),
6.8-7.1 (3H, m),
7.51 (1H, d, J=16 Hz)
MS [(M-Cl)+]: 389
HRMS ($C_{23}H_{37}N_2O_3$):
Theoretical value: 389.28042.
Measured value: 389.28057.

EXAMPLE 76

Reduction and Conversion into Non-toxic Salt 0.05 g of 10% palladium-carbon was added to a solution of 1 g of N-(4-dimethylaminobutyl)-N-(trans-4-methylcyclohexyl)-4-hydroxy-3-methoxycinnamamide (Example 75) in 60 ml of methanol. Under normal-pressure hydrogen gas, the solution was reacted for 16 hours, while it was vigorously stirred. After reaction, the catalyst was filtered out, and the solvent was removed in vacuo from the filtrate, yielding 0.92 g of N-(4-dimethylaminobutyl)-N-(trans-4-methylcyclohexyl)-3-(4-hydroxy-3-methoxyphenyl)propionamide (a compound of the present invention) as a pale yellow oily oil, which had the following physiochemical properties:
Proton nuclear magnetic resonance spectrum ($\delta$ ppm in $CDCl_3$):
0.86 (3H, d, J=6 Hz),
0.9-1.9 (13H, m), 2.30 (6H, s),
2.42 (2H, t, J=9 Hz),
2.64 (2H, t, J=7 Hz),
2.80 (2H, t, J=7 Hz),
3.28 (2H, t, J=7 Hz), 3.62 (1H, m),
3.79 (3H, s), 6.8-7.1 (3H, m)
MS [(M+H)+]: 391
HRMS ($C_{23}H_{39}N_2O_3$):
Theoretical value: 391.29603.
Measured value: 391.29607.

The compound described above was reacted in the ordinary method, converting it into N-(4-dimethylaminobutyl)-N-(trans-4-methylcyclohexyl)-3-(4-hydroxy-3-methoxyphenyl)propionamide hydrochloride, which had the following physiochemical properties:
Proton nuclear magnetic resonance spectrum ($\delta$ ppm in $D_2O$):
0.86 (3H, d, J=6 Hz),
0.9-1.9 (13H, m),
2.61 (2H, t, J=7 Hz),
2.98 (2H, t, J=7 Hz), 3.08 (6H, s),
3.26 (2H, t, J=7 Hz), 3.61 (1H, m),
3.76 (2H, t, J=7 Hz), 3.78 (3H, s),
6.7-7.1 (3H, m)
MS [(M-Cl)+]: 391
HRMS ($C_{23}H_{39}N_2O_3$):
Theoretical value: 391.29607.
Measured value: 391.29479.

EXAMPLE 77

Esterification and Amidation

Under ice-cooling, 10.4 g of dimethylaminoglycine hydrochloride was added to a solution of 13 ml of diethyl chlorophosphate, 36 ml of triethylamine, and 100 ml of methylene chloride. Thereafter, the solution was restored to room temperature and stirred for 1 hour. After 1 hour, 18 g of trans-4-methylcyclohexylammonium chloride and 0.3 g of 4-dimethylaminopyridine were added to the solution.

After the addition, the solution was restored to room temperature, and the reaction was continued for 6 hours. After reaction, the reaction solution was washed five times with 200 ml of an aqueous sodium hydrogencarbonate. The organic layer obtained was dried over magnesium sulfate. The solvent was removed in vacuo, yielding 8.5 g of N-(trans-4-methylcyclohexyl)-2-dimethylaminoacetamide as white crystal, which had the following physiochemical properties:
Proton nuclear magnetic resonance spectrum ($\delta$ ppm in $CDCl_3$):
0.88 (3H, d, J=6 Hz ),
1.0-2.0 (9H, m),
2.28 (3H, s), 2.92 (2H, s),
3.71 (1H, m)
MS [(M+H)+]: 199
HRMS ($C_{11}H_{23}N_2O$):
Theoretical value: 199.18104.
Measured value: 199.18206.

EXAMPLE 78

Reduction 8.5 g of N-(trans-4-methylcyclohexyl)-2-dimethylaminoacetamide was dissolved in 100 ml of THF. Under an argon stream, the solution was added dropwise to a solution of 3.6 g of lithium aluminum hydride suspended in 200 ml of THF under ice-cooling. After the addition, the solution was reacted for 8 hours, while it was refluxed. After reaction, the solution was allowed to cool to room temperature. Then, 10 g of sodium sulfate decahydrate was added to the solution under ice-cooling. The solution was stirred for 1 hour, and the precipitate was filtered out. The solvent was removed in vacuo to obtaine an oily substance. This substance was refined by vacuum distillation, yielding 3.8 g of N-(2-dimethylaminoethyl)-trans-4-methylcyclohexylamine as a colorless oil, which had the following physiochemical properties:
Boiling point: 78.0°-79.5° C./0.5 mmHg
Proton nuclear magnetic resonance spectrum ($\delta$ ppm in $CDCl_3$):
0.85 (3H, d, J=6 Hz ),
0.9-2.0 (9H, m), 2.22 (6H, s),
2.36 (2H, t, J=7 Hz),
2.64 (2H, t, J=7 Hz)
MS [(M+H)+] 185

HRMS ($C_{11}H_{25}N_2$):
Theoretical value: 185.20177.
Measured value: 185.20212.

EXAMPLE 79

Esterification and Amidation, and Hydrolysis and Conversion into Non-toxic Salt

Using 2.5 g of 4-acetoxy-3-methoxycinnamic acid, 2.8 ml of diethyl chlorophosphate, 2.7 ml of triethylamine, 100 ml of methylene chloride, 3 ml of N-(2-dimethylaminoethyl)-trans-4-methylcyclohexylamine (Example 78), 0.5 g of 4-dimethylaminopyridine, 100 ml of methanol, and 3 g of potassium carbonate, a reaction similar to that conducted in Example 73 was carried out. As a result, 1.8 g of N-(2-dimethylaminoethyl)-N-(trans-4-methylcyclohexyl)-4-hydroxy-3-methoxycinnamamide (a compound of the present invention) was obtained as white crystal, which had the following physiochemical properties:

Proton nuclear magnetic resonance
spectrum ($\delta$ ppm in $CDCl_3$):
0.87 (3H, d, J=6 Hz),
0.9–1.8 (9H, m), 2.39 (6H, s),
2.49 (2H, t, J=7 Hz),
3.42 (2H, t, J=7 Hz), 3.72 (1H, m),
3.82 (3H, s),
6.81 (1H, d, J=16 Hz),
7.1–7.3 (3H, m),
7.37 (1H, d, J=16 Hz)
MS [(M+H)+] 361
HRMS ($C_{21}H_{32}N_2O_3$):
Theoretical value: 361.24129.
Measured value: 316.24910.

The compound described above was reacted in the ordinary method, converting it into N-(2-dimethylaminoethyl)-N-(trans-4-methylcyclohexyl)-4-hydroxy-3-methoxycinnamamide hydrochloride, which had the following physiochemical properties:

Proton nuclear magnetic resonance
spectrum ($\delta$ ppm in $D_2O$):
0.87 (3H, d, J=6 Hz),
0.9–1.9 (9H, m),
2.89 (2H, t, J=7 Hz), 3.04 (6H, s),
3.71 (1H, m),
3.76 (2H, t, J=16 Hz),
3.83 (3H, s),
6.77 (1H, d, J=16 Hz),
7.0–7.73 (3H, m),
7.34 (1H, d, J=16 Hz)
MS [(M-Cl)+: 361
HRMS ($C_{21}H_{33}N_2O_3$):
Theoretical value: 361.24912.
Measured value: 361.24845.

EXAMPLE 80

Reduction and Conversion into a Non-toxic Salt 0.05 g of 10% palladium-carbon was added to a solution of 1 g of N-(2-dimethylaminoethyl)-N-(trans-4-methylcyclohexyl)-4-hydroxy-3-methoxycinnamamide (Example 79) in 60 ml of methanol. Under normal-pressure hydrogen gas, the solution was vigorously stirred. After 16 hours, the reaction was ceased, the catalyst was filtered out, and the solvent was removed in vacuo from the filtrate. The product obtained was recrystallized from methylene chloride/ether, yielding 0.94 g of N-(2-dimethylaminoethyl)-N-(trans-4-methylcyclohexyl)-3-(4-hydroxy-3-methoxyphenyl)propionamide (a compound of the present invention) as white crystal, which had the following physiochemical properties:

Proton nuclear magnetic resonance
spectrum ($\delta$ ppm in $CDCl_3$):
0.87 (3H, d, J=6 Hz),
0.9–1.8 (9H, m),
2.38 (6H, s), 2.48 (2H, t, J=7 Hz),
2.58 (2H, t, J=7 Hz),
2.71 (2H, t, J=7 Hz),
3.43 (2H, t, J=7 Hz), 3.71 (1H, m),
3.81 (3H, s), 6.79 (1H, m)
7.0–7.3 (3H, m)
MS [(M+H)+]: 363
HRMS ($C_{21}H_{35}N_2O_3$):
Theoretical value: 363.26477.
Measured value: 363.26474.

The compound described above was reacted in the ordinary method, converting it into N-(2-dimethylaminoethyl)-N-(trans-4-methylcyclohexyl)-3-(4-hydroxy-3-methoxyphenyl)propionamide hydrochloride, which had the following physiochemical properties:

Proton nuclear magnetic resonance
spectrum ($\delta$ ppm in $D_2O$):
0.87 (3H, d, J=6 Hz),
0.9–1.9 (9H, m),
2.58 (2H, t, J=7 Hz),
2.99 (2H, t, J=7 Hz), 3.06 (6H, s),
3.51 (2H, t, J=7 Hz), 3.68 (1H, m),
3.82 (3H, s), 4.21 (2H, t, J=7 Hz),
6.9–7.3 (3H, m)
MS [(M-Cl)+: 363
HRMS ($C_{21}H_{35}N_2O_3$):
Theoretical value: 363.26477.
Measured value: 363.26505.

EXAMPLE 81

Esterification and Amidation, and Conversion into Non-toxic Salt

A solution of 2.5 g of 3,4-methylenedioxycinnamic acid, 2.8 ml of diethyl chlorophosphate and 2.7 ml of triethylamine, mixed in 100 ml of methylene chloride was stirred for 1 hour at room temperature. Next, under ice cooling, 3 ml of N-(2-dimethylaminoethyl)-trans-4-methylcyclohexylamine (Example 78) and 0.5 g of 4-dimethylaminopyridine were added to the solution, and the solution was further stirred for 4 hours at room temperature.

After reaction, the reaction solution was washed five times with 200 ml of an aqueous sodium hydrogencarbonate and dried over magnesium sulfate. Thereafter, the solvent was removed in vacuo. The product obtained was recrystallized from methylene chloride/ether, yielding 1.86 g of N-(2-dimethylaminoethyl)-N-(trans-4-methylcyclohexyl)3,4-methylenedioxycinnamamide (a compound of the present invention) as white crystal, which had the following physiochemical properties:

Proton nuclear magnetic resonance
spectrum ($\delta$ ppm in $CDCl_3$):
0.89 (3H, d, J=6 Hz),
0.9–1.8 (9H, m),
2.32 (6H, s), 2.44 (2H, t, J=7 Hz),
3.43 (2H, t, J=7 Hz), 3.69 (1H, m),
6.00 (2H, s),
6.66 (1H, d, J=16 Hz),
6.78 (1H, d, J=8 Hz), 6.98 (1H, d, J=8 Hz), 7.02 (1H, s),
7.56 (1H, d, J=16 Hz)
MS [(M+H)+]: 375

The compound described above was reacted in the ordinary method, converting it into N-(2-dimethylaminoethyl)-N-(trans-4-methylcyclohexyl)-3,4-methylenedioxycinnamamide hydrochloride, which had the following physiochemical properties:
Proton nuclear magnetic resonance
spectrum ($\delta$ ppm in $D_2O$):
0.88 (3H, d, J=6 Hz),
0.9–1.9 (9H, m),
2.88 (2H, t, J=7 Hz), 3.02 (6H, s),
3.68 (1H, m), 3.81 (2H, t, J=7 Hz),
6.02 (1H, s),
6.63 (1H, d, J=16 Hz),
6.75 (1H, d, J=8 Hz),
6.9–7.1 (2H, m),
7.50 (1H, d, J=16 Hz)
MS [(M-Cl)+: 359
HRMS ($C_{21}H_{31}N_2O_3$):
Theoretical value: 359.23347.
Measured value: 359.23256.

EXAMPLE 82

Esterification and Amidation, and Hydrolysis and Conversion into Non-toxic Salt

Using 1 g of N-(2-dimethylaminoethyl)-N-(trans-4-methylcyclohexyl)-3,4-methylenedioxycinnamamide (Example 81), 60 ml of methanol, and 0.05 g of 10% palladium-carbon, a reaction similar to that conducted in Example 76 was carried out. As a result, 0.91 g of N-(2-dimethylaminoethyl)-N-(trans-4-methylcyclohexyl)-3-(3,4-methylenedioxyphenyl)propionamide (a compound of the present invention) was obtained as a colorless oil, which had the following physiochemical properties:
Proton nuclear magnetic resonance
spectrum ($\delta$ ppm in $CDCl_3$):
0.86 (3H, d, J=6 Hz),
0.9–1.8 (9H, m),
2.30 (6H, s), 2.38 (2H, t, J=7 Hz),
2.46 (2H, t, J=7 Hz),
2.85 (2H, t, J=7 Hz),
3.39 (2H, t, J=7 Hz), 3.41 (1H, m),
6.70 (2H, s), 6.6–6.8 (3H, m)
MS [(M+H)+]: 361

The compound described above was reacted in the ordinary method, converting it into N-(2-dimethylaminoethyl)-N-(trans-4-methylcyclohexyl)-3-(3,4-methylenedioxyphenyl)propionamide hydrochloride, which had the following physiochemical properties:
Proton nuclear magnetic resonance
spectrum ($\delta$ ppm in $D_2O$):
0.86 (3H, d, J=6 Hz),
0.9–1.9 (9H, m),
2.44 (2H, t, J=7 Hz),
2.59 (2H, t, J=7 Hz),
2.99 (2H, t, J=7 Hz), 3.04 (6H, s),
3.43 (1H, m), 4.11 (2H, t, J=7 Hz),
6.92 (2H, s), 6.9–7.1 (3H, m)
MS [(M-Cl)+: 361
HRMS ($C_{21}H_{33}N_2O_3$):
Theoretical value: 361.24912.
Measured value: 361.24707.

EXAMPLE 83

Esterification and Amidation, and Hydrolysis and Conversion into Non-toxic Salt

Using 2.7 g of 4-acetoxycinnamic acid derived from 4-hydroxycinnamic acid by the acetylation thereof, 2.8 ml of diethyl chlorophosphate, 2.7 ml of triethylamine, 100 ml of methylene chloride, 3 ml of N-(2-dimethylaminoethyl)-trans-4-methylcyclohexylamine (Example 78), 0.5 g of 4-dimethylaminopyridine, 100 ml of methanol, and 3 g of potassium carbonate, a reaction similar to that conducted in Example 75 was carried out. As a result, 1.79 g of N-(2-dimethylaminoethyl)-N-(trans-4-methylcyclohexyl)-4-hydroxycinnamamide (a compound of the present invention) was as white crystal, which had the following physiochemical properties:
Proton nuclear magnetic resonance
spectrum ($\delta$ ppm in $CDCl_3$):
0.88 (3H, d, J=6 Hz),
0.9–1.9 (9H, m),
2.37 (6H, s), 2.52 (2H, t, J=7 Hz),
4.42 (2H, t, J=7 Hz), 4.69 (1H, m),
6.65 (1H, d, J=16 Hz),
6.7–6.9 (2H, m),
7.27 (2H, d, J=8 Hz),
7.56 (2H, d, J=7 Hz)
MS [(M+H)+] 331
HRMS ($C_{20}H_{31}N_2O_2$):
Theoretical value: 331.23855.
Measured value: 331.23849.

The compound described above was reacted in the ordinary method, converting it into N-(2-dimethylaminoethyl)-N-(trans-4-methylcyclohexyl)-4-hydroxycinnamamide hydrochloride, which had the following physiochemical properties:
Proton nuclear magnetic resonance
spectrum ($\delta$ ppm in $D_2O$):
0.88 (3H, d, J=6 Hz),
0.9–1.9 (9H, m),
2.79 (2H, t, J=7 Hz), 3.06 (6H, s),
4.59 (2H, t, J=7 Hz), 4.70 (1H, m),
6.62 (1H, d, J=16 Hz),
6.7–6.9 (2H, m),
7.21 (2H, d, J=8 Hz),
7.46 (1H, d, J=16 Hz)
MS [(M-Cl)+]: 331
HRMS ($C_{20}H_{31}N_2O_2$):
Theoretical value: 331.23855.
Measured value: 331.23989.

EXAMPLE 84

Esterification and Amidation, and Hydrolysis and Conversion into Non-toxic Salt

Using 2.2 g of 4-acetoxy-3-methoxybenzoic acid derived from vanillic acid by the acetylation thereof, 2.8 ml of diethyl chlorophosphate, 2.7 ml of triethylamine, 100 ml of methylene chloride, 3 ml of N-(2-dimethylaminoethyl)-trans-4-methylcyclohexylamine (Example 78), and 0.5 g of 4-dimethylaminopyridine, a reaction similar to that conducted in Example 75 was carried out. As a result, 0.85 g of N-(2-dimethylaminoethyl)-N-(trans-4-methylcyclohexyl)vanilloylamide (a compound of the present invention) was obtained as a pale yellow oil, which had the following physiochemical properties:
Proton nuclear magnetic resonance
spectrum ($\delta$ ppm in $CDCl_3$):

0.88 (3H, d, J=6 Hz),
0.9–1.9 (9H, m),
2.04 (6H, s), 2.26 (2H, t, J=7 Hz),
3.42 (2H, t, J=7 Hz), 3.59 (1H, m),
3.70 (3H, s), 6.8–7.1 (3H, m)
MS [(M+H)+]: 335
HRMS ($C_{19}H_{31}N_2O_3$):
Theoretical value: 335.23347.
Measured value: 335.23381.

The compound described above was reacted in the ordinary method, converting it into N-(2-dimethylaminoethyl)-N-(trans-4-methylcyclohexyl)vanilloylamide hydrochloride, which had the following physiochemical properties:
Proton nuclear magnetic resonance
spectrum (δ ppm in $D_2O$):
0.88 (3H, d, J=6 Hz),
0.9–1.9 (9H, m),
2.42 (2H, t, J=7 Hz), 3.05 (6H, s),
3.67 (2H, t, J=7 Hz), 3.58 (1H, m),
3.71 (3H, s), 6.9–7.1 (3H, m)
MS [(M-Cl)+]: 335
HRMS ($C_{19}H_{31}N_2O_3$):
Theoretical value: 335. 23347.
Measured value: 335.23324.

EXAMPLE 85

Esterification and Amidation, and Hydrolysis and Conversion into Non-toxic Salt

Using 2.9 g of 4-acetoxy-3,5-dimethyoxycinnamic acid derived from 3,5-dimethoxy-4-hydroxycinnamic acid by the acetylation thereof, 2.8 ml of diethyl chlorophosphate, 2.7 ml of triethylamine, 100 ml of methylene chloride, 3 ml of N-(2-dimethylaminoethyl)-trans-4-methylcyclohexylamine (Example 78), and 0.5 g of 4-dimethylaminopyridine, a reaction similar to that conducted in Example 75 was carried out. As a result, 1.95 g of N-(2-dimethylaminoethyl)-N-(trans-4-methylcyclohexyl)-3,5-dimethoxy-4-hydroxycinnamamide (a compound of the present invention) was obtained as a pale yellow oil, which had the following physiochemical properties:
Proton nuclear magnetic resonance
spectrum (δ ppm in $CDCl_3$):
0.93 (3H, d, J=6 Hz),
0.9–1.9 (9H, m), 2.33 (6H, s),
2.42 (2H, t, J=7 Hz),
3.42 (2H, t, J=7 Hz), 3.49 (1H, m),
3.90 (6H, s),
6.64 (1H, d, J=16 Hz),
6.6–6.9 (2H, br),
7.56 (1H, d, J=16 Hz)
MS [(M+H)+]: 391
HRMS ($C_{22}H_{35}N_2O_4$):
Theoretical value: 391.25968.
Measured value: 391.25944.

The compound described above was reacted in the ordinary method, converting it into N-(2-dimethylaminoethyl)-N-(trans-4-methylcyclohexyl)3,5-dimethoxy-4-hydroxycinnamamide hydrochloride, which had the following physiochemical properties:
Proton nuclear magnetic resonance
spectrum (δ ppm in $D_2O$):
0.91 (3H, d, J=6 Hz),
0.9–1.9 (9H, m),
2.56 (2H, t, J=7 Hz), 3.04 (6H, s),
3.61 (2H, t, J=7 Hz), 3.47 (1H, m),
3.89 (6H, s),
6.58 (1H, d, J=16 Hz),
6.5–6.9 (2H, m),
7.50 (2H, d, J=16 Hz),
MS [(M-Cl)+]: 391
HRMS ($C_{22}H_{35}N_2O_4$):
Theoretical value: 391.25968.
Measured value: 391.26010.

EXAMPLE 86

Esterification and Amidation, and Conversion into Non-toxic Salt

Using 1.3 g of 3,4-dichlorocinammic acid, 1.4 ml of diethyl chlorophosphate, 1.4 ml of triethylamine, 60 ml of methylene chloride, 1.4 ml of N-(2-dimethylaminoethyl)-trans-4-methylcyclohexyl amine (Example 78), and 0.25 g of 4-dimethylaminopyridine, a reaction similar to that conducted in Example 81 was carried out. As a result, 2.45 g of N-(2-dimethylaminoethyl)-N-(trans-4-methylcyclohexyl)3,4-dichlorocinnamamide (a compound of the present invention) was obtained as white crystal, which had the following physiochemical properties:
Proton nuclear magnetic resonance
spectrum (δ ppm in $CDCl_3$):
0.90 (3H, d, J=6 Hz),
1.0–1.9 (9H, m), 2.32 (6H, s),
2.42 (2H, t, J=7 Hz),
3.41 (2H, t, J=7 Hz), 3.69 (1H, m),
6.88 (1H, d, J=16 Hz),
7.5–7.8 (4H, m)
MS [(M+H)+]: 383
HRMS ($C_{20}H_{29}N_2OCl_2$):
Theoretical value: 383.16569.
Measured value: 383.16537.

The compound described above was reacted in the ordinary method, converting it into N-(2-dimethylaminoethyl)-N-(trans-4-methylcyclohexyl)3,4-dichlorocinnamamide hydrochloride, which had the following physiochemical properties:
Proton nuclear magnetic resonance
spectrum (δ ppm in $D_2O$):
0.90 (3H, d, J=6 Hz),
1.0–1.9 (9H, m),
2.58 (2H, t, J=7 Hz), 3.08 (6H, s),
3.69 (1H, m), 3.91 (2H, t, J=7 Hz),
6.79 (1H, d, J=16 Hz),
7.3–7.6 (4H, m)
MS [(M-Cl)+]: 383
HRMS ($C_{21}H_{30}N_2OF_3$):
Theoretical value: 383.16569.
Measured value: 383.16537.

EXAMPLE 87

Esterification and Amidation, and Conversion into Non-toxic Salt

Using 1.1 g of 3-chlorocinnamic acid, 1.4 ml of diethyl chlorophosphate, 1.4 ml of triethylamine, 60 ml of methylene chloride, 1.4 ml of N-(2-dimethylaminoethyl)-trans-4-methylcyclohexylamine (Example 78), and 0.25 g of 4-dimethylaminopyridine, a reaction similar to that conducted in Example 81 was carried out. As a result, 2.06 g of N-(2-dimethylaminoethyl)-N-(trans-4-methylcyclohexyl)-3-chlorocinnamamide (a compound of the present invention) was obtained as white crystal, which had the following physiochemical properties:
Proton nuclear magnetic resonance spectrum (δ ppm in CDCl₃):
0.89 (3H, d, J=6 Hz),
0.9–1.9 (9H, m), 2.32 (6H, s),
2.44 (2H, t, J=7 Hz),
3.40 (2H, t, J=7 Hz), 3.71 (1H, m),
6.86 (1H, d, J=16 Hz),
7.3–7.5 (4H, m),
7.59 (1H, d, J=16 Hz)
MS [(M+H)+]: 349
HRMS (C₂₀H₃₀N₂OCl):
Theoretical value: 349.20467.
Measured value: 349.20501.

The compound described above was reacted in the ordinary method, converting it into N-(2-dimethylaminoethyl)-N-(trans-4-methylcyclohexyl)-3-chlorocinnamamide hydrochloride, which had the following physiochemical properties:
Proton nuclear magnetic resonance
spectrum (δ ppm in D₂O):
0.88 (3H, d, J=6 Hz),
0.9–1.9 (9H, m),
2.59 (2H, t, J=7 Hz), 3.06 (6H, s),
3.71 (2H, t, J=7 Hz), 3.70 (1H, m),
6.80 (1H, d, J=16 Hz),
7.1–7.4 (4H, m),
7.51 (1H, d, J=16 Hz)
MS [(M-Cl)+]: 349
HRMS (C₂₀H₃₀N₂OCl):
Theoretical value: 349.20467.
Measured value: 349.20435.

EXAMPLE 88

Esterification and Amidation, and Conversion into Non-toxic Salt

Using 1.1 g of 2-chlorocinnamic acid, 1.4 ml of diethyl chlorophosphate, 1.4 ml of triethylamine, 60 ml of methylene chloride, 1.4 ml of N-(2-dimethylaminoethyl)-trans-4-methylcyclohexyl amine (Example 78), and 0.25 g of 4-dimethylaminopyridine, a reaction similar to that conducted in Example 81 was carried out. As a result, 1.94 g of N-(2-dimethylaminoethyl)-N-(trans-4-methylcyclohexyl)-2-chlorocinnamamide (a compound of the present invention) was obtained as white crystal, which had the following physiochemical properties:
Proton nuclear magnetic resonance
spectrum (δ ppm in CDCl₃):
0.90 (3H, d, J=6 Hz),
0.9–1.9 (9H, m), 2.32 (6H, s),
2.44 (2H, t, J=7 Hz),
3.44 (2H, t, J=7 Hz), 3.72 (1H, m),
6.85 (1H, d, J=16 Hz),
7.2–7.6 (4H, m),
7.88 (1H, d, J=16 Hz)
MS [(M+H)+]: 349
HRMS (C₂₀H₃₀N₂OCl):
Theoretical value: 349.20467.
Measured value: 349.20489.

The compound described above was reacted in the ordinary method, converting it into N-(2-dimethylaminoethyl)-N-(trans-4-methylcyclohexyl)-2-chlorocinnamamide hydrochloride, which had the following physiochemical properties:
Proton nuclear magnetic resonance
spectrum (δ ppm in D₂O):
0.90 (3H, d, J=6 Hz),
0.9–1.9 (9H, m),
2.58 (2H, t, J=7 Hz), 3.08 (6H, s),
3.71 (1H, m) 3.76 (2H, t, J=7 Hz),
6.79 (1H, d, J=16 Hz),
7.1–7.5 (4H, m),
7.79 (1H, d, J=16 Hz)
MS [(M-Cl)+]: 349
HRMS (C₂₀H₃₀N₂OCl):
Theoretical value: 349.20467.
Measured value: 349.20462.

EXAMPLE 89

Esterification and Amidation, and Conversion into Non-toxic Salt

Using 1.0 g of 2-fluorocinnamic acid, 1.4 ml of diethyl chlorophosphate, 1.4 ml of triethylamine, 60 ml of methylene chloride, 1.4 ml of N-(2-dimethylaminoethyl)-trans-4-methylcyclohexylamine (Example 78), and 0.25 g of 4-dimethylaminopyridine, a reaction similar to that conducted in Example 81 was carried out. As a result, 1.69 g of N-(2-dimethylaminoethyl)-N-(trans-4-methylcyclohexyl)-2-fluorocinnamamide (a compound of the present invention) was obtained as white crystal, which had the following physiochemical properties:
Proton nuclear magnetic resonance
spectrum (δ ppm in CDCl₃):
0.86 (3H, d, J=6 Hz),
0.9–1.9 (9H, m), 2.32 (6H, m),
2.45 (2H, t, J=8 Hz),
3.39 (2H, t, J=8 Hz), 3.71 (1H, m),
7.00 (1H, d, J=16 Hz),
7.0–7.6 (4H, m),
7.70 (1H, d, J=16 Hz)
MS [(M+H)+]: 333
HRMS (C₂₀H₃₀N₂OF):
Theoretical value: 333.23442.
Measured value: 333.23440.

The compound described above was reacted in the ordinary method, converting it into N-(2-dimethylaminoethyl)-N-(trans-4-methylcyclohexyl)-2-fluorocinnamamide hydrochloride, which had the following physiochemical properties:
Proton nuclear magnetic resonance
spectrum (δ ppm in D₂O):
0.86 (3H, d, J=6 Hz),
0.9–1.9 (9H, m),
2.63 (2H, t, J=8 Hz), 3.09 (6H, s),
3.62 (2H, t, J=8 Hz), 3.70 (1H, m),
6.96 (1H, d, J=16 Hz),
7.0–7.6 (4H, m),
7.63 (1H, d, J=16 Hz)
MS [(M-Cl)+]: 333
HRMS (C₂₀H₃₀N₂OF):
Theoretical value: 333.23422.
Measured value: 333.23435.

EXAMPLE 90

Esterification and Amidation, and Conversion into Non-toxic Salt

Using 1.1 g of 3,4-difluorocinnamic acid, 1.4 ml of diethyl chlorophosphate, 1.4 ml of triethylamine, 60 ml of methylene chloride, 1.4 ml of N-(2-dimethylaminoethyl)-trans-4-methylcyclohexylamine (Example 78), and 0.25 g of 4-dimethylaminopyridine, a reaction similar to that conducted in Example 81 was carried out. As a result, 1.74 g of N-(2-dimethylaminoethyl)-N-(trans-4-methylcyclohexyl)-3,4-difluorocinnamamide (a compound of the present invention) was obtained as white crystal, which had the following physiochemical properties:
  Proton nuclear magnetic resonance
  spectrum (δ ppm in CDCl$_3$):
  0.89 (3H, d, J=6 Hz),
  0.9–1.9 (9H, m), 2.32 (6H, s),
  2.40 (2H, t, J=8 Hz),
  3.40 (2H, t, J=8 Hz), 3.72 (1H, m),
  6.78 (1H, d, J=16 Hz),
  7.1–7.4 (3H, m),
  7.56 (1H, d, J=16 Hz)
  MS [(M+H)+]: 351
  HRMS (C$_{20}$H$_{29}$N$_2$OF$_2$)
  Theoretical value: 351.22488.
  Measured value: 351.22480.

The compound described above was reacted in the ordinary method, converting it into N-(2-dimethylaminoethyl)-N-(trans-4-methylcyclohexyl)-3,4-difluorocinnamamide hydrochloride, which had the following physiochemical properties:
  Proton nuclear magnetic resonance
  spectrum (δ ppm in D$_2$O):
  0.88 (3H, d, J=6 Hz),
  0.9–1.9 (9H, m),
  2.59 (2H, t, J=8 Hz), 3.08 (6H, s),
  3.68 (2H, t, J=8 Hz), 3.71 (1H, m),
  6.71 (1H, d, J=16 Hz),
  7.0–7.4 (3H, m),
  7.50 (1H, d, J=16 Hz)
  MS [(M-Cl)+]: 351
  HRMS (C$_{20}$H$_{29}$N$_2$OF$_2$):
  Theoretical value: 351.22480.
  Measured value: 351.22534.

EXAMPLE 91

Esterification and Amidation, and Conversion into Non-toxic Salt

Using 1.3 g of 3-trifluoromethylcinnamic acid, 1.4 ml of diethyl chlorophosphate, 1.4 ml of triethylamine, 60 ml of methylene chloride, 1.4 ml of N-(2-dimethylaminoethyl)-trans-4-methylcyclohexylamine (Example 78), and 0.25 g of 4-dimethylaminopyridine, a reaction similar to that conducted in Example 81 was carried out. As a result, 2.25 g of N-(2-dimethylaminoethyl)-N-(trans-4-methylcyclohexyl)-3-trifluoromethylcinnamamide (a compound of the present invention) was obtained as white crystal, which had the following physiochemical properties:
  Proton nuclear magnetic resonance
  spectrum (δ ppm in CDCl$_3$):
  0.88 (3H, d, J=6 Hz),
  0.9–1.9 (9H, m), 2.31 (6H, s),
  2.40 (2H, t, J=7 Hz),
  3.38 (2H, t, J=7 Hz), 3.72 (1H, m),
  6.85 (1H, d, J=16 Hz),
  7.3–7.7 (5H, m),
  MS [(M+H)+]: 383
  HRMS (C$_{21}$H$_{30}$N$_2$OF$_3$):
  Theoretical value: 383.23102.
  Measured value: 383.23148.

The compound described above was reacted in the ordinary method, converting it into N-(2-dimethylaminoethyl)-N-(trans-4-methylcyclohexyl)-3-trifluoromethylcinnamamide hydrochloride, which had the following physiochemical properties:
  Proton nuclear magnetic resonance
  spectrum (δ ppm in D$_2$O):
  0.88 (3H, d, J=6 Hz),
  0.9–1.9 (9H, m),
  2.59 (2H, t, J=7 Hz), 3.09 (6H, s),
  3.71 (2H, t, J=7 Hz), 3.68 (1H, m), 20 6.76 (1H, d, J=16 Hz),
  7.2–7.6 (5H, m),
  MS [(M-Cl)+]: 383
  HRMS (C$_{21}$H$_{30}$N$_2$OF$_3$):
  Theoretical value: 383.23102.
  Measured value: 383.23144.

EXAMPLE 92

Esterification and Amidation, and Conversion into Non-toxic Salt

Using 2.0 g of 3-nitrocinnamic acid, 1.9 ml of diethyl chlorophosphate, 3.5 ml of triethylamine, 60 ml of methylene chloride, 2.3 ml of N-(2-dimethylaminoethyl)-trans-4-methylcyclohexylamine (Example 78), and 0.04 g of 4-dimethylaminopyridine, a reaction similar to that conducted in Example 81 was conducted. As a result, 1.54 g of N-(2-dimethylaminoethyl)-N-(trans-4-methylcyclohexyl)-3-nitrocinnamamide (a compound of the present invention) was obtained as white crystal, which had the following physiochemical properties:
  Proton nuclear magnetic resonance
  spectrum (δ ppm in CDCl$_3$):
  0.90 (3H, d, J=6 Hz),
  1.0–1.9 (9H, m), 2.34 (6H, s),
  2.47 (2H, t, J=8 Hz),
  3.42 (2H, t, J=8 Hz), 3.74 (1H, m),
  7.06 (1H, d, J=16 Hz),
  7.5–7.9 (5H, m),
  MS [(M+H)+]: 360

The compound described above was reacted in the ordinary method, converting it into N-(2-dimethylaminoethyl)-N-(trans-4-methylcyclohexyl)-3-nitrocinnamamide hydrochloride, which had the following physiochemical properties:
  Proton nuclear magnetic resonance
  spectrum (δ ppm in D$_2$O):
  0.89 (3H, d, J=6 Hz ),
  1.0–1.9 (9H, m),
  2.61 (2H, t, J=8 Hz), 3.08 (6H, s),
  3.68 (2H, t, J=8 Hz), 3.72 (1H, m),
  7.00 (1H, d, J=16 Hz),
  7.4–7.9 (5H, m),
  MS [(M-Cl)+]: 360
  HRMS (C$_{20}$H$_{30}$N$_3$O$_3$):
  Theoretical value: 360.22872.
  Measured value: 360.22674.

EXAMPLE 93

Esterification and Amidation, and Conversion into Non-toxic Salt

Using 2.3 g of 4-bromocinnammic acid, 1.9 ml of diethyl chlorophosphate, 3.5 ml of triethylamine, 60 ml of methylene chloride, 2.3 ml of N-(2-dimethylaminoethyl)-trans-4-methylcyclohexylamine (Example 78), and 0.04 g of 4-dimethylaminopyridine, a reaction similar to that conducted in Example 81 was carried out. As a result, 2.24 g of N-(2-dimethylaminoethyl)-N-(trans-4-methylcyclohexyl)-4-bromocinnamamide (a compound of the present invention) was obtained as white crystal, which had the following physiochemical properties:
  Proton nuclear magnetic resonance
  spectrum (δ ppm in CDCl$_3$):
  0.89 (3H, d, J=7 Hz), 0.9–1.9 (9H, m), 2.31 (6H, m),
2.39 (2H, t, J=8 Hz),
3.40 (2H, t, J=8 Hz), 3.72 (1H, m),
6.83 (1H, d, J=16 Hz),
7.35 (2H, d, J=9 Hz),
7.48 (2H, d, J=8 Hz),
7.58 (1H, d, J=16 Hz)
MS [(M+H)+]: 392

The compound described above was reacted in the ordinary method, converting it into N-(2-dimethylaminoethyl)-N-(trans-4-methylcyclohexyl)-4-bromocinnamamide hydrochloride, which had the following physiochemical properties:

Proton nuclear magnetic resonance spectrum (δ ppm in D$_2$O):
0.88 (3H, d, J=6 Hz),
0.9–1.9 (9H, m),
2.58 (2H, t, J=8 Hz), 3.09 (6H, s),
3.69 (2H, t, J=8 Hz), 3.71 (1H, m),
6.79 (1H, d, J=16 Hz),
7.29 (2H, d, J=9 Hz),
7.41 (2H, d, J=8 Hz),
7.51 (1H, d, J=16 Hz)
MS [(M-Cl)+]: 393
HRMS (C$_{20}$H$_{30}$N$_2$OBr):
Theoretical value: 393.15415.
Measured value: 393.15365.

EXAMPLE 94

Esterification and Amidation, and Conversion into Non-toxic Salt

Using 2.0 g of 4-acetylaminocinnamic acid derived from 4-aminocinnamic acid by the acetylation thereof, 1.9 ml of diethyl chlorophosphate, 3.5 ml of triethylamine, 60 ml of methylene chloride, 2.3 ml of N-(2-dimethylaminoethyl)-trans-4-methylcyclohexylamine (Example 78), and 0.04 g of 4-dimethylaminopyridine, a reaction similar to that conducted in Example 81 was carried out. As a result, 2.08 g of N-(2-dimethylaminoethyl)-N-(trans-4-methylcyclohexyl)-4-acetylaminocinnamamide (a compound of the present invention) was obtained as white crystal, which had the following physiochemical properties:

Proton nuclear magnetic resonance spectrum (δ ppm in CDCl$_3$):
0.88 (3H, d, J=6 Hz),
0.9–1.9 (9H, m), 2.18 (3H, s),
2.31 (6H, s),
2.45 (2H, t, J=8 Hz),
3.43 (2H, t, J=7 Hz), 3.74 (1H, m),
6.77 (1H, d, J=16 Hz),
7.40 (2H, d, J=9 Hz),
7.55 (2H, d, J=9 Hz),
7.60 (1H, d, J=16 Hz)
MS [(M+H)+]: 372
HRMS (C$_{22}$H$_{34}$N$_3$O$_2$):
Theoretical value: 372.26510.
Measured value: 372.26588.

The compound described above was reacted in the ordinary method, converting it into N-(2-dimethylaminoethyl)-N-(trans-4-methylcyclohexyl)-4-acetylaminocinnamamide hydrochloride, which had the following physiochemical properties:

Proton nuclear magnetic resonance spectrum (δ ppm in D$_2$O):
0.88 (3H, d, J=6 Hz),
0.9–1.9 (9H, m), 2.15 (3H, s),
2.60 (2H, t, J=8 Hz),
3.09 (6H, s), 3.69 (2H, t, J=7 Hz),
3.73 (1H, m),
6.71 (1H, d, J=16 Hz),
7.31 (2H, d, J=9 Hz),
7.49 (2H, d, J=9 Hz),
7.52 (1H, d, J=16 Hz)
MS [(M-Cl)+]: 372
HRMS (C$_{22}$H$_{34}$N$_3$O$_2$):
Theoretical value: 372.26510.
Measured value: 372.26524.

EXAMPLE 95

Esterification and Amidation, and Conversion into Non-toxic Salt

Using 2.7 g of 3,4-dimethoxycinnamic acid, 2.8 ml of diethyl chlorophosphate, 2.7 ml of triethylamine, 100 ml of methylene chloride, 3.0 ml of N-(2-dimethylaminoethyl)-trans-4-methylcyclohexylamine (Example 78), and 0.5 g of 4-dimethylaminopyridine, a reaction similar to that conducted in Example 81 was carried out. As a result, 1.53 g of N-(2-dimethylaminoethyl)-N-(trans-4-methylcyclohexyl)-3,4-dimethoxycinnamamide (a compound of the present invention) was obtained as white crystal, which had the following physiochemical properties:

Proton nuclear magnetic resonance spectrum (δ ppm in CDCl$_3$):
0.90 (3H, d, J=6 Hz),
1.0–1.8 (9H, m), 2.33 (6H, s),
2.46 (2H, t, J=7 Hz),
3.45 (2H, t, J=7 Hz), 3.72 (1H, m),
3.91 (6H, s),
6.72 (1H, d, J=16 Hz),
6.84 (1H, d, J=8 Hz),
7.0–7.2 (2H, m),
7.61 (1H, d, J=16 Hz)
MS [(M+H)+]: 375

The compound described above was reacted in the ordinary method, converting it into N-(2-dimethylaminoethyl)-N-(trans-4-methylcyclohexyl)-3,4-dimethoxycinnamamide hydrochloride, which had the following physiochemical properties:

Proton nuclear magnetic resonance spectrum (δ ppm in D$_2$O):
0.89 (3H, d, J=6 Hz),
0.9–1.9 (9H, m),
2.88 (2H, t, J=7 Hz), 3.05 (6H,s),
3.66 (2H, t, J=7 Hz), 3.71 (1H, m),
3.92 (6H, s),
6.69 (1H, d, J=16 Hz),
6.83 (1H, d, J=8 Hz),
6.9–7.2 (2H, m),
7.58 (1H, d, J=16 Hz)
MS [(M-Cl)+]: 375
HRMS (C$_{22}$H$_{35}$N$_2$O$_3$):
Theoretical value: 375.26477.
Measured value: 375.26414.

EXAMPLE 96

Esterification and Amidation, and Hydrolysis and Conversion into Non-toxic Salt

Using 3.4 g of 3,4-diacetoxycinnamic acid derived from caffeic acid by the acetylation thereof, 2.8 ml of diethyl chlorophosphate, 2.7 ml of triethylamine, 100 ml of methylene chloride, 3.0 ml of N-(2-dimethylaminoethyl)-trans-4-methylcyclohexylamine (Example 78), and 0.5 g of 4-dimethylaminopyridine, a reaction similar to that conducted in Example 81 was carried out. As a result, 0.68 g of N-(2-dimethylaminoethyl)-N-(trans-4-methylcyclohexyl)-3,4-diacetoxycinnamamide (a compound of the present invention) was obtained as pale yellow crystal, which had the following physiochemical properties:

Proton nuclear magnetic resonance spectrum ($\delta$ ppm in CDCl$_3$):
0.90 (3H, d, J=6 Hz),
0.9–1.8 (9H, m), 2.30 (6H, s),
2.32 (6H, s),
2.41 (2H, t, J=7 Hz),
3.38 (2H, t, J=7 Hz), 3.71 (1H, m),
6.71 (1H, d, J=16 Hz),
7.1–7.4 (3H, m),
7.52 (1H, d, J=16 Hz)
MS [(M+H)+]: 431
HRMS (C$_{24}$H$_{35}$N$_2$O$_5$):
Theoretical value: 431.25460.
Measured value: 431.25496.

The compound described above was reacted in the ordinary method, converting it into N-(2-dimethylaminoethyl)-N-(trans-4-methylcyclohexyl)-3,4-dihydroxycinnamamide hydrochloride, which had the following physiochemical properties:

Proton nuclear magnetic resonance spectrum ($\delta$ ppm in D$_2$O):
0.88 (3H, d, J=6 Hz),
0.9–1.8 (9H, m),
2.59 (2H, t, J=7 Hz), 3.08 (6H, s),
3.62 (2H, t, J=7 Hz), 3.71 (1H, m),
6.69 (1H, d, J=16 Hz),
7.0–7.4 (3H, m),
7.46 (1H, d, J=16 Hz)
MS [(M-Cl)+]: 347
HRMS (C$_{20}$H$_{31}$N$_2$O$_3$):
Theoretical value: 347.23347.
Measured value: 347.23169.

EXAMPLE 97

Esterification and Amidation, and Conversion into Non-toxic Salt

Using 2.0 g of 4-dimethylaminocinnamic acid, 1.9 ml of diethyl chlorophosphate, 3.5 ml of triethylamine, 60 ml of methylene chloride, 2.3 ml of N-(2-dimethylaminoethyl)-trans-4-methylcyclohexylamine (Example 78), and 0.04 g of 4-dimethylaminopyridine, a reaction similar to that conducted in Example 81 was carried out. As a result, 2.1 g of N-(2-dimethylaminoethyl)-N-(trans-4-methylcyclohexyl)-4-dimethylaminocinnamamide (a compound of the present invention) was obtained as white crystal, which had the following physiochemical properties:

Proton nuclear magnetic resonance spectrum ($\delta$ ppm in CDCl$_3$):
0.89 (3H, d, J=6 Hz),
0.9–1.9 (9H, m), 2.30 (6H, s),
2.32 (6H, s),
2.41 (2H, t, J=7 Hz),
3.39 (2H, t, J=7 Hz), 3.71 (1H, m),
6.84 (1H, d, J=16 Hz),
7.41 (2H, d, J=9 Hz),
7.53 (2H, d, J=9 Hz),
7.66 (1H, d, J=16 Hz), 6.38 (1H, m)
Ms [(M+H)+]: 358

The compound described above was reacted in the ordinary method, converting it into N-(2-dimethylaminoethyl)-N-(trans-4-methylcyclohexyl)-4-dimethylaminocinnamamide dihydrochloride, which had the following physiochemical properties:

Proton nuclear magnetic resonance spectrum ($\delta$ ppm in D$_2$O):
0.89 (3H, d, J=6 Hz),
0.9–1.9 (9H, m), 2.31 (6H, s),
2.59 (2H, t, J=7 Hz),
3.08 (6H, s), 3.61 (2H, t, J=7 Hz),
3.70 (1H, m),
6.79 (1H, d, J=16 Hz),
7.36 (2H, d, J=9 Hz),
7.42 (2H, d, J=9 Hz),
7.59 (1H, d, J=16 Hz)
MS [(M+H-2HCl)+]: 358
HRMS (C$_{22}$H$_{36}$N$_3$O):
Theoretical value: 358.28584.
Measured value: 358.28564.

EXAMPLE 98

Esterification and Amidation, and Hydrolysis and Conversion into Non-toxic Salt

Using 2.3 g of (4-acetoxy-3-methoxyphenyl)acetic acid derived from homovanillic acid by the acetylation thereof, 2.8 ml of diethyl chlorophosphate, 2.7 ml of triethylamine, 100 ml of methylene chloride, 3 ml of N-(2-dimethylaminoethyl)-trans-4-methylcyclohexylamine (Example 78), 0.5 g of 4-dimethylaminopyridine, 100 ml of methanol, and 3 g of potassium carbonate, a reaction similar to that conducted in Example 75 was carried out. As a result, 1.44 g of N-(2-dimethylaminoethyl)-N-(trans-4-methylcyclohexyl)-2-(4-hydroxy-3-methoxyphenyl)acetamide (a compound of the present invention) was obtained as pale yellow crystal, which had the following physiochemical properties:

Proton nuclear magnetic resonance spectrum ($\delta$ ppm in CDCl$_3$):
0.87 (3H, d, J=6 Hz),
0.9–2.0 (9H, m), 2.25 (6H, s),
2.48 (2H, t, J=7 Hz),
2.78 (2H, t, J=7 Hz), 3.31 (1H, m),
3.64 (2H, s), 3.87 (3H, s),
6.6–6.9 (3H, m)
MS [(M+H)+]: 349

The compound described above was reacted in the ordinary method, converting it into N-(2-dimethylaminoethyl)-N-(trans-4-methylcyclohexyl)-2-(4-hydroxy-3-methoxyphenyl)acetamide hydrochloride, which had the following physiochemical properties:
0.86 (3H, d, J=6 Hz),
0.9–2.0 (9H, m),
2.61 (2H, t, J=7 Hz),
2.99 (2H, t, J=7 Hz), 3.06 (6H, s),
3.32 (1H, m), 3.72 (2H, s),
3.86 (3H, s), 6.6–7.0 (3H, m)
MS [(M-Cl)+]: 349
HRMS (C$_{20}$H$_{33}$N$_2$O$_3$):
Theoretical value: 349.24912.
Measured value: 349.24792.

EXAMPLE 99

Knoevenagel Condensation 3.1 g of 2-fluoro-p-anisaldehyde and 4.2 g of malonic acid were dissolved in 80 ml of pyridine. Then, 0.5 ml of piperidine was added to the solution, and the solution was reacted at 80° C. for 4 hours. After reaction, the reaction solution was poured into 500 ml of ice-water, and 200 mol of 2N hydrochloric acid was added to the solution. The solution was extracted three times with 100 ml of ethyl acetate. The organic layer obtained was washed three times with 2N hydrochloric acid and twice with an aqueous sodium chloride solution, and was dried over magnesium sulfate. Thereafter, the solvent was removed in vacuo. The product obtained was recrystallized from methylene chloride/ether, yielding 2.7 g of 3-fluoro-4-methoxycinnamic acid as white crystal, which had the following physiochemical properties:

Proton nuclear magnetic resonance spectrum ($\delta$ ppm in DMSO-$d_6$):
3.88 (3H, s),
6.39 (1H, d, J=16 Hz),
7.13 (1H, t, J=9 Hz),
7.4–7.5 (2H, m),
7.59 (1H, d, J=16 Hz)
MS (M+): 196

EXAMPLE 100

Esterification and Amidation, and Conversion into Non-toxic Salt

Using 2.0 g of 3-fluoro-4-methoxycinnamic acid (Example 99), 2.8 ml of diethyl chlorophosphate, 2.7 ml of triethylamine, 100 ml of methylene chloride, 3 ml of N-(2-dimethylaminoethyl)-trans-4-methylcyclohexylamine (Example 78), and 0.5 g of 4-dimethylaminopyridine, a reaction similar to that performed in Example 81 was carried out. As a result, 2.21 g of N-(2-dimethylaminoethyl)-N-(trans-4-methylcyclohexyl)-3-fluoro-4-methoxycinnamamide (a compound of the present invention) was obtained as white crystal, which had the following physiochemical properties:

Proton nuclear magnetic resonance spectrum ($\delta$ ppm in CDCl$_3$):
0.89 (3H, d, J=6 Hz),
0.9–1.9 (9H, m), 2.32 (6H, s),
2.44 (2H, t, J=8 Hz),
3.39 (2H, t, J=8 Hz), 3.72 (1H, m),
3.91 (3H, s),
6.70 (1H, d, J=16 Hz),
6.90 (1H, t, J=9 Hz),
7.2–7.4 (2H, m),
7.57 (1H, d, J=16 Hz)
MS [(M+H)+]: 363

The compound described above was reacted in the ordinary method, converting it into N-(2-dimethylaminoethyl)-N-(trans-4-methylcyclohexyl)-3-fluoro-4-methoxycinnamamide hydrochloride, which had the following physiochemical properties:

Proton nuclear magnetic resonance spectrum ($\delta$ ppm in D$_2$O):
0.89 (3H, d, J=6 Hz),
0.9–1.9 (9H, m),
2.63 (2H, t, J=8 Hz), 3.09 (6H, s),
3.71 (2H, t, J=8 Hz), 3.72 (1H, m),
3.90 (3H, s),
6.62 (1H, d, J=16 Hz),
6.82 (1H, t, J=9 Hz),
7.1–7.3 (2H, m),
7.50 (1H, d, J=16 Hz)
MS [(M-Cl)+]: 363
HRMS (C$_{21}$H$_{32}$N$_2$O$_2$F):
Theoretical value: 363.24478.
Measured value: 363.24352.

EXAMPLE 101

Knoevenagel Condensation

Using 4.8 g of 2-chloro-4-(2-tetrahydropyranyloxy)-benzaldehyde derived from 2-chloro-4-hydroxybenzaldehyde by the introduction of tetrahydropyranyl group thereinto, 4.2 g of malonic acid, 80 ml of pyridine, and 0.5 ml of piperidine, a reaction similar to that performed in Example 99 was carried out. As a result, 3.1 g of 2-chloro-4-(2-tetrahydropyranyloxy)cinnamic acid was obtained as crystal, which had the following physiochemical properties:

Proton nuclear magnetic resonance spectrum ($\delta$ ppm in CDCl$_3$):
1.5–2.0 (6H, m), 3.5–3.9 (2H, m),
5.47 (1H, m),
6.32 (1H, d, J=16 Hz),
6.95 (1H, dd, J=6, 3 Hz),
7.14 (1H, d, J=2 Hz),
7.58 (1H, d, J=9 Hz),
8.12 (1H, d, J=16 Hz)
MS [(M+H)+]: 283
HRMS (C$_{14}$H$_{16}$N$_4$O):
Theoretical value: 283.07371.
Measured value: 283.07440.

EXAMPLE 102

Esterification and Amidation, and Conversion into Non-toxic Salt

Using 1.7 g of 2-chloro-4-(2-tetrahydropyranyloxy)-cinnamic acid, 1.4 ml of diethyl chlorophosphate, 1.4 ml of triethylamine, 60 ml of methylene chloride, 1.4 ml of N-(2-dimethylaminoethyl)-trans-4-methylcyclohexylamine (Example 78), and 0.25 g of 4-dimethylaminopyridine, a reaction similar to that performed in Example 81 was carried out. As a result, 3.01 g of N-(2-dimethylaminoethyl)-N-(trans-4-methylcyclohexyl)-2-chloro-4-(2-tetrahydropyranyloxy)cinnamamide (a compound of the present invention) was obtained as white crystal, which had the following physiochemical properties:

Proton nuclear magnetic resonance spectrum ($\delta$ ppm in CDCl$_3$):
0.88 (3H, d, J=6 Hz),
0.9–2.0 (15H, m ), 2.31 (6H, s),
2.41 (2H, t, J=7 Hz),
3.41 (2H, t, J=7 Hz),
3.5–3.9 (3H, m)
6.98 (1H, d, J=16 Hz),
7.01 (1H, dd, J=6, 3 Hz),
7.12 (1H, d, J=2 Hz),
7.60 (1H, d, J=9 Hz),
8.10 (1H, d, J=16 Hz)
MS [(M+H)+]: 437

The compound described above was reacted in the ordinary method, converting it into N-(2-dimethylaminoethyl)-N-(trans-4-methylcyclohexyl)-2-chloro-4-hydroxycinnamamide hydrochloride, which had the following physiochemical properties:

Proton nuclear magnetic resonance spectrum ($\delta$ ppm in D$_2$O):
0.88 (3H, d, J=6 Hz),
0.9–2.0 (9H, m),
2.59 (2H, t, J=7 Hz), 3.08 (6H, s),
3.62 (2H, t, J=7 Hz), 3.61 (1H, m),
6.91 (1H, d, J=16 Hz),
7.0–7.2 (2H, m), 7.56 (1H, d, J=9 Hz),
8.01 (1H, d, J=16 Hz)
MS [(M-Cl)+]: 365
HRMS ($C_{20}H_{30}N_2O_2Cl$):
Theoretical value: 365.19958.
Measured value: 365.19868.

EXAMPLE 103

Reduction 0.1 g of 20% palladium hydroxide-carbon was added to a solution of 3 g of N-(1-phenylethyl)-4-methyl-1-cyclohexylamine disclosed in the literature G. Knupp, and A. W. Frahm, J. Chem. Research, 164–165 (1981)] in 50 ml of methanol. The solution was vigorously stirred for 18 hours at room temperature under normal-pressure hydrogen gas. After reaction, the catalyst was filtered out, and the solvent was removed in vacuo from the filtrate, yielding 1.5 g of cis-4-methyl-1-cyclohexylamine as a colorless oil, which had the following physiochemical properties:

Proton nuclear magnetic resonance spectrum ($\delta$ ppm in $CDCl_3$):
  0.90 (3H, d, J=8 Hz),
  1.3–2.1 (9H, m), 3.49 (1H, m)
MS (M+): 113
HRMS ($C_7H_{15}N$):
Theoretical value: 113.12042.
Measured value: 113.12002.

EXAMPLE 104

Esterification and Amidation

A solution prepared by mixing 2.5 g of 4-hydroxy-3-methoxycinnamic acid, 2.8 ml of diethyl chlorophosphate, 2.7 ml of triethyleneamine, and 100 ml of methylene chloride was stirred for 1 hour at room temperature. Then, 1.8 ml of cis-4-methyl-1-cyclohexylamine (Example 103) and 0.5 g of 4-dimethylaminopyridine were added to the solution, and the solution was further stirred for 4 hours at room temperature.

After reaction, the reaction solution was washed five times with 200 ml of an aqueous sodium hydrogencarbonate solution and dried over magnesium sulfate. Thereafter, the solvent was removed in vacuo. The product obtained was recrystallized from methylene chloride/hexane, yielding 2.8 g of N-(cis-4-methylcyclohexyl)-4-acetoxy-3-methoxycinnamamide (a compound of the present invention) as white crystal, which had the following physiochemical properties:

Proton nuclear magnetic resonance spectrum ($\delta$ ppm in $CDCl_3$):
  0.93 (3H, d, J=7 Hz),
  1.0–1.8 (9H, m),
  2.32 (3H, s), 3.86 (3H, s),
  4.12 (1H, br), 5.69 (1H, br),
  6.30 (1H, d, J=16 Hz),
  7.0–7.2 (3H, m),
  7.53 (1H, d, J=16 Hz)
IR$_{max}$ (KBr, cm$^{-1}$): 3284, 2938, 1765, 1655
MS (M+): 331
Elemental analysis ($C_{19}H_{25}NO_4$):
Theoretical value; C: 68.86, H: 7.60, N: 4.23.
Measured value; C: 68.83, H: 7.49, N: 4.24.

EXAMPLE 105

Hydrolysis and Conversion into Non-toxic Salt 5 g of sodium carbonate was added to a solution of 2.8 g of N-(cis-4-methylcyclohexyl)-4-acetoxy-3-methoxycinnamamide (Example 104) in 100 ml of methanol. The solution was stirred for 2 hours at room temperature. After reaction, 2N hydrochloric acid was added to the reaction solution, acidifying the solution. The solution was extracted three times with 90 ml of ethyl acetate. The organic layer obtained was washed twice with an aqueous sodium chloride solution and dried over magnesium sulfate. Thereafter, the solvent was removed in vacuo. The product obtained was recrystallized from ethyl acetate/hexane, yielding 2.2 g of N-(cis-4-methylcyclohexyl)-4-hydroxy-3-methoxycinnamamide (a compound of the present invention) as white crystal, which had the following physiochemical properties:

Melting point: 135.8°–136.9° C.
Proton nuclear magnetic resonance spectrum ($\delta$ ppm in DMSO-$d_6$):
  0.90 (3H, d, J=6 Hz),
  1.2–1.7 (9H, m), 3.82 (3H, s),
  3.91 (1H, br), 5.73 (1H, s),
  6.53 (1H, d, J=16 Hz),
  6.76 (1H, d, J=8 Hz),
  6.95 (1H, dd, J=6, 2 Hz),
  7.10 (1H, d, J=2 Hz),
  7.26 (1H, d, J=16 Hz),
  7.74 (1H, d, J=8 Hz), 9.35 (1H, s)
IR$_{max}$ (KBr, cm$^{-1}$): 3254, 2954, 1668
MS (M+): 289
Elemental analysis ($C_{17}H_{23}NO_3$):
Theoretical value; C: 70.56, H: 8.01, N: 4.84.
Measured value; C: 70.61, H: 7.97, N: 5.01.

The compound described above was reacted in the ordinary method, converting it into sodium N-(cis-4-methylcyclohexyl)-3-methoxy-4-oxidocinnamamide, which had the following physiochemical properties:

Proton nuclear magnetic resonance spectrum ($\delta$ ppm in $D_2O$):
  0.86 (3H, d, J=6 Hz),
  1.0–1.9 (9H, m),
  3.81 (3H, s), 3.89 (1H, m),
  6.51 (1H, d, J=16 Hz),
  6.38 (1H, d, J=16 Hz),
  6.64 (1H, d, J=8 Hz),
  6.91 (1H, d, J=8 Hz), 7.05 (1H, s),
  7.42 (1H, d, J - 16 Hz)
MS [(M+Na)+]: 334, [(M+H)+]: 312
HRMS ($C_{17}H_{22}NO_3Na_2$):
Theoretical value: 334.13957.
Measured value: 334.13870.

EXAMPLE 106

Alkylation 6.2 g of potassium carbonate and 4.2 ml of 1-bromo-2-chloroethane were added to a solution of 8.67 g of N-(cis-4-methylcyclohexyl)-4-hydroxy-3-methoxycinnamamide (Example 105) in 200 ml of methylisobutyl-ketone. The solution was reacted for 10 hours, while it was refluxed. After reaction, the reaction solution was allowed to cool, added with 200 ml of methylene chloride and 200 ml of an aqueous sodium chloride solution, and subjected to extraction. The aqueous layer was extracted twice with 100 ml of methylene chloride. The organic layer obtained was washed twice with an aqueous sodium chloride solution and dried over magnesium sulfate. Thereafter, the solvent was removed in vacuo. The product obtained was recrystallized from methylene chloride/ether, yielding 8.76 g of N-(cis-4-methylcyclohexyl)-4-(2-chloroethoxy)-3-methoxycinnamamide (a compound of the present invention) as white crystal, which had the following physiochemical properties:

Proton nuclear magnetic resonance spectrum (δ ppm in CDCl$_3$):
0.88 (3H, d, J=6 Hz),
1.0–1.8 (9H, m),
3.81 (2H, t, J=7 Hz), 3.87 (3H, s),
4.06 (1H, m), 4.25 (2H, t, J=7 Hz),
5.49 (1H, m),
6.26 (1H, d, J=16 Hz),
6.81 (1H, d, J=8 Hz),
7.0–7.2 (2H, m),
7.47 (1H, d, J=16 Hz)
MS [(M+H)+]: 352

EXAMPLE 107

Amination and Conversion into Non-toxic Salt 40 ml of a 50% aqueous dimethylamine solution was added to a solution of 2 g of N-(cis-4-methylcyclohexyl)-4-(2-chloroethoxy)-3-methoxycinnamamide (Example 106) in 40 ml of methylisobutylketone. The solution was reacted for 18 hours by heating heated to 110° C., in a closed system. After reaction, the reaction solution was added with 200 ml of an aqueous sodium chloride solution and 100 ml of methylene chloride, and subjected to extraction. The aqueous layer was extracted twice with 100 ml of methylene chloride. The organic layer obtained was washed twice with an aqueous sodium chloride solution and dried over magnesium sulfate. Thereafter, the solvent was removed in vacuo. The product obtained was recrystallized from methylene chloride/ether, yielding 1.6 g of N-(cis-4-methylcyclohexyl)-4-(2-dimethylaminoethoxy)-3-methoxycinnamamide (a compound of the present invention) as white crystal, which had the following physiochemical properties:

Proton nuclear magnetic resonance spectrum (δ ppm in CDCl$_3$):
0.91 (3H, d, J=6 Hz),
1.0–1.8 (9H, m), 2.36 (6H, s),
2.73 (2H, t, J=7 Hz), 3.88 (3H, s),
4.09 (2H, t, J=7 Hz), 4.10 (1H, m),
5.74 (1H, m),
6.28 (1H, d, J=16 Hz),
6.83 (1H, d, J=8 Hz),
7.0–7.2 (2H, m),
7.49 (1H, d, J=16 Hz)
MS [(M+H)+]: 361
HRMS (C$_{21}$H$_{33}$N$_2$O$_3$):
Theoretical value: 361.24943.
Measured value: 361.24912.

The compound described above was reacted in the ordinary method, converting it into N-(cis-4-methylcyclohexyl)-4-(2-dimethylaminoethoxy)-3-methoxycinnamamide hydrochloride, which had the following physiochemical properties:

Proton nuclear magnetic resonance spectrum (δ ppm in D$_2$O):
1.11 (3H, d, J=6 Hz),
1.3–2.1 (9H, m), 3.22 (6H, s),
3.78 (2H, t, J=7 Hz),
3.88 (3H, s), 4.21 (1H, br),
4.45 (2H, t, J=7 Hz),
6.92 (1H, d, J=16 Hz),
7.04 (1H, d, J=8 Hz), 7.19 (1H, s),
7.23 (1H, d, J=8 Hz),
7.61 (1H, d, J=16 Hz)
MS [(M-Cl)+]: 361
HRMS (C$_{21}$H$_{33}$N$_2$O$_3$):
Theoretical value: 361.24912.
Measured value: 361.24868.

EXAMPLE 108

Reduction and Conversion into Non-toxic Salt 0.05 g of 10% palladium-carbon was added to a solution of 1 g of N-(cis-4-methylcyclohexyl)-4-(2-dimethylaminoethoxy)-3-methoxycinnamamide (Example 107) in 50 ml of methanol. The solution was vigorously stirred for 16 hours under normal-pressure hydrogen gas. After reaction, the catalyst was filtered out, and the solvent was removed in vacuo from the filtrate. The product obtained was recrystallized from methylene chloride/ether, yielding 0.93 g of N-(cis-4-methylcyclohexyl)-3-[4-(2-dimethylaminoethoxy)-3-methoxyphenyl]propionamide (a compound of the present invention) as white crystal, which had the following physiochemical properties:

Proton nuclear magnetic resonance spectrum (δ ppm in CDCl$_3$):
0.85 (3H, d, J=6 Hz),
1.2–1.6 (9H, m), 2.34 (6H, s),
2.39 (2H, t, J=7 Hz),
2.74 (2H, t, J=7 Hz),
2.87 (2H, t, J=7 Hz), 3.83 (3H, s),
3.98 (1H, m), 4.05 (2H, t, J=7 Hz),
5.41 (1H, m), 6.7–6.9 (3H, m)
MS [(M+H)+]: 363
HRMS (C$_{21}$H$_{35}$N$_2$O$_3$):
Theoretical value: 363.26462.
Measured value: 363.26477.

The compound described above was reacted in the ordinary method, converting it into N-(cis-4-methylcyclohexyl)-3-[4-(2-dimethylaminoethoxy)-3-methoxyphenyl]propionamide hydrochloride, which had the following physiochemical properties:

Proton nuclear magnetic resonance spectrum (δ ppm in D$_2$O):
1.04 (3H, d, J=6 Hz),
1.3–2.1 (9H, m),
2.51 (2H, t, J=7 Hz),
2.90 (2H, t, J=7 Hz), 3.18 (6H, s),
3.69 (2H, t, J=7 Hz), 3.88 (3H, s),
4.42 (2H, t, J=7 Hz),
7.2–7.4 (3H, m)
MS [(M-Cl)+]: 363
HRMS (C$_{21}$H$_{35}$N$_2$O$_3$):
Theoretical value: 363.26477.
Measured value: 363.26427.

EXAMPLE 109

Esterification and Amidation

Using 6.5 ml of diethyl chlorophosphate, 18 ml of triethylamine, 5.2 g of dimethylaminoglycine hydrochloride, 5 g of cis-4-methylcyclohexylammonium chloride, and 0.15 g of 4-dimethylaminopyridine, a reaction similar to that performed in Example 77 was carried out. As a result, 4.8 g of N-(cis-4-methylcyclohexyl)-2-dimethylaminoacetamide was obtained as a pale yellow oil, which had the following physiochemical properties:

Proton nuclear magnetic resonance spectrum (δ ppm in CDCl$_3$):

0.92 (3H, d, J=6 Hz),
1.1–1.7 (9H, m), 2.30 (6H, s),
2.93 (2H, s), 4.0 (1H, m)
MS [(M+H)+]: 199
HRMS (C$_{11}$H$_{23}$N$_2$O):
Theoretical value: 199.18104.
Measured value: 199.18272.

EXAMPLE 110

Using 4.8 g of N-(cis-4-methylcyclohexyl)-2-dimethylaminoacetamide (Example 109), 1.8 g of lithium aluminum hydride, 150 ml of THF, and 5 g of sodium sulfate decahydrate, a reaction similar to that performed in Example 78 was carried out. As a result, 2.9 g of N-(2-dimethylaminoethyl)-cis-4-methylcyclohexylamine was obtained as a colorless oil, which had the following physiochemical properties:

Proton nuclear magnetic resonance spectrum ($\delta$ ppm in CDCl$_3$):
0.89 (3H, d, J=6 Hz),
1.2–1.8 (9H, m), 2.24 (6H, s),
2.38 (2H, t, J=7 Hz), 2.59 (1H, m),
2.64 (2H, t, J=7 Hz)
Ms [(M+H)+]: 185
HRMS (C$_{11}$H$_{25}$N$_2$):
Theoretical value: 185.20177.
Measured value: 185.20242.

EXAMPLE 111

Esterification and Amidation, and Hydrolysis and Conversion into Non-toxic Salt

Using 2.5 g of 4-acetoxy-3-methoxycinnamic acid, 2.8 ml of diethyl chlorophosphate, 2.7 ml of triethylamine, 100 ml of methylene chloride, 3 ml of N-(2-dimethylaminoethyl)-cis-4-methylcyclohexylamine (Example 110), and 0.5 g of 4-dimethylaminopyridine, a reaction similar to that conducted in Example 75 was carried out. As a result, 1.6 g of N-(2-dimethylaminoethyl)-N-(cis-4-methylcyclohexyl)-4-hydroxy-3-methoxycinnamamide (a compound of the present invention) was obtained as white crystal, which had the following physiochemical properties:

Proton nuclear magnetic resonance spectrum ($\delta$ ppm in CDCl$_3$):
0.98 (3H, d, J=7 Hz),
1.0–2.0 (9H, m), 2.31 (6H, s),
2.42 (2H, t, J=7 Hz),
3.43 (2H, t, J=7 Hz), 3.82 (3H, s), i0 4.01 (1H, m),
6.79 (1H, d, J=16 Hz),
7.0–7.4 (3H, m),
7.36 (1H, d, J=16 Hz)
MS [(M+H)+]: 361
HRMS (C$_{21}$H$_{32}$N$_2$O$_3$):
Theoretical value: 361.24912.
Measured value: 361.24910.

The compound described above was reacted in the ordinary method, converting it into N-(2-dimethylaminoethyl)-N-(cis-4-methylcyclohexyl)-4-hydroxy-3-methoxycinnamamide hydrochloride, which had the following physiochemical properties:

Proton nuclear magnetic resonance spectrum ($\delta$ ppm in D$_2$O):
1.00 (3H, d, J=7 Hz),
1.0–2.0 (9H, m),
2.93 (2H, t, J=7 Hz), 3.05 (6H, s),
3.82 (3H, s), 3.91 (2H, t, J=7 Hz),
4.02 (1H, m),
6.75 (1H, d, J=16 Hz),
6.9–7.3 (3H, m),
7.31 (1H, d, J=16 Hz)
MS [(M-Cl)+]: 361
HRMS (C$_{21}$H$_{33}$N$_2$O$_3$):
Theoretical value: 361.24912.
Measured value: 361.24969.

EXAMPLE 112

Reduction and Conversion into Non-toxic Salt

Using a solution of 1 g of N-(2-dimethylaminoethyl)-N-(cis-4-methylcyclohexyl)-4-hydroxy-3-methoxycinnamamide (Example 111) in 60 ml of methanol, and 0.05 g of 10% palladium-carbon, a reaction similar to that conducted in Example 76 was carried out. As a result, 0.91 g of N-(2-dimethylaminoethyl)-N-(cis-4-methylcyclohexyl)-3-(4-hydroxy-3-methoxyphenyl)propionamide (a compound of the present invention) was obtained as a colorless oil, which had the following physiochemical properties:

Proton nuclear magnetic resonance spectrum ($\delta$ ppm in CDCl$_3$):
0.98 (3H, d, J=6 Hz),
1.0–2.0 (9H, m), 2.32 (6H, s),
2.39 (2H, t, J=7 Hz),
2.59 (2H, t, J=7 Hz),
2.72 (2H, t, J=7 Hz),
3.45 (2H, t, J=7 Hz), 3.83 (3H, s),
4.01 (1H, m), 7.0–7.4 (3H, m)
MS [(M+H)+]: 363
HRMS (C$_{21}$H$_{35}$N$_2$O$_3$):
Theoretical value: 363.26477.
Measured value: 363.26462.

The compound described above was reacted in the ordinary method, converting it into N-(2-dimethylaminoethyl)-N-(cis-4-methylcyclohexyl)-3-(4-hydroxy-3-methoxyphenyl)propionamide hydrochloride, which had the following physiochemical properties:

Proton nuclear magnetic resonance spectrum ($\delta$ ppm in D$_2$O):
0.99 (3H, d, J=6 Hz),
1.0–2.0 (9H, m),
2.53 (2H, t, J=7 Hz),
2.89 (2H, t, J=7 Hz), 3.09 (6H, s),
3.51 (2H, t, J=7 Hz), 3.82 (3H, s),
4.02 (1H, m), 4.41 (2H, t, J=7 Hz),
7.0–7.4 (3H, m)
MS [(M-Cl)+]: 363
HRMS (C$_{21}$H$_{35}$N$_2$O$_3$):
Theoretical value: 363.26477.
Measured value: 363.26444.

EXAMPLE 113

Esterification and Amidation

Using 4g of 4-(4-benzyloxy-3-methoxyphenyl)-1,3-butadiene-1-carboxylic acid disclosed in the literature [R. Bäckström, E. Honkanen, A. Pippuri, P. Kairisalo, J. Pystynen, K. Heinola, E. Nissinen, I. Linden, P. T. Männistö, S. Kaakkola, and P. Pohto, J. Med. Chem., 32, 841–848 (1989)], 3 ml of diethyl chlorophosphate, 3.5 ml of triethylamine, 150 ml of methylene chloride, 4 ml of N-(2-dimethylaminoethyl)-trans-4-methylcyclohexylamine (Example 78), and 0.5 g of 4-dimethylaminopyridine, a reaction similar to that conducted in Example 81 was carried out. As a result, 3.81 g of N-(2-dimethylaminoethyl)-N-(trans-4-methylcyclohexyl)-4-(4-benzyloxy-3-methoxyphenyl)-1,3-butadiene-1-carboxamide (a compound of the present invention) was obtained as a pale yellow oil, which had following physiochemical properties:

Proton nuclear magnetic resonance spectrum (δ ppm in CDCl$_3$):
0.87 (3H, d, J=6 Hz),
0.9–1.9 (9H, m),
2.29 (6H, s), 2.42 (2H, t, J=7 Hz),
3.68 (1H, m), 3.88 (3H, s),
5.23 (2H, s),
6.23 (1H, d, J=16 Hz),
6.7–7.3 (5H, m),
7.43 (1H, d, J=16 Hz)
MS [(M+H)+]: 477
HRMS (C$_{30}$H$_{41}$N$_2$O$_3$):
Theoretical value: 477.31172.
Measured value: 477.31212.

EXAMPLE 114

Reduction and Conversion into Non-toxic Salt 3.81 g of N-(2-dimethylaminoethyl)-N-(trans-4-methylcyclohexyl)-4-(4-benzyloxy-3-methoxyphenyl)-1,3-butadiene-1-carboxamide (Example 113) was dissolved in 100 ml of methanol. 0.2 g of 10% palladium-carbon was added to the solution. The solution was vigorously stirred at room temperature under normal-pressure hydrogen gas. After 18 hours, the reaction was ceased, and the catalyst was filtered out. The solvent was removed in vacuo from the filtrate, yielding 2.1 g of N-(2-dimethylaminoethyl)-N-(trans-4-methylcyclohexyl)-5-(4-hydroxy-3-methoxyphenyl)valeramide (a compound of the present invention) as a pale yellow oil, which had the following physiochemical properties:

Proton nuclear magnetic resonance spectrum (δ ppm in CDCl$_3$):
0.87 (3H, d, J=6 Hz),
0.9–2.2 (13H, m), 2.28 (6H, s),
2.39 (2H, t, J=7 Hz),
2.44 (2H, t, J=7 Hz),
2.68 (2H, T, J=7 Hz),
2.99 (2H, t, J=7 Hz),
3.48 (2H, t, J=7 Hz), 3.68 (1H, m),
3.86 (3H, s), 6.6–6.9 (3H, m)
MS [(M+H)+]: 391
HRMS (C$_{23}$H$_{39}$N$_2$O$_3$):
Theoretical value: 391.29607.
Measured value: 391.29576.

The compound described above was reacted in the ordinary method, converting it into N-(2-dimethylaminoethyl)-N-(trans-4-methylcyclohexyl)-5-(4-hydroxy-3-methoxyphenyl)valeramide hydrochloride, which had the following physiochemical properties:

Proton nuclear magnetic resonance spectrum (δ ppm in D$_2$O):
0.87 (3H, d, J=6 Hz),
0.9–2.2 (13H, m),
2.51 (2H, t, J=7 Hz),
2.99 (2H, t, J=7 Hz), 3.08 (6H, s),
3.41 (2H, t, J=7 Hz), 3.68 (1H, m),
3.71 (2H, t, J=7 Hz), 3.85 (3H, s),
6.5–6.9 (3H, m)
MS [(M-Cl)+]: 391
HRMS (C$_{23}$H$_{39}$N$_2$O$_3$):
Theoretical value: 391.29607.
Measured value: 391.29606.

EXAMPLE 115

Esterification and Amidation, and Hydrolysis and Conversion into Non-toxic Salt

A mixture solution of 5.9 g of 4-acetoxy-3-methoxycinnamic acid, 4.6 ml of diethyl chlorophosphate, 11 ml of triethylamine and 150 ml of methylene chloride was stirred for 1 hour at room temperature. Next, 3 ml of 4-methyl-1-aminopiperazine and 0.1 g of 4-dimethylaminopiridine were added under ice-cooling to the solution. The solution was reacted for 4 hours at room temperature. After reaction, the solvent was removed in vacuo. To the residue, 150 ml of methanol and 10 g of potassium carbonate were added, and the solution was stirred for 2 hours at room temperature.

After reaction, 2N hydrochloric acid was added to the reaction solution, acidifying the solution. The solution was washed twice with 100 ml of methylene chloride, and an aqueous sodium hydrogencarbonate solution was added to the aqueous layer, neutralizing the aqueous layer. Thereafter, the solution was extracted three times with 100 ml of ethyl acetate. The organic oil layer obtained was washed once with an aqueous sodium hydrogencarbonate solution and dried over magnesium sulfate. Then, the solvent was removed in vacuo, yielding 2.9 g of N-(4-methylpiperazinyl)-4-hydroxy-3-methoxycinnamamide (a compound of the present invention) as a pale yellow oil, which had the following physiochemical properties:

Proton nuclear magnetic resonance spectrum (δ ppm in CDCl$_3$):
2.20 (3H, s), 2.2–2.8 (8H, m),
3.78 (1H, m), 3.80 (3H, s),
6.30 (1H, d, J=16 Hz),
6.9–7.2 (3H, m),
7.37 (1H, d, J=16 Hz)
MS [(M+H)+]: 292

The compound described above was reacted in the ordinary method, converting it into N-(4-methylpiperazinyl)-4-hydroxy-3-methoxycinnamamide dichlorohydride, which had the following physiochemical properties:

Proton nuclear magnetic resonance spectrum (δ ppm in D$_2$O):
2.18 (3H, s), 2.2–2.8 (8H, m),
3.76 (1H, m), 3.80 (3H, s),
6.21 (1H, d, J=16 Hz),
6.7–7.1 (3H, m),
7.28 (1H, d, J=16 Hz)
MS [(M+H-2HCl)+]: 292
HRMS (C$_{15}$H$_{22}$N$_3$O$_3$):
Theoretical value: 292.16612.
Measured value: 292.16668.

EXAMPLE 116

Esterification and Amidation, and Hydrolysis and Conversion into Non-toxic Salt

Using 5.1 g of 4-acetoxy-3-methoxycinnamic acid, 4.6 ml of diethyl chlorophosphate, 11 ml of triethylamine, 3.6 ml of 4-aminomethylpiperidine, and 0.1 g of 4-dimethylaminopyridine, a reaction similar to that conducted in Example 115 was carried out. The crude product obtained was recrystallized from ethyl acetate/ether, yielding 3.3 g of N-methyl-N-[4-(1-methylpiperidinyl)]-4-hydroxy-3-methoxycinnamamide (a compound of the present invention) as white crystal, which had the following physiochemical properties:

Proton nuclear magnetic resonance spectrum (δ ppm in CDCl₃):
1.6–2.2 (4H, m), 2.32 (6H, s),
2.9–3.1 (4H, m), 3.86 (1H, m),
3.87 (3H, s),
6.73 (1H, d, J=16 Hz),
6.9–7.2 (3H, m),
7.56 (1H, d, J=16 Hz)
MS [(M+H)+]: 305
HRMS (C₁₇H₂₅N₂O₃):
Theoretical value: 305.18652.
Measured value: 305.18665.

The compound described above was reacted in the ordinary method, converting it into N-methyl-N-[4-(1-methylpiperidinyl)]-4-hydroxy-3-methoxycinnamamide hydrochloride, which had the following physiochemical properties:

Proton nuclear magnetic resonance spectrum (δ ppm in D₂O):
1.6–2.2 (4H, m), 2.30 (6H, s),
2.8–3.1 (4H, m), 3.84 (1H, m),
3.85 (3H, s),
6.69 (1H, d, J=16 Hz),
6.8–7.2 (3H, m),
7.54 (1H, d, J=16 Hz)
MS [(M-Cl)+]: 305
HRMS (C₁₇H₂₅N₂O₃):
Theoretical value: 305.18652.
Measured value: 305.18671.

EXAMPLE 117

Esterification and Amidation

Using 4g of 4-(4-benzyloxy-3-methoxyphenyl)-1,3-butadiene-1-carboxylic acid, 3 ml of diethyl chlorophosphate, 3.5 ml of triethylamine, 150 ml of methylene chloride, 2.2 g of trans-4-methylcyclohexylammonium chloride, and 0.5 g of -dimethylaminopyridine, a reaction similar to that conducted in Example 81 was carried out. As a result, 3.62 g of N-(trans-4-methylcyclohexyl)-4-(4-benzyloxy-3-methoxyphenyl)-1,3-butadiene-1-carboxamide (a compound of the present invention) was obtained as a pale yellowish brown oil, which had the following physiochemical properties:

Proton nuclear magnetic resonance spectrum (δ ppm in CDCl₃):
0.85 (3H, d, J=6 Hz),
0.9–2.0 (9H, m), 3.64 (1H, m),
3.86 (3H, s), 5.24 (2H, s),
5.44 (1H, m),
6.21 (1H, d, J=16 Hz),
6.7–7.2 (10H, m),
7.47 (1H, d, J =16 Hz)
MS [(M+H)+]: 406
HRMS (C₂₆H₃₂NO₃):
Theoretical value: 406.23822.
Measured value: 406.23851.

EXAMPLE 118

Reduction 3.62 g of N-(trans-4-methylcyclohexyl)-4-(4-benzyloxy-3-methoxyphenyl)-1,3-butadiene-1-carboxamide (Example 117) was dissolved in 150 ml of methanol. 0.2 g of 10% palladium-carbon was added to the solution. The solution was stirred for 16 hours under normal-pressure hydrogen gas. After reaction, the catalyst was filtered out, and the solvent was removed in vacuo from the filtrate, yielding 2.3 g of N-(trans-4-methylcyclohexyl)-5-(4-hydroxy-3-methoxyphenyl)valeramide (a compound of the present invention) as a pale yellow oil, which had the following physiochemical properties:

Proton nuclear magnetic resonance spectrum (δ ppm in CDCl₃):
0.87 (3H, d, J=6 Hz),
0.9–2.0 (13H, m),
2.08 (2H, t, J=7 Hz),
2.49 (2H, t, J=7 Hz), 3.62 (1H, m),
3.87 (3H, s), 5.21 (1H, m),
6.6–6.9 (3H, m)
MS [(M+H)+]: 320
HRMS (C₁₉H₃₀NO₃):
Theoretical value: 320.22257.
Measured value: 320.22214.

EXAMPLE 119

Alkylation

Using 2.3 g of N-(trans-4-methylcyclohexyl)-5-(4-hydroxy-3-methoxyphenyl)valeramide (Example 118), 100 ml of methylisobutylketone, 5 g of potassium carbonate, and 4 ml of 1-bromo-2-chloroethane, a reaction similar to that conducted in Example 106 was carried out. As a result, 2.1 g of N-(trans-4-methylcyclohexyl)-5-[4-(2-chloroethoxy)-3-methoxyphenyl]valeramide (a compound of the present invention) was obtained as a pale yellow oil, which had the following physiochemical properties:

Proton nuclear magnetic resonance spectrum (δ ppm in CDCl₃):
0.87 (3H, d, J=6 Hz),
0.9–2.0 (11H, m),
2.07 (2H, t, J=7 Hz),
2.50 (2H, t, J=7 Hz), 3.66 (1H, m),
3.81 (2H, t, J=7 Hz), 3.85 (3H, s),
4.06 (2H, t, J=7 Hz), 5.24 (1H, m),
6.6–6.9 (3H, m)
MS [(M+H)+]: 382
HRMS (C₂₁H₃₃NO₃Cl):
Theoretical value: 382.21490.
Measured value: 382. 21480.

EXAMPLE 120

Amination and Conversion into Non-toxic Salt 40 ml of a 50% aqueous dimethylamine solution was added to a solution of 2.1 g of N-(trans-4-methylcyclohexyl)-5-[4-(2-chloroethoxy)-3-methoxyphenyl]valeramide (Example 119) in 50 ml of methylisobutylketone. The solution was reacted for 18 hours by heating to 110° C. in a closed system. After reaction, 200 ml of an aqueous sodium chloride solution and 100 ml of methylene chloride were added to the reaction solution, which was then subjected to extraction. The aqueous layer was extracted twice with 100 ml of methylene chloride. The organic layer obtained was washed twice with an aqueous sodium chloride solution and dried over magnesium sulfate. Thereafter, the solvent was removed in vacuo, yielding 1.54 g 10 of N-(trans-4-methylcyclohexyl)-5-[4-(2-dimethylaminoethoxy)-3-methoxyphenyl]valeramide (a compound of the present invention) as a pale yellow oil, which had the following physiochemical properties:

Proton nuclear magnetic resonance spectrum (δ ppm in CDCl₃):
0.86 (3H, d, J=6 Hz),
0.9–2.0 (11H, m),
2.08 (2H, t, J=7 Hz), 2.34 (6H, s), 2.37 (2H, t, J=7 Hz),
2.48 (2H, t, J=7 Hz), 3.68 (1H, m),
3.86 (3H, s), 4.05 (2H, t, J=7 Hz),
5.24 (1H, m), 6.6–6.9 (3H, m)
MS [(M+H)+]: 391
HRMS ($C_{23}H_{39}N_2O_3$):
Theoretical value: 391.29607.
Measured value: 391.29669.

The compound described above was reacted in the ordinary method, converting it into N-(trans-4-methylcyclohexyl)-5-[4-(2-dimethylaminoethoxy)-3-methoxyphenyl]valeramide hydrochloride, which had the following physiochemical properties:

Proton nuclear magnetic resonance spectrum (δ ppm in $D_2O$):
0.84 (3H, d, J=6 Hz),
0.9–2.0 (11H, m),
2.06 (2H, t, J=7 Hz),
2.36 (2H, t, J=7 Hz), 3.66 (1H, m),
3.72 (2H, t, J=7 Hz), 3.84 (3H, s),
4.03 (2H, t, J=7 Hz),
4.19 (2H, t, J=7 Hz),
6.5–6.9 (3H, m)
MS [(M-Cl)+]: 391
HRMS ($C_{23}H_{39}N_2O_3$):
Theoretical value: 391.29607.
Measured value: 391.29563.

EXAMPLE 121

Esterification and Amidation, and Hydrolysis

A solution of 2.9 g of 4-acetoxy-3,5-dimethoxycinnamic acid derived from 3,5-dimethoxy-4-hydroxycinnamic acid by the acetylation thereof, 2.8 ml of diethyl chlorophosphate and 3.9 ml of triethylamine, mixed in 60 ml of methylene chloride, was stirred for 1 hours at room temperature. Next, 2 g of trans-4-methylcyclohexylammonium chloride and 0.6 g of 4-dimethylaminopiridine were added under ice-cooling to the solution. The solution was reacted for 4 hours at room temperature. Then, the solvent was removed in vacuo, and 100 ml of methanol and 5 g of potassium carbonate were added to the residue, and the solution was reacted for 2 hours.

After reaction, 2N hydrochloric acid was added to the reaction solution, acidifying the solution. The solution was extracted three times with 100 ml of ethyl acetate. The organic layer obtained was washed twice with an aqueous sodium hydrogencarbonate solution and twice with an aqueous sodium chloride solution, and was dried over magnesium sulfate. Then, the solvent was removed in vacuo, yielding 3.48 g of N-(trans-4- methylcyclohexyl)-3,5-dimethoxy-4-hydroxycinnamamide (a compound of the present invention) as a pale yellow oil, which had the following physiochemical properties:

Proton nuclear magnetic resonance spectrum (δ ppm in DMSO-$d_6$):
0.86 (3H, d, J=6 Hz),
0.9–1.9 (9H, m), 3.53 (1H, m),
3.79 (6H, s),
6.41 (1H, d, J=16 Hz),
6.83 (2H, s),
7.25 (1H, d, J=16 Hz),
7.77 (1H, d, J=8 Hz)
MS (M+): 319

EXAMPLE 122

Esterification and Amidation, and Hydrolysis

Using 2.7 g of 4-acetoxy-3-methoxybenzoic acid derived from vanillic acid by the acetylatin thereof, 2.8 ml of diethyl chlorophosphate, 3.9 ml of triethylamine, 2 g of trans-4-methylcyclohexylammmonium chloride, 60 ml of methylene chloride, 0.6 g of 4-dimethylaminopyridine, 100 ml of methanol, and 5 g of potassium carbonate, a reaction similar to that conducted in Example 121 was carried out. As a result, 3.04 g of N-(trans-4-methylcyclohexyl)vanilloylamide (a compound of the present invention) as a pale yellow oil, which had the following physiochemical properties:

Proton nuclear magnetic resonance spectrum (δ ppm in $CDCl_3$):
0.90 (3H, d, J=6 Hz),
0.9–2.1 (9H, m), 3.86 (1H, m),
3.93 (3H, s), 5.86 (1H, m),
6.01 (1H, br),
6.87 (1H, d, J=8 Hz),
7.13 (1H, dd, J=6, 2 Hz),
7.43 (1H, d, J=2 Hz)
MS (M+): 263

EXAMPLE 123

Esterification and Amidation, and Hydrolysis 2.7 g of 4-acetoxycinnamic acid derived from p-coumaric acid by the acetylation thereof, 2.8 ml of diethyl chlorophosphate, 3.9 ml of triethylamine, 2 g of trans-4-methylcyclohexylammmonium chloride, 60 ml of methylene chloride, 0.6 g of 4-dimethylaminopyridine, 100 ml of methanol, and 5 g of potassium carbonate, a reaction similar to that conducted in Example 121 was carried out. The product obtained was recrystallized from methylene chloride/hexane, yielding 2.83 g of N-(trans-4-methylcyclohexyl)-4-hydroxycinnamamide (a compound of the present invention) as white crystal, which had the following physiochemical properties:

Proton nuclear magnetic resonance spectrum (δ ppm in DMSO-$d_6$):
0.86 (3H, d, J=6 Hz),
0.9–1.9 (9H, m), 4.58 (1H, m),
6.34 (1H, d, J=16 Hz),
6.34 (1H, d, J=9 Hz),
6.76 (2H, d, J=9 Hz),
7.26 (1H, d, J=16 Hz),
7.34 (2H, d, J=9 Hz),
7.77 (1H, d, J=8 Hz)
MS (M+): 259

EXAMPLE 124

Esterification and Amidation

Using 2.5 g of 3,4-methylenedioxycinnamic acid, 2.8 ml of diethyl chlorophosphate, 3.9 ml of triethylamine, 60 ml of methylene chloride, 2 g of trans-4-methylcyclohexylammmonium chloride, and 0.6 g of 4-dimethylaminopyridine, a reaction similar to that conducted in Example 81 was carried out. The product obtained was recrystallized from methylene chloride/hexane, yielding 3.11 g of N-(trans-4-methylcyclohexyl)-3,4-methylenedioxycinnamamide (a compound of the present invention) as white crystal, which had the following physiochemical properties:

Proton nuclear magnetic resonance spectrum (δ ppm in DMSO-$d_6$):

0.86 (3H, d, J=6 Hz),
0.9–1.9 (9H, m), 3.52 (1H, m),
6.05 (2H, s),
6.39 (1H, d, J=16 Hz),
6.90 (1H, d, J=8 Hz),
7.01 (1H, d, J=2 Hz),
7.06 (1H, dd, J=6, 2 Hz),
7.26 (1H, d, J=16 Hz)
MS (M+): 287

EXAMPLE 125

Esterification and Amidation

Using 2.7 g of 3,4-dimethoxycinnamic acid, 2.8 ml of diethyl chlorophosphate, 3.9 ml of triethylamine, 2 g of trans-4-methylcyclohexylammmonium chloride, 60 ml of methylene chloride, and 0.6 g of 4-dimethylaminopyridine, a reaction similar to that conducted in Example 81 was carried out. The product obtained was recrystallized from methylene chloride/hexane, yielding 2.83 g of N-(trans-4-methylcyclohexyl)-3,4-dimethoxycinnamamide (a compound of this invention) as white crystal, which had the following physiochemical properties:

Proton nuclear magnetic resonance spectrum ($\delta$ ppm in DMSO-$d_6$):
0.86 (3H, d, J=6 Hz),
0.9–1.9 (9H, m),
3.58 (1H, m), 3.78 (3H, s),
3.79 (3H, s),
6.44 (1H, d, J=16 Hz),
6.95 (1H, d, J=8 Hz),
7.11 (1H, dd, J=6, 2 Hz),
7.13 (1H, s),
7.29 (1H, d, J=16 Hz)
MS (M+): 303

EXAMPLE 126

Esterification and Amidation

Using 3.4 g of 3,4-diacetoxycinnamic acid derived from caffeic acid by the acetylation thereof, 2.8 ml of diethyl chlorophosphate, 3.9 ml of triethylamine, 2 g of trans-4-methylcyclohexylammmonium chloride, 60 ml of methylene chloride, and 0.6 g of 4-dimethylaminopyridine, a reaction similar to that conducted in Example 81 was carried out. The product obtained was recrystallized from methylene chloride/hexane, yielding 3.19 g of N-(trans-4-methylcyclohexyl)-3,4-diacetoxycinnamamide (a compound of the present invention) as white crystal, which had the following physiochemical properties:

Proton nuclear magnetic resonance spectrum ($\delta$ ppm in CDCl$_3$):
0.85 (3H, d, J=6 Hz),
0.9–1.8 (9H, m), 2.30 (6H, s),
3.60 (1H, m), 5.41 (1H, m),
6.80 (1H, d, J=16 Hz),
6.88 (1H, d, J=8 Hz),
7.0–7.2 (2H, m),
7.40 (1H, d, J=16 Hz)
MS (M+): 359

EXAMPLE 127

Esterification and Amidation, and Hydrolysis

Using 2.9 g of (4-acetoxy-3-methoxyphenyl)acetic acid derived from homovanillic acid by the acetylation thereof, 2.8 ml of diethyl chlorophosphate, 3.9 ml of triethylamine, 60 ml of methylene chloride, 2 g of trans-4-methylcyclohexylammmonium chloride, 0.6 g of 4-dimethylaminopyridine, 100 ml of methanol, and 5 g of potassium carbonate, a reaction similar to that conducted in Example 121 was carried out. The product obtained was recrystallized from methylene chloride/hexane, yielding 1.5 g of N-(trans-4-methylcyclohexyl)-2-(4-hydroxy-3-methoxyphenyl)acetamide (a compound of the present invention) as pale yellowish white crystal, which had the following physiochemical properties:

Proton nuclear magnetic resonance spectrum ($\delta$ ppm in CDCl$_3$):
0.84 (3H, d, J=6 Hz),
0.9–2.0 (9H, m), 3.46 (2H, s),
3.68 (1H, m), 3.88 (3H, s),
5.19 (1H, m), 6.7–6.9 (3H, m)
MS [(M+H)+]: 278
HRMS (C$_{16}$H$_{24}$NO$_3$):
Theoretical value: 278.17562.
Measured value: 278.17614.

EXAMPLE 128

Alkylation

Using 1.5 g of N-(trans-4-methylcyclohexyl)-2-(4-hydroxy-3-methoxyphenyl)acetamide (Example 127), 100 ml of methylisobutylketone, 5 g of potassium carbonate, and 4 ml of 1-bromo-2-chloroethane, a reaction similar to that conducted in Example 106 was carried out. As a result, 1.38 g of N-(trans-4-methylcyclohexyl)-2-[4-(2-chloroethoxy)-3-methoxyphenyl]acetamide (a compound of the present invention) was obtained as a pale yellowish white crystal, which had the following physiochemical properties:

Proton nuclear magnetic resonance spectrum ($\delta$ ppm in CDCl$_3$):
0.85 (3H, d, J=6 Hz),
0.9–2.0 (9H, m), 3.48 (2H, s),
3.54 (1H, m), 3.80 (2H, t, J=7 Hz),
3.86 (3H, s), 4.24 (2H, t, J=7 Hz),
5.16 (1H, m), 6.7–6.9 (3H, m)
MS [(M+H)+]: 340
HRMS (C$_{18}$H$_{27}$NO$_3$Cl):
Theoretical value: 340.16795.
Measured value: 340.16765.

EXAMPLE 129

Amidation and Conversion into Non-Toxic Salt

Using 1.38 g of N-(trans-4-methylcyclohexyl)-2-[4-(2-chloroethoxy)-3-methoxyphenyl]acetamide (Example 128), 50 ml of methylisobutylketone, and 40 ml of 50% aqueous dimethylamine solution, a reaction similar to that conducted in Example 107 was carried out. As a result, 1.08 g of N-(trans-4-methylcyclohexyl)-2-[4-(2-dimethylaminoethoxy)-3-methoxyphenyl]acetamide (a compound of the present invention) was obtained as pale yellowish white crystal, which had the following physiochemical properties:

Proton nuclear magnetic resonance spectrum ($\delta$ ppm in CDCl$_3$):
0.85 (3H, d, J=6 Hz),
0.9–1.9 (9H, m), 2.37 (6H, s),
2.41 (2H, t, J=7 Hz), 3.47 (2H, s),
3.64 (1H, m), 3.84 (3H, s),
4.09 (2H, t, J=7 Hz), 5.18 (1H, m),
6.7–6.9 (3H, m)
Ms [(M+H)+]: 349
HRMS (C$_{20}$H$_{33}$N$_3$O$_3$):

Theoretical value: 349.24912.
Measured value: 349.24920.

The compound described above was reacted in the ordinary method, converting it into N-(trans-4-methylcyclohexyl)-2-[4-(2-dimethylaminoethoxy)-3-methoxyphenyl]acetamide hydrochloride, which had the following physiochemical properties:

Proton nuclear magnetic resonance spectrum ($\delta$ ppm in $D_2O$):
0.86 (3H, d, J=6 Hz),
0.9–1.9 (9H, m),
2.91 (2H, t, J=7 Hz), 3.01 (6H, s),
3.61 (2H, s), 3.63 (1H, m),
3.83 (3H, s), 4.21 (2H, t, J=7 Hz),
6.6–6.9 (3H, m)
MS [(M-Cl)+]: 349
HRMS ($C_{20}H_{33}N_2O_3$):
Theoretical value: 349.24912.
Measured value: 349.24922.

EXAMPLE 130

Esterification and Amidation

Using 3.1 g of 4-acetoxy-3-methoxycinnamic acid, 2.8 ml of diethyl chlorophosphate, 3.9 ml of triethylamine, 100 ml of methylene chloride, 2 g of trans-4-methylcyclohexylammmonium chloride, and 0.6 g of 4-dimethylaminopyridine, a reaction similar to that conducted in Example 104 was carried out. As a result, 3.7 g of N-(trans-4-methylcyclohexyl)-4-acetoxy-3-methoxycinnamamide (a compound of the present invention) was obtained as white crystal, which had the following physiochemical properties:

Proton nuclear magnetic resonance spectrum ($\delta$ ppm in $CDCl_3$):
0.89 (3H, d, J=6 Hz),
1.0–2.1 (9H, m),
2.31 (3H, s), 3.83 (1H, m),
3.84 (3H, s), 5.46 (1H, m),
6.25 (1H, d, J=16 Hz),
6.7–7.2 (3H, m),
7.51 (1H, d, J=16 Hz)
$IR_{max}$ (KBr, $cm^{-1}$): 3286, 2940, 1766, 1653
MS (M+): 331
Elemental analysis ($C_{19}H_{25}NO_4$):
Theoretical value; C: 68.86, H: 7.60, N: 4.23.
Measured value; C: 68.81, H: 7.50, N: 4.26.

EXAMPLE 131

Hydrolysis and Conversion into Non-toxic Salt

Using 3.7 g of N-(trans-4-methylcyclohexyl)-4-acetoxy-3-methoxycinnamamide (Example 130), 100 ml of methanol, and 5 g of potassium carbonate, a reaction similar to that conducted in Example 105 was carried out. As a result, 2.75 g of N-(trans-4-methylcyclohexyl)-4-hydroxy-3-methoxycinnamamide (a compound of the present invention) was obtained as white crystal, which had the following physiochemical properties:

Melting point: 208.5°–209.2° C.
Proton nuclear magnetic resonance spectrum ($\delta$ ppm in DMSO-$d_6$):
0.86 (3H, d, J=6 Hz),
0.9–1.9 (9H, m), 3.56 (1H, m),
3.80 ( 3H, s),
6.37 (1H, d, J=16 Hz),
6.76 (1H, d, J=8 Hz),
6.94 (1H, dd, J=6, 2 Hz),
7.09 (1H, d, J=2 Hz),
7.25 (1H, d, J=16 Hz),
7.75 (1H, d, J=8 Hz), 9.35 (1H, s)
$IR_{max}$ (KBr, $cm^{-1}$): 3256, 2953, 1669
MS (M+): 289
Elemental analysis ($C_{17}H_{23}NO_3$):
Theoretical value; C: 70.56, H: 8.01, N: 4.84.
Measured value; C: 70.66, H: 7.99, N: 5.00.

The compound described above was reacted in the ordinary method, converting it into sodium N-(trans-4-methylcyclohexyl)-3-methoxy-4-oxidocinnamamide, which had the following physiochemical properties:

Proton nuclear magnetic resonance spectrum ($\delta$ ppm in $D_2O$):
0.84 (3H, d, J=6 Hz),
0.9–2.0 (9H, m), 3.58 (1H, m),
3.80 (3H, s),
6.23 (1H, d, J=16 Hz),
6.59 (1H, d, J=8 Hz),
7.06 (1H, d, J=8 Hz), 7.10 (1H, s),
7.35 (1H, d, J=16 Hz)
MS [(M+Na)+]: 334, [(M+H)+]: 312
HRMS ($C_{17}H_{22}NO_3Na_2$):
Theoretical value: 334. 13957.
Measured value: 334. 13870.

EXAMPLE 132

Alkylation

Using 5 g of N-(trans-4-methylcyclohexyl)-4-hydroxy-3-methoxycinnamamide (Example 131), 120 ml of methylisobutylketone, 3.5 g of potassium carbonate, and 3.2 ml of 1-bromo-5-chloropentane, a reaction similar to that conducted in Example 106 was carried out. As a result, 5.86 g of N-(trans-4-methylcyclohexyl)-4-(5-chloropentyloxy)-3-methoxycinnamamide (a compound of the present invention) was obtained as white crystal, which had the following physiochemical properties:

Proton nuclear magnetic resonance spectrum ($\delta$ ppm in $CDCl_3$):
0.89 (3H, d, J=6 Hz),
1.0–2.1 (15H, m),
3.53 (2H, t, J=7 Hz), 3.85 (1H, m),
3.87 (3H, s), 4.01 (2H, t, J=7 Hz),
5.40 (1H, m),
6.19 (1H, d, J=16 Hz),
6.81 (1H, d, J=8 Hz),
7.0–7.1 (2H, m),
7.49 (1H, d, J=16 Hz)
MS [(M+H)+]: 394

EXAMPLE 133

Alkylation

Using 5 g of of N-(trans-4-methylcyclohexyl)-4-hydroxy-3-methoxycinnamamide (Example 131), 120 ml of methylisobutylketone, 3.5 g of potassium carbonate, and 2.9 ml of 1-bromo-4-chlorobutane, a reaction similar to that conducted in Example 106 was carried out. As a result, 5.79 g of N-(trans-4-methylcyclohexyl)-4-(4-chlorobutoxy ) - 3 -methoxycinnamamide ( a compound of the present invention) was obtained as white crystal, which had the following physiochemical properties:

Proton nuclear magnetic resonance spectrum ($\delta$ ppm in $CDCl_3$):
0.89 (3H, d, J=6 Hz),
1.0–2.1 (13H, m),
3.60 (2H, t, J=7 Hz), 3.86 (1H, m), 3.87 (3H, s), 4.02 (2H, t, J=7 Hz),
5.42 (1H, m),
6.20 (1H, d, J=16 Hz),
6.81 (1H, d, J=8 Hz),
7.0–7.1 (2H, m),
7.49 (1H, d, J=16 Hz)
MS [(M+H)+]: 380

EXAMPLE 134

Alkylation

Using 5 g of of N-(trans-4-methylcyclohexyl)-4-hydroxy-3-methoxycinnamamide (Example 131), 120 ml of methylisobutylketone, 3.5 g of potassium carbonate, and 2.4 ml of 1-bromo-3-chloropropane, a reaction similar to that conducted in Example 106 was carried out. As a result, 5.63 g of N-(trans-4-methylcyclohexyl)-4-(3-chloropropoxy)-3-methoxycinnamamide (a compound of the present invention) was obtained as white crystal, which had the following physiochemical properties:

Proton nuclear magnetic resonance spectrum (δ ppm in CDCl$_3$):
0.89 (3H, d, J=6 Hz),
1.0–2.1 (9H, m),
3.73 (2H, t, J=7 Hz), 3.86 (1H, m),
3.87 (3H, s), 4.16 (2H, t, J=7 Hz),
5.42 (1H, m),
6.20 (1H, d, J=16 Hz),
6.85 (1H, d, J=8 Hz),
7.0–7.1 (2H, m),
7.49 (1H, d, J=16 Hz)
MS [(M+H)+]: 366

EXAMPLE 135

Amidation and Conversion into Non-toxic Salt

Using 5 g of N-(trans-4-methylcyclohexyl)-4-(5-chloropentyloxy)-3-methoxycinnamamide (Example 132), 100 ml of methylisobutylketone, and 150 ml of 50% aqueous dimethylamine solution, a reaction similar to that conducted in Example 107 was carried out. As a result, 3.17 g of N-(trans-4-methylcyclohexyl)-4-(5-dimethylaminopentyloxy)-3-methoxycinnamamide (a compound of the present invention) was obtained as white crystal, which had the following physiochemical properties:

Proton nuclear magnetic resonance spectrum (δ ppm in CDCl$_3$):
0.89 (3 H, d, J=6 Hz),
1.0–2.1 (15 H, m), 2.22 (6 H, s),
2.23 (2 H, t, J=7 Hz), 3.81 (1 H, m),
3.87 (3 H, s), 4.00 (2 H, t, J=7 Hz),
5.41 (1 H, m),
6.19 (1 H, d, J=16 Hz),
6.81 (1 H, d, J=8 Hz),
7.0–7.1 (2 H, m),
7.49 (1 H, d, J=16 Hz)
MS [(M+H)+]:403

The compound described above was reacted in the ordinary method, converting it into sodium N-(trans-4-methylcyclohexyl)-4-(5-dimethylaminopentyloxy)-3-methoxycinnamamide hydrochloride, which had the following physiochemical properties:

Proton nuclear magnetic resonance spectrum (δ ppm in D$_2$O):
0.88 (3 H, d, J=6 Hz),
0.9–2.1 (15 H, m),
2.88 (2 H, t, J=7 Hz), 3.00 (6 H, s),
3.82 (1 H, m), 3.88 (3 H, s),
4.19 (2 H, t, J=7 Hz),
6.16 (1 H, d, J=16 Hz),
6.79 (1 H, d, J=8 Hz),
6.9–7.1 (2 H, m),
7.41 (1 H, d, J=16 Hz)
MS [(M-Cl)+]:403
HRMS (C$_{24}$H$_{39}$N$_2$O$_3$):
Theoretical value: 403.29607.
Measured value: 403.29792.

EXAMPLE 136

Amidation and Conversion into Non-toxic Salt

Using 5 g of N-(trans-4-methylcyclohexyl)-4-(4-chlorobutoxy)-3-methoxycinnamamide (Example 133), 100 ml of methylisobutylketone, and 150 ml of 50% aqueous dimethylamine solution, a reaction similar to that conducted in Example 107 was carried out. As a result, 2.01 g of N-(trans-4-methylcyclohexyl)-4-(4-dimethylaminobutoxy)-3-methoxycinnamamide (a compound of the present invention) was obtained as light-greenish white crystal, which had the following physiochemical properties:

Proton nuclear magnetic resonance spectrum (δ ppm in CDCl$_3$):
0.89 (3 H, d, J=6 Hz),
1.0–2.2 (13 H, m), 2.29 (6 H, s),
2.32 (2 H, t, J=7 Hz), 3.84 (1 H, m),
3.86 (3 H, s), 4.04 (2 H, t, J=9 Hz),
5.41 (1 H, m),
6.19 (1 H, d, J=16 Hz),
6.80 (1 H, d, J=8 Hz),
7.0–7.1 (2 H, m),
7.49 (1 H, d, J=16 Hz)
MS [(M+H)+]:389
HRMS (C$_{23}$H$_{37}$N$_2$O$_3$):
Theoretical value: 389.28042.
Measured value: 389.28028.

The compound described above was reacted in the ordinary method, converting it into N -(trans-4-methylcyclohexyl)-4-(4-dimethylaminobutoxy)-3methoxycinnamamide hydrochloride, which had the following physiochemical properties:

Proton nuclear magnetic resonance spectrum (δ ppm in D$_2$O):
0.88 (3 H, d, J=6 Hz),
0.9–2.3 (13 H, m),
2.86 (2 H, t, J=7 Hz), 2.99 (6 H, s),
3.83 (1 H, m), 3.88 (3 H, s),
4.22 (2 H, t, J=7 Hz),
6.16 (1 H, d, J=16 Hz),
6.9–7.1 (3 H, m),
7.42 (1 H, d, J=16 Hz)
MS [(M-Cl)+]:389
HRMS (C$_{23}$H$_{37}$N$_2$O$_3$):
Theoretical value: 389.28042.
Measured value: 389.27942.

EXAMPLE 137

Reduction and Conversion into Non-toxic Salt

Using 5 g of N-(trans-4-methylcyclohexyl) -4-(3-chloropropoxy)-3-methoxycinnamamide (Example 134), 100 ml of methylisobutylketone, and 150 ml of a 50% aqueous dimethylamine solution, a reaction similar to that conducted in Example 107 was carried out. As a result, 4.61 g of N-(trans-4-methylcyclohexyl)-4-(3-dimethylaminopropoxy)-3-methoxycinnamamide (a compound of the present invention) was obtained as white crystal, which had the following physiochemical properties:

Proton nuclear magnetic resonance spectrum (δ ppm in CDCl₃):
0.89 (3 H, d, J=6 Hz),
1.0–2.1 (11 H, m), 2.27 (6 H, s),
2.45 (2 H, t, J=7 Hz), 3.86 (1 H, m),
3.87 (3 H, s), 4.06 (2 H, t, J=7 Hz),
5.41 (1 H, m),
6.18 (1 H, d, J=16 Hz),
6.84 (1 H, d, J=8 Hz),
7.0–7.1 (2 H, m),
7.49 (1 H, d, J=16 Hz)
MS [(M+H)+]:375

The compound described above was reacted in the ordinary method, converting it into N-(trans-4-methylcyclohexyl)-4-(3-dimethylaminopropoxy)-3-methoxycinnamamide hydrochloride, which had the following physiochemical properties:

Proton nuclear magnetic resonance spectrum (δ ppm in D₂O):
0.88 (3 H, d, J=6 Hz),
0.9–2.1 (11 H, m),
3.00 (6 H, s), 3.87 (1 H, m),
3.91 (2 H, t, J=7 Hz), 3.88 (3 H, s),
4.20 (2 H, t, J=7 Hz),
6.16 (1 H, d, J=16 Hz),
6.9–7.1 (3 H, m),
7.41 (1 H, d, J=16 Hz)
MS [(M-Cl)+]:375
HRMS (C₂₂H₃₅N₂O₃):
Theoretical value: 375.26477.
Measured value: 375.26475.

EXAMPLE 138

Alkylation

Using 5 g of N-(tans-4-methylcyclohexyl)-4-hydroxy-3-methoxycinnamamide (Example 131), 120 ml of methylisobutylketone, 3.5 g of potassium carbonate, and 2.1 ml of 1-bromo-2-chloroethane, a reaction similar to that conducted in Example 106 was carried out. As a result, 5.48 g of N-(trans-4-methylcyclohexyl)-4-(2-chloroethoxy)-3-methoxycinnamamide (a compound of the present invention) was obtained as white crystal, which had the following physiochemical properties:

Proton nuclear magnetic resonance spectrum (δ ppm in CDCl₃):
0.89 (3 H, d, J=6 Hz),
1.0–2.1 (9 H, m),
3.81 (2 H, t, J=7 Hz), 3.88 (3 H, s),
4.26 (2 H, t, J=7 Hz),
5.41 (1 H, d, J=8 Hz),
6.21 (1 H, d, J=16 Hz),
6.85 (1 H, d, J=8 Hz),
7.0–7.1 (2 H, m),
7.49 (1 H, d, J=16 Hz)
MS [(M+H)+]:352

EXAMPLE 139

Amination and Conversion into Non-toxic Salts

Using 5 g of N-(trans-4-methylcyclohexyl)-4-(2-chloroethoxy)-3-methoxycinnamamide (Example 138), 100 ml of methylisobutylketone, and 150 ml of a 50% aqueous dimethylamine solution, a reaction similar to that conducted in Example 107 was carried out. As a result, 3.59 g of N-(trans-4-methylcyclohexyl)-4-(2-dimethylaminoethoxy)-3-methoxycinnamamide (a compound of the present invention) was obtained as white crystal, which had the following physiochemical properties:

Proton nuclear magnetic resonance spectrum (δ ppm in DMSO—d₆):
0.86 (3 H, d, J=6 Hz),
0.9–1.9 (9 H, m), 2.22 (6 H, s),
2.50 (2 H, t, J=7 Hz), 3.52 (1 H, m),
3.79 (3 H, s), 4.02 (2 H, t, J=7 Hz),
6.43 (1 H, d, J=16 Hz),
6.9–7.2 (3 H, m),
7.28 (1 H, d, J=16 Hz),
7.81 (1 H, d, J=8 Hz)
MS [(M+H)+]:361

The compound described above was reacted in the ordinary method, converting it into N-(trans-4-methylcyclohexyl)-4-(2-dimethylaminoethoxy)-3-methoxycinnamamide hydrochloride, which had the following physiochemical properties:

Proton nuclear magnetic resonance spectrum (δ ppm in D₂O):
0.86 (3 H, d, J=6 Hz),
0.9–2.0 (9 H, m),
2.98 (6 H, s), 3.58 (1 H, m),
3.60 (2 H, t, J=7 Hz), 3.76 (3 H, s),
4.27 (2 H, t, J=7 Hz),
6.49 (1 H, d, J=16 Hz),
6.8–7.2 (3 H, m),
7.35 (1 H, d, J=16 Hz)
MS [(M-Cl)+]:361
HRMS (C₂₁H₃₃N₂O₃):
Theoretical value: 361.24912.
Measured value: 361.24904.

The compound described above was reacted in the ordinary method, converting it into N-(trans-4methylcyclohexyl)-4-(2-dimethylaminoethoxy)-3methoxycinnamamide maleic acid salt, which had the following physiochemical properties:

Proton nuclear magnetic resonance spectrum (δ ppm in CDCl₃):
0.88 (3 H, d, J=6 Hz),
0.9–2.1 (9 H, m),
2.98 (6 H, s), 3.49 (2 H, t, J=5 Hz),
3.7–3.9 (1 H, m), 3.84 (3 H, s),
4.37 (2 H, t, J=7 Hz),
5.73 (1 H, d, J=8 Hz),
6.26 (2 H, d, J=1 Hz),
6.28 (1 H, d, J=16 Hz),
6.83 (1 H, d, J=8 Hz), 7.02 (1 H, s),
7.02 (1 H, dd, J=2, 8 Hz),
7.47 (1 H, d, J=16 Hz)

The compound described above was reacted in the ordinary method, converting it into N-(trans-4-methylcyclohexyl)-4-(2-dimethylaminoethoxy)-3-methoxycinnamamide d-tartaric acid salt, which had the following physiochemical properties:

Proton nuclear magnetic resonance spectrum (δ ppm in CD₃OD):
0.90 (3 H, d, J=6 Hz),
0.9–2.0 (9 H, m),
2.89 (6 H, s), 3.31 (2 H, t, J=5 Hz),
3.6–3.8 (1 H, m), 3.89 (3 H, s),
4.31 (2 H, t, J=7 Hz), 4.85 (2 H, s),
6.44 (1 H, d, J=16 Hz),
7.00 (1 H, d, J=8 Hz),
7.11 (1 H, dd, J=2, 8 Hz),
7.16 (1 H, s), 7.41 (1 H, d, J=16 Hz)

The compound described above was reacted in the ordinary method, converting it into N-(trans-4-methylcyclohexyl)-4-(2-dimethylaminoethoxy)-3-methoxycinnamamide p-toluenesulfonic acid salt, which had the following physiochemical properties:

Proton nuclear magnetic resonance spectrum (δ ppm in CD$_3$OD):
0.87 (3 H, d, J=6 Hz),
0.9–2.0 (9 H, m),
2.31 (3 H, s), 2.95 (6 H, d, J=4 Hz),
2.4–2.5 (2 H, m), 3.7–3.9 (1 H, m),
3.74 (3 H, s), 4.2–4.3 (2 H, m),
6.49 (1 H, d, J=16 Hz),
6.67 (1 H, d, J=8 Hz),
6.96 (1 H, d, J=2, 8 Hz), 7.13 (1 H, s),
7.45 (1 H, d, J=16 Hz),
7.69 (2 H, d, J=8 Hz)

The compound described above was reacted in the ordinary method, converting it into N-(trans-4-methylcyclohexyl)-4-(2-dimethylaminoethoxy)-3-methoxycinnamamide salicylic acid salt, which had the following physiochemical properties:

Proton nuclear magnetic resonance spectrum (δ ppm in CD$_3$OD):
0.89 (3 H, d, J=6 Hz),
0.9–2.1 (9 H, m)
3.7–3.9 (1 H, m), 3.84 (3 H, s),
5.46 (1 H, d, J=8 Hz),
6.21 (1 H, d, J=16 Hz),
7.00 (1 H, d, J=2 Hz),
7.03 (1 H, d, J=8 Hz),
7.3–7.4 (2 H, m)
7.49 (1 H, d, J=16 Hz),
7.85 (1 H, dd, J=2, 8 Hz)

EXAMPLE 140

Amination and Conversion into Non-toxic Salt

Using 5 g of N-(trans-4-methylcyclohexyl)-4-(2-chloroethoxy)-3-methoxycinnamamide (Example 138), 100 ml of methylisobutylketone, and 50 ml of diethylamine, a reaction similar to that conducted in Example 107 was carried out. As a result, 4.75 g of N-(trans-4-methylcyclohexyl)-4-(2-diethylaminoethoxy)-3-methoxycinnamamide (a compound of the present invention) was obtained as white crystal, which had the following physiochemical properties:

Proton nuclear magnetic resonance spectrum (δ ppm in CDCl$_3$):
0.89 (3 H, d, J=6 Hz),
1.0–2.1 (9 H, m)
1.04 (3 H, d, J=7 Hz),
2.60 (2 H, q, J=7 Hz),
2.91 (2 H, t, J=7 Hz), 3.80 (1 H, m),
3.87 (3 H, s), 4.09 (2 H, t, J =7 Hz),
5.38 (1 H, m),
6.19 (1 H, d, J=16 Hz),
6.84 (1 H, d, J=8 Hz),
7.0–7.1 (2 H, m)
7.49 (1 H, d, J=16 Hz)
MS[(M+H)+]:389

The compound described above was reacted in the ordinary method, converting it into N-(trans-4-methylcyclohexyl)-4-(2-dimethylaminoethoxy)-3-methoxycinnamamide hydrochloride, which had the following physiochemical properties:

Proton nuclear magnetic resonance spectrum (δ ppm in D$_2$O):
0.88 (3 H, d, J=6 Hz),
0.9–2.1 (9 H, m),
1.99 (3 H, t, J=7 Hz),
3.22 (2 H, t, J=7 Hz),
3.59 (q, 2 H, J=7 Hz), 3.79 (1 H, m),
3.86 (3 H, s), 4.24 (2 H, t, J=7 Hz),
6.15 (1 H, d, J=16 Hz),
6.79 (1 H, d, J=8 Hz),
6.9–7.1 (2 H, m),
7.46 (1 H, d, J=16 Hz)
MS [(M-Cl)+]:389
HRMS (C$_{23}$H$_{37}$N$_2$O$_3$):
Theoretical value: 389.28042.
Measured value: 389.28018.

EXAMPLE 141

Amination

Using 5 g of N-(trans-4-methylcyclohexyl)-4-(2-chloroethoxy)-3-methoxycinnamamide (Example 138), 100 ml of methylisobutylketone, and 200 ml of 28% ammonia water, a reaction similar to that conducted in Example 107 was carried out. The crystal procipitated was filtered out, yielding 0.9 g of N-(trans-4-methylcyclohexyl)-4-(2-aminoethoxy)-3-methoxycinnamamide (a compound of the present invention) as white crystal, which had the following physiochemical properties:

Proton nuclear magnetic resonance spectrum (δ ppm in DMSO—d$_6$):
0.86 (3 H, d, J=6 Hz),
0.9–1.9 (11 H, m),
2.90 (2 H, t, J=7 Hz), 3.54 (1 H, m),
3.80 (3 H, s), 4.03 (2 H, t, J=7 Hz),
6.45 (1 H, d, J=16 Hz),
6.9–7.2 (3 H, m),
7.28 (1 H, d, J=16 Hz),
7.83 (1 H, d, J=8 Hz)
MS [(M+H)+]:333
HRMS (C$_{19}$H$_{29}$N$_2$O$_3$):
Theoretical value: 333.21782.
Measured value: 333.21761.

EXAMPLE 142

Amination and Conversion into Non-toxic Salt 22 ml of piperidine was added to a solution of 3.9 g of N-(trans-4-methylcyclohexyl)-4-(2-chloroethoxy)-3-methoxycinnamamide (Example 138) in 100 ml of methylisobutylketone. The solution was reacted for 18 hours, while it was refluxed.

After reaction, 200 ml of an aqueous sodium chloride solution and 200 ml of methylene chloride were added to the reaction solution, which was then subjected to extraction. Further, the aqueous layer was extracted twice with 100 ml of methylene chloride. The organic layer obtained was washed twice with an aqueous sodium chloride solution and was dried over magnesium sulfate. Thereafter, the solvent was removed in vacuo. The product obtained was recrystallized from methylene chloride/ether, yielding 3.0 g of N-(trans-4-methylcyclohexyl)-4-(2-piperidinoethoxy)-3-methoxycinnamamide (a compound of the present invention) as white crystal, which had the following physiochemical properties:

Proton nuclear magnetic resonance spectrum (δ ppm in CDCl$_3$):
0.88 (3 H, d, J=6 Hz), 1.0–2.1 (15 H, m), 2.50 (4 H, m),
2.80 (2 H, t, J=7 Hz), 3.86 (1 H, m),
3.87 (3 H, s), 4.14 (3 H, t, J=6 Hz),
5.39 (1 H, m),
6.19 (1 H, d, J=16 Hz),
6.84 (1 H, d, J=8 Hz),
7.0–7.1 (2 H, m),
7.48 (1 H, d, J=16 Hz)
MS [(M+H)+]:401

The compound described above was reacted in the ordinary method, converting it into N-(trans-4-methylcyclohexyl)-4-(2-piperidinoethoxy)-3-methoxycinnamamide hydrochloride, which had the following physiochemical properties:

Proton nuclear magnetic resonance spectrum ($\delta$ ppm in $D_2O$):
0.87 (3 H, d, J=6 Hz),
1.0–2.4 (15 H, m),
3.42 (4 H, m), 3.69 (2 H, t, J=7 Hz),
3.85 (1 H, m), 3.89 (3 H, s),
4.31 (2 H, t, J=7 Hz),
6.21 (1 H, d, J=16 Hz),
6.79 (1 H, d, J=8 Hz),
6.9–7.1 (2 H, m),
7.41 (1 H, d, J=16 Hz)
Ms [(M-Cl)+]:401
HRMS ($C_{24}H_{37}N_2O_3$):
Theoretical value: 401.28377.
Measured value: 401.28051.

EXAMPLE 143

Amination and Conversion into Non-toxic Salt

Using 3.9 g of N-(trans-4-methylcyclohexyl)-4-(2-chloroethoxy)-3-methoxycinnamamide (Example 138) and 18 ml of pyrrolidine, a reaction similar to that conducted in Example 142 was carried out. As a result, 2.68 g of N-(trans-4-methylcyclohexyl)-4-[2-(1-pyrrolidinyl)ethoxy]-3-methoxycinnamamide (a compound of the present invention) was obtained as white crystal, which had the following physiochemical properties:

Proton nuclear magnetic resonance spectrum ($\delta$ ppm in $CDCl_3$):
0.88 (3 H, d, J=6 Hz),
0.9–2.1 (6 H, m), 2.60 (2 H, m),
2.92 (2 H, t, J=6 Hz), 3.87 (3 H, s),
4.14 (2 H, t, J=6 Hz), 5.42 (1 H, m),
6.19 (1 H, d, J=16 Hz),
6.84 (1 H, d, J=8 Hz),
7.0–7.1 (2 H, m),
7.49 (1 H, d, J=16 Hz)
MS [(M+H)+]:387

The compound described above was reacted in the ordinary method, converting it into N-(trans-4-methylcyclohexyl)-4-[2-(1-pyrrolidinyl)ethoxy]-3-methoxycinnamamide hydrochloride, which had the following physiochemical properties:

Proton nuclear magnetic resonance spectrum ($\delta$ ppm in $D_2O$):
0.87 (3 H, d, J=6 Hz),
0.9–2.1 (6 H, m),
3.01 (2 H, t, J=7 Hz), 3.40 (2 H, m),
3.88 (3 H, s), 4.20 (2 H, t, J=7 Hz),
6.23 (1 H, d, J=16 Hz),
6.88 (1 H, d, J=8 Hz),
6.9–7.1 (2 H, m),
7.41 (1 H, d, J=16 Hz)
MS [(M-Cl)+]:387

HRMS ($C_{23}H_{35}N_2O_3$):
Theoretical value: 387.26477.
Measured value: 387.26451.

EXAMPLE 144

Amination and Conversion into Non-toxic Salt

Using 3.9 g of N-(trans-4-methylcyclohexyl)-4-(2-chloroethoxy)-3-methoxycinnamamide (Example 138) and 19 ml of morpholine, a reaction similar to that conducted in Example 142 was carried out. As a result, 3.19 g of N-(trans-4-methylcyclohexyl)-4-(2-morpholinoethoxy)-3-methoxycinnamamide (a compound of the present invention) was obtained as white crystal, which had the following physiochemical properties:

Proton nuclear magnetic resonance spectrum ($\delta$ ppm in $CDCl_3$):
0.88 (3 H, d, J=6 Hz),
1.0–2.1 (9 H, m),
2.56 (4 H, t, J=5 Hz),
2.81 (2 H, t, J=6 Hz),
3.70 (4 H, t, J=5 Hz), 3.86 (3 H, s),
4.14 (2 H, t, J=6 Hz), 5.44 (1 H, m),
6.20 (1 H, d, J=16 Hz),
6.83 (1 H, d, J=8 Hz),
7.0–7.1 (2 H, m),
7.49 (1 H, d, J=16 Hz)
MS [(M+H)+]:403

The compound described above was reacted in the ordinary method, converting it into N-(trans-4-methylcyclohexyl)-4-(2-morpholinoethoxy)-3-methoxycinnamamide hydrochloride, which had the following physiochemical properties:

Proton nuclear magnetic resonance spectrum ($\delta$ ppm in $D_2O$):
0.87 (3 H, d, J=6 Hz),
0.9–2.1 (9 H, m),
2.99 (2 H, t, J=6 Hz),
3.61 (4 H, t, J=5 Hz),
3.74 (4 H, t, J=5 Hz), 3.85 (3 H, s),
4.21 (2 H, t, J=6 Hz),
6.22 (1 H, d, J=16 Hz),
6.86 (1 H, d, J=8 Hz),
6.9–7.1 (2 H, m),
7.41 (1 H, d, J=16 Hz)
MS [(M-Cl)+]:403
HRMS ($C_{23}H_{35}N_2O_4$):
Theoretical value: 403.25969.
Measured value: 403.25999.

EXAMPLE 145

Amination and Conversion into Non-toxic Salts

Using 3.9 g of N-(trans-4-methylcyclohexyl)-4-(2-chloroethoxy)-3-methoxycinnamamide (Example 138) and 24 ml of 1-methylpiperazine, a reaction similar to that conducted in Example 142 was carried out. As a result, 2.24 g of N-(trans-4-methylcyclohexyl)-4-[2-(4-methylpiperazinyl)ethoxy]-3-methoxycinnamamide (a compound of the present invention) was obtained as light-brownish white crystal, which had the following physiochemical properties:

Proton nuclear magnetic resonance spectrum ($\delta$ ppm in $CDCl_3$):
0.89 (3 H, d, J=6 Hz),
1.0–2.1 (9 H, m), 2.25 (3 H, s),
2.4–2.7 (8 H, m),
2.83 (2 H, t, J=6 Hz), 2.85 (1 H, m),
2.86 (3 H, s), 3.43 (2 H, t, J=7 Hz), 5.39 (1 H, d, J=8 Hz),
6.19 (1 H, d, J=16 Hz),
6.83 (1 H, d, J=8 Hz),
7.0–7.1 (2 H, m),
7.49 (1 H, d, J=16 Hz)
MS [(M+H)+]:416

The compound described above was reacted in the ordinary method, converting it into N-(trans-4-methylcyclohexyl)-4-[2-(4-methylpiperazinyl)ethoxy]-3-methoxycinnamamide dihydrochloride, which had the following physiochemical properties:

Proton nuclear magnetic resonance spectrum (δ ppm in D$_2$O):
0.88 (3 H, d, J=6 Hz),
0.9–2.1 (9 H, m),
3.00 (3 H, s), 3.2–3.5 (8 H, m),
3.62 (2 H, t, J=7 Hz), 3.84 (3 H, s),
4.19 (2 H, t, J=7 Hz),
6.22 (1 H, d, J=16 Hz),
6.9–7.1 (3 H, m),
7.41 (1 H, d, J=16 Hz)
MS [(M+H-2HCl)+]:416
HRMS (C$_{24}$H$_{38}$N$_3$O$_3$):
Theoretical value: 416.29132.
Measured value: 416.29158.

The compound described above was reacted in the ordinary method, converting it into N-(trans-4-methylcyclohexyl) -4-[2-(4-methylpiperazinyl)ethoxy]-3-methoxycinnamamide difumaric acid salt, which had the following physiochemical properties:

Proton nuclear magnetic resonance spectrum (δ ppm in CD$_3$OD):
0.90 (3 H, d, J=6 Hz),
1.0–2.0 (9 H, m),
2.80 (3 H, S), 2.9–3.1 (6 H, m),
3.2–3.3 (4 H, m), 3.6 3.8 (1 H, m),
3.86 (3 H, S), 4.17 (2 H, t, J=5 Hz),
6.42 (1 H, d, J=16 Hz),
6.72 (4 H, s),
6.94 (1 H, d, J=8 Hz),
7.08 (1 H, dd, J=2, 8 Hz),
7.13 (1 H, d, J=2 Hz),
7.40 (1 H, d, J=16 Hz)

The compound described above was reacted in the ordinary method, converting it into N-(trans-4-methylcyclohexyl)-4-[2-(4-methylpiperazinyl)ethoxy]-3-methoxycinnamamide disuccinic acid salt, which had the following physiochemical properties:

Proton nuclear magnetic resonance spectrum (δ ppm in CD$_3$OD):
0.90 (3 H, d, J=6 Hz),
1.0–2.0 (9 H, m),
2.73 (8 H, s), 2.9–3.0 (6 H, m),
3.1–3.2 (4 H, m), 3.6–3.8 (1 H, m),
3.86 (3 H, s), 4.16 (2 H, t, J=5 Hz),
6.43 (1 H, d, J=16 Hz),
6.94 (1 H, d, J=8 Hz),
7.08 (1 H, dd, J=2, 8 Hz),
7.13 (1 H, d, J=2 Hz),
7.41 (1 H, d, J=16 Hz)

EXAMPLE 146

Amination and Conversion into Non-toxic Salts

Using 3.9 g of N-(trans-4-methylcyclohexyl)-4-(2-chloroethoxy)-3-methoxycinnamamide (Example 138) and 1.5 g of imidazole, a reaction similar to that conducted in Example 142 was carried out. As a result, 3.38 g of N-(trans-4-methylcyclohexyl)-4-[2-(1-imidazolyl)ethoxy]-3methoxycinnamamide (a compound of the present invention) was obtained as light-brownish white crystal, which had the following physiochemical properties:

Proton nuclear magnetic resonance spectrum (δ ppm in CDCl$_3$):
0.89 (3 H, d, J=6 Hz),
1.0–2.1 (9 H, m), 3.79 (1 H, m),
3.86 (3 H, s), 4.23 (2 H, t, J=7 Hz),
4.34 (2 H, t, J=7 Hz), 5.48 (1 H, m),
6.20 (1 H, d, J=16 Hz),
6.72 (1 H, d, J=9 Hz),
7.0–7.1 (4 H, m),
7.47 (1 H, d, J=16 Hz), 7.65 (1 H, s)
MS [(M+H)+]:384

The compound described above was reacted in the ordinary method, converting it into N-(trans-4-methylcyclohexyl)-4-[2-(1-imidazolyl)ethoxy]-3-methoxycinnamamide hydrochloride, which had the following physiochemical properties:

Proton nuclear magnetic resonance spectrum (δ ppm in D$_2$O):
0.88 (3 H, d, J=6 Hz),
0.9–2.1 (9 H, m),
3.75 (1 H, m), 3.84 (3 H, s),
4.39 (2 H, t, J=7 Hz),
5.21 (2 H, t, J=7 Hz),
6.18 (1 H, d, J=16 Hz),
6.9–7.4 (4 H, m),
7.44 (2 H, d, J=16 Hz), 8.82 (1 H, s)
MS [(M+H-2HCl)+]:384
HRMS (C$_{22}$H$_{30}$N$_3$O$_3$):
Theoretical value: 384.22872.
Measured value: 384.22889.

The compound described above was reacted in the ordinary method, converting it into N-(trans-4-methylcyclohexyl)-4-[2-(1-imidazolyl)ethoxy]-3-methoxycinnamamide d-tartaric acid salt, which had the following physiochemical properties:

Proton nuclear magnetic resonance spectrum (δ ppm in CD$_3$OD):
0.90 (3 H, d, J=6 Hz),
0.9–2.0 (9 H, m),
3.6–3.8 (1 H, m), 3.85 (3 H, s),
4.31 (2 H, t, J=5 Hz), 4.46 (2 H, s),
4.50 (2 H, t, J=5 Hz),
6.42 (1 H, d, J=16 Hz),
6.91 (1 H, d, J=8 Hz),
7.07 (1 H, d, J=8 Hz),
7.14 (1 H, s),
7.39 (1 H, d, J=16 Hz),
7.49 (1 H, s), 8.38 (1 H, s)

The compound described above was reacted in the ordinary method, converting it into N-(trans-4-methylcyclohexyl)-4-[2-(1-imidazolyl)ethoxy]-3-methoxycinnamamide p-toluenesulfonic acid salt, which had the following physiochemical properties:

Proton nuclear magnetic resonance spectrum (δ ppm in CD$_3$OD):
0.90 (3 H, d, J=6 Hz),
0.9–2.0 (9 H, m),
2.35 (3 H, s), 3.6–3.8 (1 H, m),
3.84 (3 H, s), 4.2–4.3 (2 H, m),
4.6–4.7 (2 H, m),
6.45 (1 H, d, J=16 Hz),
6.93 (1 H, d, J=8 Hz),
7.07 (1 H, d, J=8 Hz), 7.1–7.3 (3 H, m),
7.39 (1 H, d, J=16 Hz),
7.56 (1 H, s), 7.6–7.8 (2 H, m),
9.02 (1 H, s)

EXAMPLE 147

Reduction 0.075 g of 10% palladium-carbon was added to a solution of 1.5 g of N-(trans-4-methylcyclohexyl)-4-hydroxy-3-methoxycinnamamide (Example 131) in 100 ml of methanol. The solution was vigorously stirred for 16 hours under normal-pressure hydrogen gas. After reaction, the catalyst was filtered out, and the solvent was removed in vacuo from the flitrate, yielding 1.33 g of N-(trans-4-methylcyclohexyl)-3-(4-hydroxy-3-methoxyphenyl)propionamide (a compound of the present as a colorless oil, which had the following physiochemical properties:

Proton nuclear magnetic resonance spectrum ($\delta$ ppm in DMSO—$d_6$):
0.83 (3 H, d, J=6 Hz),
0.9–1.8 (9 H, m),
2.23 (2 H, t, J=7 Hz),
2.65 (2 H, t, J=7 Hz),
3.73 (3 H, s), 3.84 (1 H, m),
6.53 (1 H, dd, J=6, 2 Hz),
6.62 (1 H, d, J=8 Hz),
6.72 (1 H, d, J=2 Hz),
8.30 (1 H, d, J=8 Hz)
MS (M+):291

EXAMPLE 148

Reduction and Conversion into Non-toxic Salt

Using 1.5 g of N-(trans-4-methylcyclohexyl)-4-(5-dimethylaminopentyloxy)-3-methoxycinnamamide (Example 135), 0.075 g of 10% palladium-carbon, and 100 ml of methanol, a reaction similar to that conducted in Example 147 was carried out. The product obtained was recrystallized from methylene chloride/ether, yielding 1.3 g of N-(trans-4-methylcyclohexyl)-3-[4-(5-dimethylaminopentyloxy)-3-methoxyphenyl]propionamide (a compound of the present invention) as light-greenish white crystal, which had had the following physiochemical properties:

Proton nuclear magnetic resonance spectrum ($\delta$ ppm in CDCl$_3$):
0.86 (3 H, d, J=6 Hz),
0.9–2.0 (15 H, m), 2.22 (6 H, s),
2.24 (2 H, t, J=7 Hz),
2.36 (2 H, t, J=7 Hz),
2.85 (2 H, t, J=7 Hz), 3.64 (1 H, m),
3.82 (3 H, s), 3.94 (2 H, t, J=7 Hz),
5.13 (1 H, m), 6.7–6.9 (3 H, m)
Ms [(M+H)+]:405

The compound described above was reacted in the ordinary method, converting it into N-(trans-4-methylcyclohexyl)-3-[4-(5-dimethylaminopentyloxy)-3-methoxyphenyl]propionamide hydrochloride, which had the following physiochemical properties:
0.86 (3 H, d, J=6 Hz),
0.9–2.1 (15 H, m),
2.41 (2 H, t, J=7 Hz),
2.52 (2 H, t, J=7 Hz),
2.91 (2 H, t, J=7 Hz), 3.01 (6 H, s),
3.63 (1 H, m), 3.81 (3 H, s),
4.12 (2 H, t, J=7 Hz),
6.7–7.0 (3 H, m)
MS [(M-Cl)+]:405
HRMS (C$_{24}$H$_{41}$N$_2$O$_3$):
Theoretical value: 405.31172.
Measured value: 405.31243.

EXAMPLE 149

Reduction and Conversion into Non-toxic Salt

Using 1 g of N-(trans-4-methylcyclohexyl)-4-4-dimethylaminobutoxy)-3-methoxycinnamamide (Example 136), 0.05 g of 10% palladium-carbon, and 100 ml of methanol, a reaction similar to that conducted in Example 147 was carried out. The product obtained was recrystallized from methylene chloride/ether, yielding 0.81 g of N-(trans-4-methylcyclohexyl)-3-[4-(4-dimethylaminobutoxy)-3-methoxyphenyl]propionamide (a compound of the present invention) as light-greenish white crystal, which had the following physiochemical properties:

Proton nuclear magnetic resonance spectrum ($\delta$ ppm in CDCl$_3$):
0.87 (3 H, d, J=6 Hz),
0.9–2.1 (13 H, m), 2.22 (6 H, s),
2.24 (2 H, t, J=7 Hz),
2.34 (2 H, t, J=7 Hz),
2.81 (2 H, t, J=7 Hz), 3.64 (1 H, m),
3.81 (3 H, s), 3.99 (2 H, t, J=7 Hz),
5.14 (1 H, m), 6.7–6.9 (3 H, m)
MS [(M+H)+]:391
HRMS (C$_{23}$H$_{39}$N$_2$O$_3$):
Theoretical value: 391.29607.
Measured value: 391.29644.

The compound described above was reacted in the ordinary method, converting it into N-(trans-4-methylcyclohexyl)-3-[4-(4-dimethylaminobutoxy)-3-methoxyphenyl]propionamide hydrochloride, which had the following physiochemical properties:

Proton nuclear magnetic resonance spectrum ($\delta$ ppm in D$_2$O):
0.86 (3 H, d, J=6 Hz),
0.9–2.2 (13 H, m),
2.36 (2 H, t, J=7 Hz),
2.49 (2 H, t, J=7 Hz),
2.86 (2 H, t, J=7 Hz), 3.00 (6 H, s),
3.63 (1 H, m), 3.80 (3 H, s),
4.13 (2 H, t, J=7 Hz),
6.7–7.0 (3 H, m)
MS [(M-Cl)+]:391
HRMS (C$_{23}$H$_{39}$N$_2$O$_3$):
Theoretical value: 391.29607.
Measured value: 391.29652.

EXAMPLE 150

Reduction and Conversion into Non-toxic Salt

Using 1.5 g of N-(trans-4-methylcyclohexyl)-4-3-dimethylaminopropoxy)-3-methoxycinnamamide (Example 137), 0.075 g of 10% palladium-carbon, and 100 ml of methanol, a reaction similar to that conducted in Example 147 was carried out. The product obtained was recrystallized from methylene chloride/ether, yielding 1.42 g of N-(trans-4-methylcyclohexyl)-3-[4-(3-dimethylaminopropoxy)-3-methoxyphenyl]propionamide (a compound of the present invention) as white crystal, which had the following physiochemical properties:

Proton nuclear magnetic resonance spectrum ($\delta$ ppm in CDCl$_3$):
0.86 (3 H, d, J=6 Hz), 0.9–1.9 (9 H, m), 2.2–2.4 (2 H, m),
2.36 (2 H, t, J=7 Hz), 2.72 (6 H, s),
2.85 (2 H, t, J=7 Hz),
3.08 (2 H, t, J=7 Hz), 3.66 (1 H, m),
3.82 (3 H, s), 4.03 (3 H, t, J=7 Hz),
4.17 (2 H, t, J=6 Hz), 5.21 (1 H, m),
6.7–6.9 (3 H, m)
MS [(M+H)+]:377

The compound described above was reacted in the ordinary method, converting it into N-(trans-4-methylcyclohexyl)-3-[4-(3-dimethylaminopropoxy)-3-methoxyphenyl]propionamide hydrochloride, which had the following physiochemical properties:

Proton nuclear magnetic resonance spectrum (δ ppm in $D_2O$):
0.86 (3 H, d, J=6 Hz),
0.9–2.2 (9 H, m), 2.4–2.6 (2 H, m),
2.97 (2 H, t, J=7 Hz),
2.99 (6 H, s), 3.21 (2 H, t, J=7 Hz),
3.66 (1 H, m), 4.19 (2 H, t, J=7 Hz),
4.42 (2 H, t, J=7 Hz),
6.7–7.0 (3 H, m)
MS [(M-Cl)+]:377
HRMS ($C_{22}H_{37}N_2O_3$):
Theoretical value: 377.28042.
Measured value: 377.28069.

EXAMPLE 151

Reduction and Conversion into Non-toxic Salt

Using 1.5 g of N-(trans-4-methylcyclohexyl)-4-(2-diethylaminoethoxy)-3-methoxycinnamamide (Example 140), 0.075 g of 10% palladium-carbon, and 100 ml of methanol, a reaction similar to that conducted in Example 147 was carried out. As a result, 1.21 g of N-(trans-4-methylcyclohexyl)-3-[4-(2-diethylaminoethoxy) -3- methoxyphenyl]propionamide (a compound of the present invention) was obtained as a colorless oil, which had the following physiochemical properties:

Proton nuclear magnetic resonance spectrum (δ ppm in $CDCl_3$):
0.86 (3 H, d, J=6 Hz),
0.9–1.9 (9 H, m),
1.03 (3 H, t, J=7 Hz),
2.36 (2 H, t, J=7 Hz),
2.59 (2 H, q, J=7 Hz),
2.85 (2 H, t, J=7 Hz),
2.88 (2 H, t, J=7 Hz), 3.64 (1 H, m),
3.83 (3 H, s), 4.04 (2 H, t, J=7 Hz),
5.12 (1 H, m), 6.6–6.9 (3 H, m)
MS [(M+H)+]:391

The compound described above was reacted in the ordinary method, converting it into N-(trans-4-methylcyclohexyl)-3-[4-(2-diethylaminoethoxy)-3-methoxyphenyl]propionamide hydrochloride, which had the following physiochemical properties:

Proton nuclear magnetic resonance spectrum (δ ppm in $D_2O$):
0.86 (3 H, d, J=6 Hz),
0.9–2.0 (9 H, m),
1.98 (3 H, t, J=7 Hz),
2.86 (2 H, t, J=7 Hz),
2.99 (2 H, t, J=7 Hz),
3.21 (2 H, t, J=7 Hz),
3.56 (q, 2 H, J=7 Hz), 3.63 (1 H, m),
3.82 (3 H, s), 4.26 (2 H, t, J=7 Hz),
6.6–6.9 (3 H, m)
MS [(M-Cl)+]:391

HRMS ($C_{23}H_{39}N_2O_3$):
Theoretical value: 391.29607.
Measured value: 391.29625.

EXAMPLE 152

Reduction and Conversion into Non-toxic Salt

Using 1 g of N-(trans-4-methylcyclohexyl)-4-(2-piperidinoethoxy)-3-methoxycinnamamide (Example 142), 0.05 g of 10% palladium-carbon, and 100 ml of methanol, a reaction similar to that conducted in Example 147 was carried out. The product obtained was recrystallized from methylene chloride/ether, yielding 0.91 g of N-(trans-4-methylcyclohexyl)-3-[4-(2-piperidinoethoxy)-3-methoxyphenyl]propionamide (a compound of the present invention) as white crystal, which had the following physiochemical properties:

Proton nuclear magnetic resonance spectrum (δ ppm in $CDCl_3$):
0.86 (3 H, d, J=6 Hz),
0.9–1.9 (15 H, m),
2.36 (2 H, t, J=7 Hz),
2.4–2.6 (4 H, m),
2.79 (2 H, t, J=6 Hz),
2.86 (2 H, t, J=7 Hz), 3.64 (1 H, m),
3.83 (3 H, s), 4.10 (2 H, t, J=6 Hz),
5.08 (1 H, m), 6.7–6.9 (3 H, m)
MS [(M+H)+]:403

The compound described above was reacted in the ordinary method, converting it into N-(trans-4-methylcyclohexyl)-3-[4-(2-piperidinoethoxy)-3-methoxyphenyl]propionamide hydrochloride, which had the following physiochemical properties:

Proton nuclear magnetic resonance spectrum (δ ppm in $D_2O$):
0.85 (3 H, d, J=6 Hz),
0.9–2.0 (15 H, m),
2.40 (2 H, t, J=7 Hz),
2.81 (2 H, t, J=7 Hz),
3.4–3.6 (4 H, m),
3.86 (2 H, t, J=7 Hz),
3.88 (2 H, t, J=7 Hz), 3.90 (3 H, s),
4.16 (2 H, t, J=7 Hz),
6.6–6.9 (3 H, m)
MS [(M-Cl)+]:403
HRMS ($C_{24}H_{39}N_2O_3$):
Theoretical value: 403.29607.
Measured value: 403.29558.

EXAMPLE 153

Reduction and Conversion into Non-toxic Salt

Using 1 g of N-(trans-4-methylcyclohexyl)-4-[2-(1-pyrrolidinyl)ethoxy]-3-methoxycinnamamide (Example 143), 0.05 g of 10% palladium-carbon, and 100 ml of methanol, a reaction similar to that conducted in Example 147 was carried out. The product obtained was recrystallized from methylene chloride/ether, yielding 0.88 g of N-(trans-4-methylcyclohexyl)-3-{4-[2-(1-pyrrolidinyl) ethoxy]-3-methoxyphenyl}propionamide (a compound of the present invention) as white crystal, which had the following physiochemical properties:

Proton nuclear magnetic resonance spectrum (δ ppm in $CDCl_3$):
0.86 (3 H, d, J=6 Hz),
0.9–1.9 (6 H, m),
2.36 (2 H, t, J=7 Hz), 2.60 (2 H, m),
2.85 (2 H, t, J=7 Hz),
2.90 (2 H, t, J=7 Hz), 3.64 (1 H, m), 3.83 (3 H, s), 4.09 (2 H, t, J=7 Hz),
5.11 (1 H, m), 6.7–6.9 (3 H, m)
MS [(M+H)+]:389

The compound described above was reacted in the ordinary method, converting it into N-(trans-4-methylcyclohexyl)-3-{4-[2-(1-pyrrolidinyl)ethoxy]-3-methoxyphenyl}propionamide hydrochloride, which had the following physiochemical properties:

Proton nuclear magnetic resonance spectrum ($\delta$ ppm in $D_2O$):
0.86 (3 H, d, J=6 Hz),
0.9–1.9 (6 H, m),
2.39 (2 H, t, J=7 Hz),
2.97 (2 H, t, J=7 Hz), 3.40 (2 H, m),
3.64 (2 H, d, J=7 Hz), 3.81 (3 H, s),
4.17 (2 H, t, J=7 Hz),
6.7–6.9 (3 H, m)
MS [(M-Cl)+]:389
HRMS ($C_{23}H_{37}N_2O_3$):
Theoretical value: 387.28242.
Measured value: 389.28066.

EXAMPLE 154

Reduction and Conversion into Non-toxic Salts

Using 1 g of N-(trans-4-methylcyclohexyl)-4-[2-(4-methylpiperazinyl)ethoxy]-3-methoxycinnamamide (Example 145), 0.05 g of 10% palladium-carbon, and 100 ml of methanol, a reaction similar to that conducted in Example 147 was carried out. The product obtained was recrystallized from methylene chloride/ether, yielding 0.64 g of N-(trans-4-methylcyclohexyl)-3-{4-[2-(4-methylpiperazinyl)ethoxy]-3-methoxyphenyl}propionamide (a compound of the present invention) as light-brownish white crystal, which had the following physiochemical properties:

Proton nuclear magnetic resonance spectrum ($\delta$ ppm in $CDCl_3$):
0.86 (3 H, d, J=6 Hz),
0.9–1.9 (9 H, m), 2.3 (3 H, s),
2.35 (2 H, t, J=7 Hz),
2.4–2.7 (8 H, m),
2.81 (2 H, t, J=6 Hz),
2.84 (2 H, t, J=7 Hz), 3.65 (1 H, m),
3.83 (3 H, s), 4.09 (3 H, t, J=6 Hz),
5.08 (1 H, m), 6.7–6.9 (3 H, m)
MS [(M+H)+]:418

The compound described above was reacted in the ordinary method, converting it into N-(trans-4methylcyclohexyl) -3-{4-[2-(4-methylpiperazinyl)ethoxy]-3-methoxyphenyl}propionamide dihydrochloride, which had the following physiochemical properties:

Proton nuclear magnetic resonance spectrum ($\delta$ppm in $D_2O$):
0.86 (3 H, d, J=6 Hz),
0.9–1.9 (9 H, m),
2.98 (2 H, t, J=7 Hz), 3.01 (3 H, s),
3.41 (2 H, t, J=7 Hz),
3.3–3.6 (8 H, m),
3.64 (2 H, t, J=7 Hz), 3.82 (3 H, s),
4.21 (2 H, t, J=7 Hz),
6.9–7.1 (3 H, m)
MS [(M+H-2HCl)+]:418
HRMS ($C_{24}H_{40}N_3O_3$):
Theoretical value: 418.30697.
Measured value: 418.30640.

The compound described above was reacted in the ordinary method, converting it into N-(trans-4-methylcyclohexyl)-3-{4-[2-(4-methylpiperazinyl)ethoxy]-3-methoxyphenyl}propionamide dimaleic acid salt, which had the following physiochemical properties:

Proton nuclear magnetic resonance spectrum ($\delta$ ppm in $CD_3OD$): 0.87 (3H, d, J=6 Hz), 0.9–1.9 (9H, m), 2.37 (2H, t, J=7 Hz), 2.80 (3H, s), 2.80 (2H, t, J=7 Hz), 2.9–3.1 (6H, m), 3.2–3.4 (4H, m), 3.5–3.7 (1H, m), 3.82 (3H, s), 4.11 (2H, t, J=7 Hz), 6.29 (4H, s), 6.9–7.1 (3H, m).

The compound described above was reacted in the ordinary method, converting it into N-(trans-4-methylcyclohexyl)-3-{4-[2-(4-methylpiperazinyl)ethoxy]-3-methoxyphenyl}propionamide difumaric acid salt, which had the following physiochemical properties:

Proton nuclear magnetic resonance spectrum ($\delta$ ppm in $CD_3OD$): 0.87 (3H, d, J=6 Hz), 0.9–1.9 (9H, m), 2.41 (2H, t, J=7 Hz), 2.78 (3H, s), 2.79 (2H, t, J=7 Hz), 2.9–3.1 (6H, m), 3.2–3.4 (4H, m), 3.4–3.6 (1H, m), 3.81 (3H, s), 4.10 (2H, t, J=7 Hz), 6.72 (4H, s), 6.7–6.9 (3H, m).

The compound described above was reacted in the ordinary method, converting it into N-(trans-4-methylcyclohexyl)-3-{4-[2-(4-methylpiperazinyl)ethoxy]-3-methoxyphenyl}propionamide disuccinic acid salt, which had the following physiochemical properties:

Proton nuclear magnetic resonance spectrum ($\delta$ ppm in $CD_3OD$): 0.87 (3H, d, J=6 Hz), 0.9–1.9 (9H, m), 2.37 (2H, t, J=7 Hz), 2.52 (8H, s), 2.66 (3H, s), 2.80 (2H, t, J=7 Hz), 2.9–3.0 (6H, m), 3.0–3.2 (4H, m), 3.4–3.6 (1H, m), 3.81 (3H, s), 4.09 (2H, t, J=7 Hz), 6.71 (1H, dd, J=2, 8 Hz), 6.82 (1H, d, J=2 Hz), 6.85 (1H, d, J=8 Hz).

EXAMPLE 155

Reduction and Conversion into Non-Toxic Salt

Using 1 g of N-(trans-4-methylcyclohexyl)-4-(2-morpholinoethoxy)-3-methoxycinnamamide (Example 144), 0.05 g of 10% palladium-carbon, and 100 ml of methanol, a reaction similar to that conducted in Example 147 was carried out. The product obtained was recrystallized from methylene chloride/ether, yielding 0.90 g of N-(trans-4methylcyclohexyl)-3-[4-(2-morpholinoethoxy)-3-methoxyphenyl]propionamide (a compound of the present invention) as white crystal, which had the following physiochemical properties:

Proton nuclear magnetic resonance spectrum ($\delta$ ppm in $CDCl_3$): 0.86 (3H, d, J=6 Hz), 0.9–1.9 (9H, m), 2.36 (2H, t, J=7 Hz), 2.56 (4H, m), 2.79 (2H, t, J=5 Hz), 2.85 (2H, t, J=8 Hz), 3.64 (1H, m), 3.71 (4H, m), 3.83 (3H, s), 4.09 (2H, t, J=6 Hz), 5.09 (1H, m), 6.7–6.9 (3H, m).
MS [(M+H)+]: 405

The compound described above was reacted in the ordinary method, converting it into N-(trans-4-methylcyclohexyl)-3-[4-(2-morpholinoethoxy)-3-methoxyphenyl]propionamide hydrochloride, which had the following physiochemical properties:

Proton nuclear magnetic resonance spectrum ($\delta$ ppm in $D_2O$): 0.86 (3H, d, J=6 Hz), 0.9–1.9 (9H, m), 2.81 (2H, t, J=7 Hz), 2.98 (2H, t, J=7 Hz), 3.59 (4H, m), 3.62 (2H, t, J=7 Hz), 3.72 (4H, m), 3.82 (3H, s), 4.16 (2H, t, J=7 Hz), 6.7–6.9 (3H, m).
MS [(M-Cl)+]: 405
HRMS ($C_{23}H_{37}N_2O_4$): Theoretical value: 405.27533. Measured value: 405.27512.

EXAMPLE 156

Reduction and Conversion into Non-toxic Salts

Using 1 g of N-(trans-4-methylcyclohexyl)-4-[2-(1-imidazolyl)ethoxy]-3-methoxycinnamamide (Example 146), 0.05 g of 10% palladium-carbon, and 100 ml of methanol, a reaction similar to that conducted in Example 147 was carried out. The product obtained was recrystallized from methylene chloride/ether, yielding 0.93 g of N-(trans-4-methylcyclohexyl)-3-{4-[2-(1-imidazolyl)ethoxy]-3-methoxyphenyl}propionamide (a compound of the present invention) as light-brownish white crystal, which had the following physiochemical properties:

Proton nuclear magnetic resonance spectrum ($\delta$ ppm in CDCl$_3$): 0.86 (3H, d, J=6 Hz), 0.9–2.0 (9H, m), 2.35 (2H, t, J=7 Hz), 2.85 (2H, t, J=7 Hz), 3.65 (1H, m), 3.82 (3H, s), 4.19 (2H, t, J=5 Hz), 4.30 (2H, t, J=5 Hz), 5.48 (1H, m), 6.7–6.8 (4H, m), 7.05 (1H, dd, J=6, 2 Hz), 7.62 (1H, s).

MS [(M+H)+]: 386

The compound described above was reacted in the ordinary method, converting it into N-(trans-4-methylcyclohexyl)-3-{4-[2-(1-imidazolyl)ethoxy]-3-methoxyphenyl}propionamide hydrochloride, which had the following physiochemical properties:

Proton nuclear magnetic resonance spectrum ($\delta$ ppm in D$_2$O): 0.86 (3H, d, J=6 Hz), 0.9–2.0 (1H, m), 2.86 (2H, t, J=7 Hz), 3.08 (2H, t, J=7 Hz), 3.68 (1H, m), 3.80 (3H, s), 4.31 (2H, t, J=7Hz), 4.71 (2H, t, J=7 Hz), 6.7–7.0 (3H, m) 7.52 (1H, d, J=8 Hz), 7.71 (1H, s), 9.06 (1H, s).

MS [(M+H-2 HCl)+]: 386

HRMS (C$_{22}$H$_{32}$N$_2$O$_3$): Theoretical value: 386.24437. Measured value: 386.24448.

The compound described above was reacted in the ordinary method, converting it into N-(trans-4-methylcyclohexyl)-3-{4-[2-(1-imidazolyl)ethoxy]-3-methoxyphenyl}propionamide maleic acid salt, which had the following physiochemical properties:

Proton nuclear magnetic resonance spectrum ($\delta$ ppm in CD$_3$OD): 0.87 (3H, d, J=6 Hz), 0.9–1.8 (9H, m), 2.36 (2H, t, J=7 Hz), 2.79 (2H, t, J=7 Hz), 3.4–3.6 (1H, m), 3.79 (3H, s), 4.27 (2H, t, J=7 Hz), 4.59 (2H, t, J=7 Hz), 6.25 (2H, s), 6.70 (1H, dd, J=2, 8 Hz), 6.82 (1H, d, J=2 Hz), 6.83 (1H, d, J=8 Hz), 7.53 (1H, t, J=2 Hz), 7.71 (1H, t, J=2 Hz), 8.95 (1H, s).

The compound described above was reacted in the ordinary method, converting it into N-(trans-4-methylcyclohexyl)-3-{4-[2-(1-imidazolyl)ethoxy]-3-methoxyphenyl}propionamide fumaric acid salt, which had the following physiochemical properties:

Proton nuclear magnetic resonance spectrum ($\delta$ ppm in CD$_3$OD): 0.87 (3H, d, J=6 Hz), 0.9–1.8 (9H, m), 2.35 (2H, t, J=7 Hz), 2.79 (2H, t, J=7 Hz), 3.4–3.6 (1H, m), 3.79 (3H, s), 4.21 (2H, t, J=7 Hz), 4.43 (2H, t, J=7 Hz), 6.70 (1H, dd, J=2, 8 Hz), 6.71 (2H, s) 6.79 (1H, d, J=8 Hz), 6.82 (1H, d, J=2 Hz), 7.16 (1H, t, J=2 Hz), 7.41 (1H, t, J=2 Hz), 8.20 (1H, s).

EXAMPLE 157

Reduction and Conversion into Non-toxic Salts

Using 2 g of N-(trans-4-methylcyclohexyl-4-(2-dimethylaminoethoxy)-3-methoxycinnamamide (Example 139), 0.1 g of 10% palladium-carbon, and 100 ml of methanol, a reaction similar to that conducted in Example 147 was carried out. The product obtained was recrystallized from methylene chloride/ether, yielding 1.89 g of N-(trans-4-methylcyclohexyl)-3-[4-(2-dimethylaminoethoxy)-3-methoxyphenyl]propionamide (a compound of the present invention) as white crystal, which had the following physiochemical properties:

Proton nuclear magnetic resonance spectrum ($\delta$ ppm in CDCl$_3$): 0.86 (3H, d, J=6 Hz), 0.9–2.0 (9H, m), 2.34 (6H, s), 2.36 (1H, t, J=7 Hz), 2.73 (2H, t, J=7 Hz), 2.85 (2H, t, J=7 Hz), 3.62 (1H, m), 3.83 (3H, s), 4.05 (2H, t, J=7 Hz), 5.08 (1H, m), 6.6–6.9 (3H, m).

MS [(M+H)+]: 363

The compound described above was reacted in the ordinary method, converting it into N-(trans-4-methylcyclohexyl)-3-[4-(2-dimethylaminoethoxy)-3-methoxyphenyl]propionamide hydrochloride, which had the following physiochemical properties:

Proton nuclear magnetic resonance spectrum ($\delta$ ppm in D$_2$O): 0.81–3H, d, J=6 Hz), 0.8–1.7 (9H, m), 2.44 (2H, t, J=7 Hz), 2.85 (2H, t, J=7 Hz), 3.00 (6H, s), 3.58 (2H, t, J=7 Hz), 3.86 (3H, s), 4.33 (2H, t, J=7 Hz), 6.8–7.1 (3H, m).

MS [(M-Cl)+]: 363

HRMS (C$_{21}$H$_{35}$N$_2$O$_3$): Theoretical value: 363.26477. Measured value: 363.26427.

EXAMPLE 158

Amination and Conversion into Non-toxic Salt

Using 1.9 g N-(trans-4-methylcyclohexyl)-4-(2-chloroethoxy)-3-methoxycinnamamide (Example 138), 3.4 ml of diallyamine, and 50 ml of methyisobutylketone, a reaction similar to that conducted in Example 142 was carried out. As a result, 1.16 g of N-(trans-4-methylcyclohexyl)-4-(2-diallylaminoethoxy)-3-methoxycinamamide (a compound of the present invention) was obtained as white crystal, which had the following physiochemical properties:

Proton nuclear magnetic resonance spectrum ($\delta$ ppm in CDCl$_3$): 0.89 (3H, d, J=6 Hz), 1.0–2.1 (9H, m), 2.91 (2H, t, J=7 Hz), 3.17 (4 H, d, J=6 Hz), 3.71 (1H, m), 3.87 (3H, s), 4.08 (2H, t, J=7 Hz), 5.1–5.3 (4H, m), 5.36 (1H, d, 18 Hz), 5.86–6.0 (2H, m), 6.18 (1H, d, J=15 Hz), 6.83 (1H, d, J=8 Hz), 7.00 (1H, d, J=2 Hz), 7.02 (1H, dd, J=2, 8 Hz), 7.49 (1H, d, J=15 Hz).

MS [M+]: 412

HRMS (C$_{25}$H$_{36}$N$_2$O$_3$): Theoretical value: 412.27259. Measured value: 412.27255.

The compound described above was reacted in the ordinary method, converting it into N-(trans-4-methylcyclohexyl)-4-(2-diallylaminoethoxy)-3-methoxycinnamamide hydrochloride, which had the following physiochemical properties:

Proton nuclear magnetic resonance spectrum ($\delta$ ppm in CD$_3$OD): 0.90 (3H, d, J=6 Hz), 0.9–2.0 (9H, m), 3.58 (2H, t, J=4 Hz), 3.70 (1H, m), 3.91 (3H, s), 3.98 (2H, d, J=7 Hz), 4.39 (3H, t, J=5 Hz), 5.6–5.8 (4H, m), 5.9–6.2 (2H, m), 6.47 (1H, d, J=16 Hz), 7.02 (1H, d, J=8 Hz), 7.12 (1H, dd, J=2, 8 Hz), 7.20 (1H, d, J=2 Hz), 7.42 (1H, d, J=16 Hz).

MS [M−]: 448

EXAMPLE 159

Amination and Conversion into Non-toxic Salt

Using 1.9 g N-(trans-4-methylcyclohexyl)-4-(2-chloroethoxy)-3-methoxycinnamamide (Example 138), 5.6 ml of dipentylamine, and 50 ml of methylisobutylketone, a reaction similar to that conducted in Example 142 was carried out. As a result, 2.97 g of N-(trans-4- methylcyclohexyl)-4-(2-dipentylaminoethoxy)-3-methoxycinnamamide (a compound of the present invention) was obtained as white crystal, which had the following physiochemical properties:

Proton nuclear magnetic resonance spectrum (δ ppm in CDCl$_3$): 0.86 (3H, d, J=6 Hz), 0.89 (6H, d, J=6 Hz), 0.9–2.1 (21H, m), 2.47 (6H, t, J=8 Hz), 2.88 (2H, t, J=7 Hz), 3.81 (1H, m), 3.89 (3H, s), 4.06 (2H, t, J=7 Hz), 5.38 (1H, d, J=8 Hz), 6.19 (1H, d, J=15 Hz), 6.84 (1H, d, J=8 Hz), 7.00 (1H, d, J=2 Hz), 7.03 (1H, d, J=8 Hz), 7.49 (1H, d, J=16 Hz).

MS [M+]: 472

HRMS (C$_{29}$H$_{48}$N$_2$O$_3$): Theoretical value: 472.36649. Measured value: 472.36745.

The compound described above was reacted in the ordinary method, converting it into N-(trans-4-methylcyclohexyl)-4-(2-dipentylaminoethoxy)-3-methoxycinnamamide hydrochloride, which had the following physiochemical properties:

Proton nuclear magnetic resonance spectrum (δ ppm in CD$_3$OD): 0.90 (3H, d, J=6 Hz), 0.94 (6H, t, J=7 Hz), 0.9–2.0 (21H, m), 3.25 (4H, m), 3.65 (2H, t, J=5 Hz), 3.71 (1 H, m), 3.90 (3H, s), 4.37 (2H, t, J=5 Hz), 6.47 (1H, d, J=16 Hz), 7.01 (1H, d, J=8 Hz), 7.12 (1H, dd, J=2, 8 Hz), 7.20 (1H, d, J=2 Hz), 7.42 (1H, d, J=16 Hz).

MS [M−]: 508.

EXAMPLE 160

Reduction

Using 0.2 g of N-(trans-4-methylcyclohexyl)-4-(2-dipentylaminoethoxy)-3-methoxycinnamamide (Example 159), 0.01 g of 10% palladium-carbon, and 35 ml of methanol, a reaction similar to that conducted in Example 147 was carried out. As a result, 0.12 g of N-(trans-4-methylcyclohexyl)-3-[4-(2-dipentylaminoethoxy)-3-methoxyphenyl]propionamide (a compound of the present invention) was obtained was white crystal, which had the following physiochemical properties:

Proton nuclear magnetic resonance spectrum (δ ppm in CDCl$_3$): 0.86 (3H, d, J=7 Hz), 0.86 (6H, d, J=7 Hz), 0.9–2.0 (21H, m), 2.36 (2H, t, J=7 Hz), 2.43 (4H, t, J=6 Hz), 2.86 (2H, t, J=7 Hz), 3.66 (1H, m), 3.83 (3H, s), 4.01 (2H, t, J=7 Hz), 5.11 (1H, d, J=8 Hz), 6.68 (1H, dd, J=2, 8 Hz), 6.72 (1H, s), 6.79 (1H, dd, J=2, 8 Hz).

MS [(M-H)+]: 473

EXAMPLE 161

Amination

Using 1.9 g of N-(trans-4-methylcyclohexyl)-4-(2-chloroethoxy)-3-methoxycinnamamide (Example 138), 8.3 ml of dioctylamine, and 50 ml of methyl isobutylketone, a reaction similar to that conducted in Example 142 was carried out. As a result, 0.9 g of N-(trans-4-methylcyclohexyl)-4-(2-dioctylaminoethoxy )-3-methoxycinnamamide (a compound of the present invention) was obtained as white crystal, which had the following physiochemical properties:

Proton nuclear magnetic resonance spectrum (δ ppm in CDCl$_3$): 0.86 (3H, d, J=6 Hz), 0.88 (6H, d, J=7 Hz), 0.9–2.1 (33H, m), 2.43 (4H, t , J=7 Hz), 2.91 (2H, t, J=5 Hz), 3.82 (1H, m), 3.91 (3H, s), 4.03 (2H, t, J=5 Hz), 5.39 (1H, d , J=8 Hz), 6.19 (1H, d, J=15 Hz), 6.85 (1H, d, J=8 Hz), 7.01 (1H, dd, J=2, 8 Hz), 7.05 (1H, s), 7.49 (1H, d, J=16 Hz).

EXAMPLE 162

Amination and Conversion into Non-toxic Salt

Using 1.9 g N-(trans-4-methylcyclohexyl)-4-chloroethoxy)-3-methoxycinnamamide (Example 138), 4.56 g of 4-piperidinopiperidine, and 50 ml of methylisobutylketone, a reaction similar to that conducted in Example 142 was carried out. As a result, 1.51 g of N-(trans-4-methylcyclohexyl)-4-[2-(4-piperidinopiperidino)ethoxy]-3-methoxycinnamamide (a compound of the present invention) was obtained as white crystal, which had the following physiochemical properties:

Proton nuclear magnetic resonance spectrum (δ ppm in CDCl$_3$): 0.89 (3H, d, J=6 Hz), 0.9–2.6 (26H, m), 2.79 (2H, t, J=7 Hz), 3.0–3.1 (2H, m), 3.79 (1H, m), 3.88 (3H, s), 4.12 (2H, t, J=7 Hz), 5.81 (1H, d, J=8 Hz), 6.19 (1H, d, J=16 Hz), 6.84 (1H, d, J=8 Hz), 7.00 (1H, d, J=2 Hz), 7.02 (1H, dd, J=2, 8 Hz), 7.49 (1H, d, J=16 Hz).

MS [M+]: 483

HRMS (C$_{29}$H$_{45}$N$_3$O$_3$): Theoretical value: 483.34609. Measured value: 483.34624.

The compound described above was reacted in the ordinary method, converting it into N-(trans-4-methylcyclohexyl)-4-[2-(4-piperidinopiperidino)ethoxy]-3-methoxycinnamamide hydrochloride, which had the following physiochemical properties:

Proton nuclear magnetic resonance spectrum (δ ppm in CD$_3$OD): 0.90 (3H, d, J=6 Hz), 0.9–2.6 (18H, m), 2.9–3.8 (8H, m), 3.62 (2H, t, J=7 Hz), 3.79 (1H, m), 3.92 (3H, s), 3.9–4.1 (1H, m), 4.42 (2H, t, J=7 Hz), 6.48 (1H, d, J=16 Hz), 7.04 (1H, d, J=8 Hz), 7.13 (1H, dd, J=2, 8 Hz), 7.20 (1H, d, J=2 Hz), 7.42 (1H, d, J=16 Hz).

MS [(M-H)−]: 555

EXAMPLE 163

Reduction

Using 0.2 g of N-(trans-4-methylcyclohexyl)-4-[2-(4-piperidinopiperidino)ethoxy]-3-methoxycinnamamide (Example 162), 0.01 g of 10% palladium-carbon, and 30 ml of methanol, a reaction similar to that conducted in Example 147 was carried out. As a result, 0.12 g of N-(trans-4-methylcyclohexyl)-3-{4-[2-(4-piperidinopiperidino)ethoxy]-3-methoxyphenyl}propionamide (a compound of the present invention) was obtained as white crystal, which had the following physiochemical properties:

Proton nuclear magnetic resonance spectrum (δ ppm in CDCl$_3$): 0.86 (3H, d, J=6 Hz), 0.9–2.4 (22H, m), 2.36 (2H, t, J=7 Hz), 2.4–2.6 (4H, m), 2.77 (2H, t, J=6 Hz), 2.85 (2H, t, J=7 Hz), 3.0–3.2 (2H, m), 3.6–3.8 (1H, m), 3.83 (3H, s), 4.08 (2H, t, J=7 Hz), 5.11 (1H, d, J=8 Hz), 6.68 (1H, d, J=8 Hz), 6.72 (1H, s), 6.79 (1H, d, J=8 Hz).

MS [(M-H)+]: 484

EXAMPLE 164

Amination and Conversion into Non-toxic Salt

Using 1.9 g N-(trans-4-methylcyclohexyl)-4-(2-chloroethoxy)-3-methoxycinnamamide (Example 138), 2.7 g 2-ethylimdazole, and 50 ml of methylisobutyketone, a reaction similar to that conducted in Example 142 was carried out. As a result, 1.78 g of N-(trans-4-methylcyclohexyl)-4-{2-[1-(2-ethyl)imidazolyl]ethoxy}-3-methoxycinnamamide (a compound of the present invention) was obtained as white crystal, which had the following physiochemical properties:

Proton nuclear magnetic resonance spectrum (δ ppm in CDCl₃): 0.88 (3H, d, J=6 Hz), 0.9–2.1 (9H, m), 1.32 (3H, t, J=8 Hz), 2.73 (2H, q, J=8 Hz), 3.7–3.8 (1H, m), 3.84 (3H, s), 4.20 (2H, t, J=5 Hz), 4.24 (2H, t, J=4 Hz), 5.59 (1H, d, J=8 Hz), 6.22 (1H, d, J=16 Hz), 6.69 (1H, d, J=9 Hz), 6.95 (1H, d, J=1 Hz), 6.95 (1H, d, J=2 Hz), 6.96 (1H, dd, J=1, 8 Hz), 6.98 (1H, d, J=2 Hz), 7.47 (1H, d, J=16 Hz).

MS [M+]: 411

HRMS (C₂₄H₃₃N₃O₃): Theoretical value: 411.25219. Measured value: 411.25200.

The compound described above was reacted in the ordinary method, converting it into N-(trans-4-methylcyclohexyl)-4-{2-[1-(2-ethyl)imidazolyl]ethoxy}-3-methoxycinnamamide hydrochloride, which had the following physiochemical properties:

Proton nuclear magnetic resonance spectrum (δ ppm in CD₃OD): 0.90 (3H, d, J=6 Hz), 0.9–2.0 (9H, m), 1.41 (3H, t, J=8 Hz), 3.17 (2H, q, J=8 Hz), 3.6–3.8 (1H, m), 3.83 (3H, s), 4.34 (2H, t, J=6 Hz), 4.59 (2H, t, J=5 Hz), 6.42 (1H, d, J=16 Hz), 6.91 (1H, d, J=8 Hz), 7.07 (1H, dd, J=2, 8 Hz), 7.12 (1H, d, J=1 Hz), 7.39 (1H, d, J=16 Hz), 7.46 (1H, d, J=2 Hz), 7.63 (1H, d, J=2 Hz).

MS [M−]: 447

EXAMPLE 165

Reduction

Using 0.2 g of N-(trans-4-methylcyclohexyl)-4-{2-[1-(2-ethyl)imidazoly]ethoxy}-3-methoxycinnamamide (Example 162), 0.01 g of 10% palladium-carbon, and 25 ml of methanol, a reaction similar to that conducted in Example 147 was performed. As a result, 0.14 g of N-(trans-4-methylcyclohexyl)-3-{4-{2-[1-(2-ethyl)imidazolyl]ethoxy}-3-methoxyphenyl}propionamide (a compound of the present invention) was obtained as white crystal, which had the following physiochemical properties:

Proton nuclear magnetic resonance spectrum (δ ppm in CDCl₃):
0.86 (3H, d, J=6 Hz), 0.9–2.0 (9H, m), 1.32 (3H, t, J=8 Hz), 2.34 (2H, t, J=7 Hz), 2.71 (2H, q, J=8 Hz), 2.84 (2H, t, J=8 Hz), 3.6–3.8 (1H, m), 3.81 (3H, s), 4.16 (2H, t, J=4 Hz), 4.23 (2H, t, J=4 Hz), 5.19 (1H, d, J=8 Hz), 6.67 (2H, d, J=1 Hz), 6.73 (1H, s), 6.95 (1H, d, J=1 Hz), 6.98 (1H, d, J=1 Hz).

MS [M+]: 413

EXAMPLE 166

Amination and Conversion into Non-toxic Salts

Using 1.9 g N-(trans-4-methylcyctohexyl)-4-(2-chloroethoxy)-3-methoxycinnamamide (Example 138), 3.3 g of benzimidazole, and 100 ml of methylisobutylketone, a reaction similar to that conducted in Example 142 was carried out. As a result, 1.14 g of N-(trans-4-methylcyclohexyl)-4-[2-[1-benzimidazolyl)ethoxy]-3-methoxycinnamamide (a compound of the present invention) was obtained as white crystal, which had the following physiochemical properties:

Proton nuclear magnetic resonance spectrum (δ ppm in CD₃OD): 0.89 (3 H, d, J=6 Hz), 0.9–2.0 (9 H, m), 3.6–3.8 (1 H, m), 3.75 (3H, s), 4.33 (2H, t, J=5 Hz), 4.64 (2H, t, J=5 Hz), 6.38 (1H, d, J=16 Hz), 6.82 (1 H, d, J=8 Hz), 6.98 (1H, dd, J=2, 8 Hz), 7.07 (1H, d, J=2 Hz), 7.2–7.8 (4H, m), 8.27 (1H, s).

MS [M+]: 433

HRMS (C₂₆H₃₁N₃O₃): Theoretical value: 433.23654. Measured value: 433.23594.

The compound described above was reacted in the ordinary method, converting it into N-(trans-4-methylcyclohexyl)-4-[2-(1-benzimidazolyl)ethoxy]-3-methoxycinnamamide hydrochloride, which had the following physiochemical properties:

Proton nuclear magnetic resonance spectrum (δ ppm in CD₃OD ): 0.90 (3H, d, J=6 Hz), 0.9–2.0 (9H, m), 3.6–3.8 (1H, m), 3.73 (3H, s), 4.46 (2H, t, J=4 Hz), 4.96 (2H, t, J=5 Hz), 6.40 (1H, d, J=16 Hz), 6.93 (1H, d, J=8 Hz), 7.05 (1H, dd, J=2, 8 Hz), 7.09 (1H, s), 7.36 (1H, d, J=16 Hz), 7.6–8.2 (4H, m), 9.55 (1H, s).

MS [M−]: 469

EXAMPLE 167

Reduction

Using 0.2 g of N-(trans-4-methylcyclohexyl-4-[2-[1-benzimidazolyl)ethoxy]-3-methoxycinnamamide Example 166), 0.01 g of 10% palladium-carbon, and 35 ml of methanol, a reaction similar to that conducted in Example 147 was carried out. As a result, 0.11 g of N-(trans-4-methylcyclohexyl)-3-{4-[2-(1-imidazolyl)ethoxy}-3-methoxyphenyl}propionamide (a compound of the present invention) was obtained as white crystal, which had the following physiochemical properties:

Proton nuclear magnetic resonance spectrum (δ ppm in CDCl₃):
0.85 (3H, d, J=6 Hz),
0.9–2.0 (9H, m),
2.32 (2H, t, J=7 Hz),
2.82 (2H, t, J=8 Hz),
3.6–3.8 (1H, m), 3.76 (3H, s),
4.28 (2H, t, J=5 Hz),
4.54 (2H, t, J=5 Hz),
5.2–5.3 (1H, d, J=8 Hz),
6.64 (1H, d, J=2 Hz),
6.65 (1H, s), 6.70 (1H, d, J=2 Hz ),
7.2–7.6 (3H, m), 7.8–7.9 (1H, m),
8.20 (1H, s)
MS [M+]: 435

EXAMPLE 168

Amination 1.9 g of N-(trans-4-methylcyclohexyl)-4-(2-chloroethoxy)-3-methoxycinnamamide (Example 138), 4.2 ml of ethyl 4-pieperidinecarboxylate, and 50 ml of methylisobutylketone, a reaction similar to that conducted in Example 142 was carried out. As a result, 1.47 g of N-(trans-4-methylcyclohexyl)-4-{2-[4-(ethoxycarbonyl)piperidino]ethoxy}-3-methoxycinnamamide (a compound of the present invention) was obtained as white crystal, which had the following physiochemical properties:

Proton nuclear magnetic resonance spectrum (6 ppm in CDCl₃):
0.88 ( 3H, d, J=6 Hz ),
0.9–2.4 (16H, m),
1.21 (3H, t, J=7 Hz ),
2.80 (2H, t, J=6 Hz),
2.8–3.0 (2H, m), 3.7–3.9 (1H, m),
3.86 (3H, s), 4.08 (2H, t, J=7 Hz),
4.13 (2H, t, J=6 Hz),
5.44 (1H, d, J=8 Hz),
6.21 (1H, d, J=15 Hz),
6.83 (1H, d, J=8 Hz),
7.01 (1H, d, J=2 Hz),
7.01 (1H, dd, J=2, 8 Hz),
7.49 (1H, d, J=15 Hz)

MS [M+]: 472
HRMS ($C_{27}H_{40}N_2O_5$):
Theoretical value: 472.29372
Measured value: 472.29248

EXAMPLE 169

Hydrolysis and Conversion into Non-toxic Salt 10 ml of 2 M aqueous potassium hydroxide solution was added to a solution of 0.5 g of N-(trans-4-methylcyclohexyl) -4-{2-[4-(ethoxycarbonyl)piperidino]ethoxy}-3-methoxycinnamamide (Example 168) in 50 ml of methanol. The solution was reacted for 1 hours, while it was refluxed. After reaction, 2 N hydrochloric acid to the reaction solution, acidifying the solution. The solution was then extracted twice with 50 ml of methylene chloride. The organic layer obtained was dried over magnesium sulfate. Thereafter, the solvent was removed in vacuo. The product obtained was recrystallized from methanol/ether, yielding 0.43 g of N-(trans-4-methylcyclohexyl)-4-[2(4-carboxypiperidino)ethoxy]-3-methoxycinnamamide (a compound of the present invention) as white crystal, which had the following physiochemical properties:

Proton nuclear magnetic resonance
spectrum ($\delta$ ppm in $CD_3OD$):
0.91 (3H, d, J=6 Hz),
0.9–2.4 (14H, m),
2.6–2.8 (2H, m), 3.1–3.3 (1H, m),
3.60 (2H, t, J=5 Hz),
3.7–3.9 (1H, m),
3.92 (3H, s), 4.41 (2H, t, J=4 Hz),
6.47 (1H, d, J=16 Hz),
7.03 (1H, d, J=8 Hz),
7.14 (1H, d, J=8 Hz), 7.21 (1H, s),
7.42 (1H, d, J=16 Hz)

The compound described above was reacted in the ordinary method, converting it into N-(trans-4-methylcyclohexyl) -4-[2-(4-carboxypiperidino)ethoxy]-3-methoxycinnamamide sodium salt, which had the following physiochemical properties:

Proton nuclear magnetic resonance
spectrum ($\delta$ ppm in $CD_3OD$):
0.90 (3H, d, J=6 Hz),
0.9–2.2 (13H, m),
2.3–2.5 (1H, m), 3.1–3.3 (1H, m),
3.47 (2H, t, J=6 Hz),
3.5–3.8 (2H, m),
3.91 (3H, s), 4.34 (2H, t, J=5 Hz),
6.47 (1H, d, J=16 Hz),
7.01 (1H, d, J=8 Hz),
7.11 (1H, dd, J=2, 8 Hz),
7.19 (1H, d=2 Hz),
7.42 (1H, d, J=16 Hz),

EXAMPLE 170

Reduction

Using 0.2 g of N-( trans-4-methylcyclohexyl ) -4-[2-(4-carboxypiperidino) ethoxy]-3-methoxycinnamamide (Example 169), 0.01 g of 10% palladium-carbon, and 25 ml of methanol, a reaction similar to that conducted in Example 147 was carried out. As a result, 0.04 g of N-( trans-4-methylcyclohexyl )-3-{4-[2-( 4carboxypiperidino}-3-methoxyphenyl}propionamide (a compound of the present invention) was obtained as amorphous powder, which had the following physiochemical properties:

Proton nuclear magnetic resonance
spectrum ($\delta$ ppm in $CD_3OD$):
0.87 (3H, d, J=6 Hz),
0.9–2.4 (14H, m),
2.38 (1H, J=7 Hz), 2.5–2.7 (1H, m),
2.82 (2H, t, J=8 Hz),
3.1–3.3 (1H, m),
3.42 (2H, t, J=5 Hz),
3.7–3.9 (1H, m),
3.87 (3H, s), 4.26 (2H, t, J=5 Hz),
6.75 (1H, d, J=8 Hz),
6.96 (1H, d, J=2 Hz),
6.93 (1H, d, J=8 Hz)
MS [M+]: 448

EXAMPLE 171

Alkylation 20.7 g of potassium carbonate and 5 ml of methanol were added to a solution of 28.9 g of N-(trans-4-methylcyclohexyl)-4-hydroxy-3-methoxycinnamamide (Example 131) in 600 ml of methylisobutylketone. The solution was reacted for 30 minutes, while it was refluxed. Next, 27.7 ml of ethyl bromoacetate was added dropwise into the solution over about 20 minutes by means of a dropping funnel. Thereafter, the solution was stirred for 4 hours. After reaction, the solution was allowed to cool to room temperature. After the potassium carbonate has been filtered out from the filtrate, the solvent was removed in vacuo from the filtrate. The product obtained was recrystallized from methylene chloride/ether, yielding 35.2 g of N-(trans-4-methylcyclohexyl)-4-(ethoxycarbonylmethoxy)-3-methoxycinnamamide (a compound of the present invention) as white crystal, which had the following physiochemical properties:

Proton nuclear magnetic resonance
spectrum ($\delta$ ppm in $CDCl_3$):
0.88 (3H, d, J=6 Hz),
0.9–2.1 (9H, m),
1.25 (3H, t, J=7 Hz),
3.7–3.9 (1H, m),
3.89 (3H, s), 4.20 (2H, q, J=7 Hz),
4.66 (2H, s), 6.52 (1H, d, J=8 Hz),
6.22 (1H, d, J=15 Hz),
6.74 (1H, d, J=8 Hz),
7.00 (1H, dd, J=2, 6 Hz),
7.03 (1H, s), 7.48 (1H, d, J=16 Hz)
MS [(M+H)) +]: 375
HRMS ($C_{21}H_{29}NO_5$):
Theoretical value: 375.20457.
Measured value: 375.20417.

EXAMPLE 172

Hydrolysis and Conversion into Non-toxic Salts.

Using 28 g of N-( trans-4-methylcyclohexyl )-4-(ethoxycarbonylmethoxy) -3-methoxycinnamamide (Example 171), 100 ml of 254 aqueous potassium hydroxide solution, and 600 ml of methanol, a reaction similar to that conducted in Example 169 was carried out. As a result, 23.9 g of N-( trans-4-methylcyclohexyl )-4-carboxymethoxy)-3-methoxycinnamamide (a compound of the present invention) was obtained as white crystal, which had the following physiochemical properties:

Proton nuclear magnetic resonance
spectrum ($\delta$ ppm in $CD_3OD$):
0.90 (3H, d, J=6 Hz ),
0.9–2.0 (9H, m), 3.6–3.8 (1H, m), 3.88 (3H, s),
4.70 (2H,
6.42 (1H, d, J=16 Hz),
6.87 (1H, d, J=8 Hz),
7.06 (1H, dd, J=2, 8 Hz),
7.16 (1H, d, J=2 Hz),
7.40 (1H, d, J=16 Hz)
MS [M+]: 347
HRMS ($C_{19}H_{25}NO_5$):
Theoretical value: 347.17327.
Measured value: 347.17295.

The compound described above was reacted in the ordinary method, converting it into N-(trans-4-methylcyclohexyl) -4-(carboxymethoxy)-3-methoxycinnamamide sodium salt, which had the following hysiochemical properties:

Proton nuclear magnetic resonance
spectrum (δ ppm in CD₃OD):
0.90 (3H, d, J=6 Hz),
0.9–2.0 (9H, m),
3.6–3.8 (1H, m), 3.90 (3H, s),
4.42 (2H, s),
6.42 (1H, d, J=16 Hz),
6.89 (1H, d, J=8 Hz),
7.09 (1H, dd, J=2, 8 Hz),
7.16 (1H, s), 7.40 (1H, d, J=16 Hz)
MS [(M-H)+]: 368
HRMS ($C_{19}H_{23}NO_5Na$):
Theoretical value: 368.14742.
Measured value: 368.14690.

The compound described above was reacted in the ordinary method, converting it into N-(trans-4-methylcyclohexyl) -4-(carboxymethoxy)-3-methoxycinnamamide diethanolmethylamine salt, which had the following physiochemical properties:

Proton nuclear magnetic resonance
spectrum (δ ppm in CD₃OD):
0.86 (3H, d, J=6 Hz),
0.9–1.9 (9H, m),
2.27 (3H, s), 2.49 (4H, t, J=6 Hz ),
3.45 (4H, t, J=6 Hz), 3.79 (3H, s),
4.42 (2H, s),
6.42 (1H, d, J=16 Hz),
6.74 (1H, d, J=8 Hz),
7.02 (1H, d, J=8 Hz),
7.11 (1H, s),
7.26 (1H, d, J=16 Hz),
7.84 (1H, d, J=8 Hz)

The compound described above was reacted in the ordinary method, converting it into N-(trans-4-methylcyclohexyl)-4-(carboxymethoxy)-3-methoxycinnamamide trishydroxymethylaminomethane salt, which had the following physiochemical properties:

Proton nuclear magnetic resonance
spectrum (δ ppm in DMSO-d₆):
0.86 (3H, d, J=6 Hz),
0.9–1.9 (9H, m),
3.5–3.7 (1H, m), 3.79 (3H, s),
4.24 (2H, s),
6.41 (1H, d, J=16 Hz),
6.69 (1H, d, J=8 Hz),
6.99 (1H, d, J=8 Hz),
7.09 (1H, s),
7.26 (1H, d, J=16 Hz),
7.82 (1H, d, J=8 Hz)

The compound described above was reacted in the ordinary method, converting it into ammonium {4-{2-[N-trans-4-methylcyclohexyl)carbamoyl]vinyl}-2-methoxy}-phenoxyacetate salt, which had the following physiochemical properties:

Proton nuclear magnetic resonance
spectrum (δ ppm in DMSO—d₆):
0.86 (3H, d, J=6 Hz),
0.9–0.9 (9H, m),
3.4–3.6 (1H, m), 3.79 (3H, s),
4.22 (2H, s),
6.42 (1H, d, J=16 Hz),
6.70 (1H, d, J=8 Hz),
6.98 (1H, d, J=8 Hz),
7.09 (1H, d, J=1 Hz),
7.26 (1H, d, J=16 Hz),
7.86 (1H, d, J=8 Hz)

EXAMPLE 173

Reduction and Conversion into Non-toxic Salt

Using 0.5 of N-(trans-4-methylcyclohexyl)-4-(carboxymethoxy)-3-methoxycinnamamide (Example 172), 0.025 g of 10% palladium-carbon, and 70 ml of methanol, a reaction similar to that conducted in Example 147 was carried out. As a result, 0.34 g of N-(trans-4-methylcyclohexyl) -3-[4-(carboxymethoxy)-3-methoxyphenyl]propionamide (a compound of the present invention) was obtained as white crystal, which had the following physiochemical properties:

Proton nuclear magnetic resonance spectrum (δ ppm in CDCl₃):
0.86 (3H, d, J=6 Hz),
0.9–2.0 (9H, m),
2.37 (2H, t, J=7 Hz),
2.85 (2H, t, J=8 Hz),
3.6–3.8 (1H, m), 3.86 (3H, s),
4.22 (2H, S), 5.19 (1H, d, J=8 Hz),
6.68 (1H, d, J=8 Hz), 6.77 (1H, s),
6.81 (1H, d, J=8 Hz)
MS [M+]: 349

The compound described above was reacted in the ordinary method, converting it into N-(trans-4-methylcyclohexyl) -3-[4-(carboxymethoxy)-3-methoxyphenyl]propionamide sodium salt, which had the following physiochemical properties:

Proton nuclear magnetic resonance
spectrum (8 ppm in CD₃OD):
0.87 (3H, d, J=6 Hz),
0.9–1.9 (9H, m),
2.36 (2H, t, J=7 Hz),
2.80 (2H, t, J=8 Hz),
3.6–3.8 (1H, m), 3.84 (3H, s),
4.46 (2H, s),
6.69 (1H, dd, J=2, 8 Hz),
6.81 (1H, s), 6.83 (1H, d, J=8 Hz)

EXAMPLE 174

Alkylation

Using 2 g of N-(trans-4-methylcyclohexyl )-4-hydroxy-3-methoxycinnamamide (Example 131 ), 1.4 g of potassium carbonate, 4 ml of ethyl 4-bromobutylate, and 50 ml of methylisobutylketone, a reaction similar to that conducted in Example 147 was carried out. As a result, 2.7 g of N-(trans-4-methylcyclohexyl )-4-[3-(ethoxycarbonyl) propoxy]-3-methoxycinnamamide (a compound of the present invention) was obtained as white crystal, which had the following physiochemical properties:

Proton nuclear magnetic resonance
spectrum (δ ppm in CDCl3):

0.88 (3H, d, J=6 Hz),
0.9–2.1 (9H, m),
1.22 (3H, t, J=7 Hz),
2.09 (2H, q, J=7 Hz),
2.49 (2H, t, J=7 Hz),
3.7–3.9 (1H, m),
3.86 (3H, s), 4.05 (2H, d, J=6HZ),
4.08 (2H, J=7 Hz ),
5.48 (1H, J=8 Hz ),
6.21 (1H, J=16 Hz ),
6.82 (1H, d, J=8 Hz ),
7.01 (1H, s),
7.02 (1H, dd, J=2, 8 Hz ),
7.49 (1H, d, J=16H)
MS [M+]: 403
HRMS ($C_{23}H_{33}NO_5$):
Theoretical value: 403.23587.
Measured value: 403.23607.

EXAMPLE 175

Hydrolysis and Conversion into Non-toxic Salt

Using 1.6 g of N-(trans-4-methylcyclohexyl)-4-[3(ethoxycarbonyl)propoxy]-3-methoxycinnamamide (Example 174), 20 ml of 2 M aqueous potassium hydroxide solution, and 80 ml of methanol, a reaction similar to that conducted in Example 169 was carried out. As a result, 1.36 g of N-(trans-4-methylcyclohexyl)-4-(3-carboxypropoxy) -3-methoxycinnamamide (a compound of the present invention) was obtained as white crystal, which had the following physiochemical properties:
Proton nuclear magnetic resonance
spectrum (δ ppm in $CDCl_3$):
0.90 (3H, d, J=6 Hz),
0.9–2.0 (9H, m),
2.04 (2H, q, J=7 Hz),
2.48 (2H, t, J=7 Hz),
3.6–3.8 (1H, m), 3.86 (3H, s),
4.03 (2H, t, J=6 Hz),
6.40 (1H, d, J=16 Hz),
6.92 (1H, d, J=8 Hz),
7.07 (1H, d, J=8 Hz),
7.13 (1H, s), 7.40 (1H, d, J=16 Hz)
MS [(M+H))+]: 376
HRMS ($C_{21}H_{30}NO_5$):
Theoretical value: 376.21240.
Measured value: 376.21494.

The compound described above was reacted in the ordinary method, converting it into N-(trans-4-methylcyclohexyl) -4-(3-carboxypropoxy )- 3-methoxycinnamamide sodium salt, which had the following physiochemical properties:
Proton nuclear magnetic resonance
spectrum (δ ppm in $CD_3OD$):
0.91 (3H, d, J=6 Hz),
0.9–2.0 (9H, m),
2.04 (2H, q, J=7H),
2.48 (2H, t, J=7 Hz),
3.6–3.8 (1H, m), 3.86 (3H, s),
4.03 (2H, t, J=6 Hz),
6.41 (1H, d, J=16 Hz),
6.93 (1H, d, J=8 Hz),
7.05 (1H, dd, J=2, 8 Hz),
7.13 (1H, s), 7.40 (1H, d, J=16 Hz)

EXAMPLE 176

Reduction

Using 0.2 g of N-(trans-4-methylcyclohexyl)-4-(3-carboxypropoxy) -3-methoxycinnamamide (Example 175), 0.01 g of 10% palladium-carbon, and 35 ml of methanol, a reaction similar to that conducted in Example 147 was carried out. As a result, 0.13 g of N-(trans-4-methylcyclohexyl) -3-[4-(3-carboxypropoxy)-3-methoxyphenyl]-propionamide (a compound of the present invention) was obtained as white crystal, which had the following physiochemical properties:
Proton nuclear magnetic resonance
spectrum (δ ppm in $CDCl_3$):
0.86 (3H, d, J=6 Hz),
0.9–1.9 (9H, m),
2.07 (2H, q, J=7 Hz),
2.36 (2H, t, J=7 Hz),
2.57 (2H, t, J=7 Hz),
2.85 (2H, t, J=7 Hz),
3.6–3.8 (1H, m), 3.83 (3H, s),
4.02 (2H, t, J=6 Hz),
5.12 (1H, d, J=8 Hz),
6.67 (1H, dd, J=3, 8 Hz),
7.72 (1H, s),
7.13 (1H, s), 7.40 (1H, d, J=16 Hz)
MS [M+]: 377

EXAMPLE 177

Alkylation

Using 2 g of N-(trans-4-methylcyclohexyl)-4-hydroxy-3-methoxycinnamamide (Example 131), 1.4 g of potassium carbonate, 4 ml of ethyl 6-bromohexanoate, and 50 ml of methylisobutylketone, a reaction similar to that conducted in Example 171 was carried out. As a result, 2.89 g of N-(trans-4-methylcyclohexyl)-4-[5-(ethyoxycarbonyl)pentyloxy]-3-methoxycinnamamide (a compound of the present invention) was obtained as white crystal, which had the following physiochemical properties:
Proton nuclear magnetic resonance
spectrum (δ ppm in CDCl3):
0.88 (3H, d, J=6 Hz),
0.9–2.1 (13H, m),
1.21 (3H, t, J=7 Hz),
2.2–2.4 (2H, m),
3.7–3.9 (1H, m), 3.86 (3H, s),
4.03 (2H, t, J=6 Hz),
4.07 (2H, q, J=7 Hz),
5.48 (1H, d, J=8 Hz),
6.21 (1H, d, J=16 Hz),
6.80 (1H, d, J=8 Hz), 7.00 (1H, s),
7.02 (1H, dd, J=2, 8 Hz),
7.49 (1H, d, J=16 Hz)
MS [M+]: 431
HRMS ($C_{25}H_{37}NO_5$):
Theoretical value: 431.26717.
Measured value: 431.26735.

EXAMPLE 178

Hydrolysis and Conversion into Non-toxic Salt

Using 2.5 g of N-(trans-4-methylcyclohexyl)-4-[5-(ethyoxycarbonyl) pentyloxy]-3-methoxycinnamamide (Example 177), 20 ml of 2 M aqueous potassium hydroxide solution, and 80 ml of methanol, a reaction similar to that conducted in Example 169 was carried out. As a result, 2.18 g of N-(trans-4-methylcyclohexyl)-4-(5-carboxypentyloxy)-3-methoxycinnamamide (a compound of the present invention) was obtained as white crystal, which had the following physiochemical properties:
Proton nuclear magnetic resonance spectrum (δ ppm in CD$_3$OD):
0.90 (3H, d, J=6 Hz),
0.9–2.0 (15H, m),
2.29 (2H, t, J=7 Hz),
3.6–3.8 (1H, m),
3.86 (3H, s), 4.02 (2H, t, J=6 Hz),
4.87 (2H, s),
6.48 (1H, d, J=16 Hz),
6.90 (1H, d, J=8 Hz),
7.07 (1H, d, J=8 Hz),
7.12 (1H, s), 7.40 (1H, d, J=16 Hz)

The compound described above was reacted in the ordinary method, converting it into N-(trans-4-methylcyclohexyl) -4-(5-carboxypentyloxy)-3-methoxycinnamamide sodium salt, which had the following physiochemical properties:

Proton nuclear magnetic resonance
spectrum (δ ppm in CD$_3$OD):
0.90 (3H, d, J=6 Hz),
0.9–2.0 (15H, m),
2.22 (2H, t, J=7 Hz),
3.6–3.8 (1H, m),
3.86 (3H, s), 3.99 (2H, t, J=6 Hz),
4.87 (2H, s),
6.40 (1H, d, J=16 Hz),
6.91 (1H, d, J=8 Hz),
7.07 (1H, d, J=8 Hz),
7.12 (1H, s), 7.40 (1H, d, J=16 Hz)

EXAMPLE 179

Reduction

Using 0.2 g of N-(trans-4-methylcyclohexyl )-4-(5-carboxypentyloxy) -3-methoxycinnamamide, 0.01 g of 10% palladium-carbon, and 35 mR of methanol, a reaction similar to that conducted in Example 147 was carried out. As a result, 0.14 g of N-(trans-4methylcyclohexyl) -3-[4-(5-carboxypentyloxy )- 3methoxyphenyl]propionamide (a compound of the present invention) was obtained as white crystal, which had the following physiochemical properties:

Proton nuclear magnetic resonance
spectrum (δ ppm in CDCl$_3$):
0.85 (3H, d, J=6 Hz),
0.9–2.0 (15H, m),
2.3–2.5 (4H, m),
2.85 (2H, t, J=7 Hz),
3.6–3.8 (1H, m), 3.83 (3H, s),
3.95 (2H, t, J=6 Hz),
5.16 (1H, d, J=8 Hz),
6.6–6.8 (3H, m)
MS [M+]: 405

EXAMPLE 180

Amination and Conversion into Non-toxic Salt 0.5 g of sodium hydride was added to a solution of 0.68 g of pyrazole in 50 ml of THF. Next, 1.9 g of N-(trans-4-methylcyclohexyl)-4-(2-chloroethoxy)-3-methoxycinnamamide (Example 138) was added to the solution. The solution was reacted for 24 hours, while it was refluxed. After reaction, 2 N hydrochloric acid was added, acidifying the reaction solution. The solution was washed with 100 ml of methylene chloride. Ammonia water was added to the aqueous layer obtained, alkalizing the solution. Thereafter, the solution was extracted with 100 ml of methylene chloride. The organic layer obtained was dried over magnesium sulfate, and the solvent was removed in vacuo. The product obtained was refined by means of silica gel column chromatography using methylene chloride only. Thereafter, the solvent was removed in vacuo, yielding 0.44 g of N-(trans-4-methylcyclohexyl)-4-(2-pyrazolylethoxy)-3-methoxycinnamamide (a compound of the present invention) as white crystal, which had the following physiochemical properties:

Proton nuclear magnetic resonance
spectrum (δ ppm in CDCl$_3$):
0.88 (3H, d, J=6 Hz),
0.9–2.1 (9H, m),
3.7–3.9 (1H, m), 3.84 (3H, s),
4.35 (2H, t, J=5 Hz),
4.54 (2H, t, J=5 Hz),
5.49 (1H, d, J=8 Hz),
6.18 (1H, d, J=16 Hz),
6.24 (1H, t, J=2 Hz),
6.70 (1H, d, J=8 Hz),
6.97 (1H, s),
6.97 (1H, dd, J=2, 8 Hz),
7.46 (1H, d, J=16 Hz),
7.56 (1H, d, J=2 Hz),
7.59 (1H, dd, J=1, 2 Hz)
MS [M+]: 383
HRMS (C$_{22}$H$_{29}$N$_3$O$_3$):
Theoretical value: 383.22089.
Measured value: 383.22099.

The compound described above was reacted in the ordinary method, converting it into N-(trans-4-methylcyclohexyl) -4-(2-pyrazolylethoxy)-3-methoxycinnamamide hydrochloride, which had the following physiochemical properties:

Proton nuclear magnetic resonance
spectrum (δ ppm in CD$_3$OD):
0.90 (3H, d, J=6 Hz),
0.9–2.0 (9H, m),
3.6–3.8 (1H, m), 3.82 (3H, s),
4.33 (2H, t, J=5 Hz),
4.57 (2H, t, J=5 Hz),
5.49 (1H, d, J=8 Hz),
6.37 (1H, t, J=2 Hz),
6.41 (1H, d, J=16 Hz),
6.86 (1H, d, J=8 Hz),
7.04 (1H, dd, J=2, 8 Hz),
7.12 (1H, d, J=2 Hz),
7.39 (1H, d, J=16 Hz),
7.64 (1H, t, J=1 Hz),
7.86 (1H, d, J=3 Hz)
MS [(M-Cl)+]: 384

EXAMPLE 181

Reduction

Using 0.1 g of N-(trans-4-methylcyclohexyl )-4-(2-pyrazolylethoxy) -3-methoxycinnamamide (Example 180), 0.007 g of 10% palladium-carbon, and 30 ml of methanol, a reaction similar to that conducted in Example 147 was carried out. As a result, 0.05 g of N-(trans-4-methylcyclohexyl) -3-[4-(2-pyrazolylethoxy)-3methoxyphenyl]propionamide (a compound of the present invention) was obtained as light-yellowish brown crystal, which had the following physiochemical properties:

Proton nuclear magnetic resonance
spectrum (δ ppm in CDCl$_3$):
0.86 (3H, d, J=6 Hz),
0.9–2.0 (9H, m)
2.34 (2H, t, J=6 Hz),
2.84 (2H, t, J=7 Hz), 3.5–3.7 (1H, m) , 3.82 (3H, s),
4.30 (2H, t, J=6 Hz),
4.51 (2H, t, J=5 Hz),
5.07 (2H, d, J=8HZ),
6.24 (1H, t, J=2 Hz),
6.67 (1H, s),
6.67 (1H, dd, J=2, 8 Hz ),
6.72 (1H, d, J=2, 8 Hz),
7.51 (1H, d, J=2 Hz ),
7.61 (1H, d, J=2 Hz )

EXAMPLE 182

Amination and Conversion into Non-toxic Salt

Using 1.9 g of N-(trans-4-methylcyclohexyl)-4-(2-chloroethoxy) -3-methoxycinnamamide (Example 138), 1.44 g of 2-phenylimidazole, 0.5 g of sodium hydride, and 50 ml of THF, a reaction similar to that conducted in Example 180 was carried out. As a result, 0.44 g of N-(trans-4-methylcyclohexyl)-4-{2-[1-(2-phenyl)imidazolyl]ethoxy}-3-methoxycinnamamide (a compound of the present invention) was obtained as white crystal, which had the following physiochemical properties:

Proton nuclear magnetic resonance
spectrum ($\delta$ ppm in CDCl$_3$):
0.89 (3H, d, J=6 Hz),
0.9–2.1 (9H, m),
3.7–3.9 (1H, m), 3.85 (3H, s),
4.24 (2H, t, J=5 Hz),
4.40 (2H, t, J=5 Hz),
5.44 (1H, d, J=8 Hz),
6.19 (1H, d, J=16 Hz),
6.73 (1H, t, J=8 Hz),
7.0–7.1 (2H, m),
7.71 (1H, d, J=9 Hz),
7.4–7.6 (6H, m),
7.6–7.7 (2H, m)
MS [M+]: 459

The compound described above was reacted in the ordinary method, converting it into N-(trans-4-methylcyclohexyl) -4-{2-[1-(2-phenyl)imidazolyl]ethoxy}-3-methoxycinnamamide hydrochloride, which had the following physiochemical properties:

Proton nuclear magnetic resonance
spectrum ($\delta$ ppm in CD$_3$OD):
0.90 (3H, d, J=6 Hz),
0.9–2.0 (9H, m),
3.6–3.8 (1H, m), 3.83 (3H, s),
4.43 (2H, t, J=5 Hz),
4.62 (2H, t, J=5 Hz),
6.44 (1H, d, J=16 Hz),
6.92 (1H, t, J=8 Hz),
7.07 (1H, dd, J=2, 8 Hz),
7.14 (1H, d, J=2 Hz),
7.39 (1H, d, J=16 Hz),
7.6–7.8 (5H, m),
7.9–8.0 (4H, m)
MS [M−]: 405

EXAMPLE 183

Reduction

Using 0.2 g of N-(trans-4-methylcyclohexyl)-4-[2-1-{2-phenyl) imidazolyl]ethoxy}-3-methoxycinnamamide (Example 182), 0.01 g of 10% palladium-carbon, 30 ml of methanol, and 10 ml of methylene choride, a reaction similar to that conducted in Example 147 was carried out. As a result, 0.17 g of N-(trans-4-methylcyclohexyl) - 3-[4-{2-[1-(2-phenyl) imidazolyl]ethoxy}-3-methoxyphenyl}propionamide (a compound of the present invention) was obtained as white crystal, which had the following physiochemical properties:

Proton nuclear magnetic resonance
spectrum ($\delta$ ppm in CDCl$_3$):
0.86 (3H, d, J=6 Hz),
0.9–2.0 (9H, m),
2.35 (2H, t, J=7 Hz),
2.85 (2H, t, J=8 Hz),
3.6–3.8 (1H, m), 3.81 (3H, s),
4.20 (2H, t, J=5 Hz),
4.38 (2H, t, J=5 Hz),
5.21 (1H, d, J=8 Hz ),
6.66 (1H, d, J=1 Hz),
6.74 (1H, s), 7.16 (1H, s),
7.3–7.5 (5H, m), 7.4–7.5 (2H, m)
MS [M+]: 461

EXAMPLE 184

Amination and Conversion into Non-toxic Salt

Using 1.9 g of N-(trans-4-methylcyclohexyl)-4-(2-chloroethoxy)-3-methoxycinnamamide (Example 138), 0.89 g of thiazolidine, 0.5 g of sodium hydride, and 30 ml THF, a reaction similar to that conducted in Example 180 was carried out. As a result, 0.45 g of N-(trans-4-methylcyclohexyl) -4-{2-[(2-mercaptoethyl)amino]ethoxy}-3-methoxycinnamamide (a compound of the present invention) was obtained as white crystal, which had the following physiochemical properties:

Proton nuclear magnetic resonance
spectrum (8 ppm in CDCl$_3$):
0.89 (3H, d, J=6 Hz),
0.9–2.1 (9H, m),
2.70 (2H, t, J=6 Hz),
2.89 (2H, t, J=6 Hz),
2.91 (2H, t, J=7 Hz),
3.7–3.9 (1H, m),
3.88 (3H, s), 4.17 (2H, t, J=7 Hz),
5.48 (1H, d, J=8 Hz),
6.20 (1H, d, J=16 Hz),
6.82 (1H, t, J=8 Hz),
7.01 (1H, d, J=2 Hz),
7.02 (1H, dd, J=2, 8 Hz),
7.49 (1H, d, J=16 Hz)
MS [(M+H))+]: 393

The compound described above was reacted in the ordinary method, converting it into N-(trans-4-methylcyclohexyl)-4-{2-[(2mercaptoethyl)amino]ethoxy}-3-methoxycinnamamide hydrochloride, which had the following physiochemical properties:

Proton nuclear magnetic resonance
spectrum ($\delta$ ppm in CD$_3$OD):
0.91 (3H, d, J=6 Hz),
0.9–2.0 (9H, m),
2.95 (2H, t, J=6 Hz),
2.98 (2H, t, J=6 Hz),
3.23 (2H, t, J=7 Hz),
3.6–3.8 (1H, m),
3.89 (3H, s), 4.22 (2H, t, J=7 Hz),
6.43 (1H, d, J=16 Hz),
6.95 (1H, t, J=8 Hz),
7.09 (1H, dd, J=2, 8 Hz),
7.17 (1H, d, J=2 Hz),
7.41 (1H, d, J=16 Hz)
MS [(M+H)−]: 429

EXAMPLE 185

Amination

Using 1.9 g of N-(trans-4-methylcyclohexyl)-4-(2-chloroethoxy)-3-methoxycinnamamide (Example 138), 1.1 g of 2-ethyl-4-methylimidazole, 0.5 g of sodium hydride, and 50 ml of THF, a reaction similar to that conducted in Example 180 was carried out. As a result, 0.31 g of white crystal which was about 2:1 mixture of N-(trans-4-methylcyclohexyl)-4-{2-[1-(2-ethyl-4methyl)imidazolyl]ethoxy}-3-methoxycinnamamide (a compound of the present invention) and N-(trans-4-methylcyclohexyl) -4-{2-[1-(2-ethyl-5methyl-)imidazolyl]ethoxy}-3-methoxycinnamamide (a compound of the present invention) was obtained, which had the following physiochemical properties:

Proton nuclear magnetic resonance
spectrum (δ ppm in CDCl$_3$):
0.87 (3H, d, J=6 Hz),
0.9–2.1 (9H, m),
1.29 (6/3H, t, J=6 Hz),
1.31 (3/3H, t, J=6 Hz),
2.17 (6/3H, d, J=1 Hz),
2.24 (3/3H, d, J=1 Hz),
2.68 (4/3H, q, J=7 Hz),
2.71 (2/3H, t, J=7 Hz),
3.7–3.9 (1H, m), 3.80 (3/3H, s),
3.81 (6/3H, s), 4.1–4.3 (4H, m),
5.98 (1H, d, J=8 Hz),
6.27 (1H, d, J=16 Hz),
6.6–6.8 (2H, m), 6.9–7.1 (2H, m),
7.02 (1H, dd, J=2, 8 Hz),
7.47 (1H, d, J=16 Hz)

EXAMPLE 186

Animation

Using 1.9 g of N-(trans-4-methylcyclohexyl)-4-(2-chloroethoxy)-3-methoxycinnamamide (Example 138), 0.82 g of 4-methylimidazole, 0.5 g of sodium hydride, and 50 ml of THF, a reaction similar to that conducted in Example 180 was carried out. As a result, 1.23 g of white crystal which was about 1:1 mixture of N-(trans-4-methylcyclohexyl) -4-{2-[1-(4-methyl)imidazolyl]ethoxy}-3-methoxycinnamamide (a compound of the present invention ) and N-(trans-4-methylcyclohexyl)-4-{2-[1 -(5-methyl) imidazolyl]ethoxy}-3-methoxycinnamamide (a compound of the present invention) was obtained, which had the following physiochemical properties:

Proton nuclear magnetic resonance
spectrum (δ ppm in CDCl$_3$):
0.86 (3H, d, J=6 Hz),
0.9–2.1 (9H, m),
2.21 (3/2H, d, J=1 Hz),
2.27 (3/2H, d, J=1 Hz),
3.7–3.9 (1H, m), 3.85 (3/2H, s),
3.87 (3/2H, s), 4.1–4.3 (4H, m),
5.45 (1H, d, J=8 Hz),
6.20 (1H, d, J=16 Hz),
6.7–6.8 (2H, m), 6.9–7.1 (2H, m),
7.48 (1/2H, d, J=16 Hz),
7.52 (1/2H, d, J=16 Hz)

EXAMPLE 187

Esterification and Amidation 1.9 g of N-(trans-4-methylcyclohexyl)-4-(2-chloroethoxy )- 3-methoxycinnamamide (Example 138 ) was added to a solution of 0.5 g of sodium hydride in 50 ml of THF. The solution was reacted for 72 hours, while it was refluxed. After reaction, 2 N hydrochloric acid was added to the reaction solution, acidifying the solution, and the solution was extracted with 100 ml of methylene chloride. The organic layer obtained was dried over magnesium sulfate, and the solvent was removed in vacuo. The product obtained was recrystallized from methylene chloride/ether, yielding 0.54 g of N-(trans-4-methylcyclohexyl)-4-vinyloxy-3-methoxycinnamamide (a compound of the present invention ) as white crystal, which had the following physiochemical properties:

Proton nuclear magnetic resonance
spectrum (δ ppm in CDCl$_3$):
0.89 (3H, d, J=6 Hz),
0.9–2.1 (9H, m),
3.7–3.9 (1H, m), 3.89 (3H, s),
4.45 (1H, dd, J=2, 4 Hz),
4.74 (1H, dd, J=2, 12 Hz),
5.35 (1H, d, J=8 Hz),
6.23 (1H, d, J=16 Hz),
6.55 (1H, dd, J=6, 8 Hz),
6.94 (1H, d, J=9 Hz),
7.05 (1H, s), 7.05 (1H, d, J=8 Hz),
7.50 (1H, d, J=16 Hz)
MS [(M+H)+]: 316
HRMS (C$_{19}$H$_{26}$NO$_3$):
Theoretical value: 316.19127.
Measured value: 316. 19027.

EXAMPLE 188

Esterification and Amidation, and Conversion into Non-toxic Salt

A solution of 1.9 of N-(trans-4-methylcyclohexyl)-4-(carboxymethoxy) -3 -methoxycinnamamide (Example 172 ), 1.2 ml of diethyl chlorophosphate and 2.3 ml of triethylamine, mixed in 60 ml of methylene chloride, was stirred for 1 hour at room temperature. Next, 0.6 ml of 4-methylpiperazine and 0.04 g of 4-dimethylaminopyridine were added to the solution under ice-cooling, and the solution was further stirred for 4 hours at room temperature.

After reaction, the reaction solution was washed twice with 200 ml of an aqueous sodium hydrogencarbonate solution. The organic layer obtained was dried over magnesium sulfate, and the solvent was removed in vacuo. The product obtained was refined by means of silica gel column chromatography using methylene chloride only. Thereafter, the solvent was removed in vacuo, yielding 0.45 g of 1-{4-{2-[N-(trans-4-methylcyclohexyl)carbamoyl]vinyl}-2-methoxyphenoxyacetyl}-4-methylpiperazine (a compound of the present invention) as white crystal, which had the following physiochemical properties:

Proton nuclear magnetic resonance
spectrum (δ ppm in CDCl$_3$):
0.89 (3H, d, J=6 Hz),
0.9–2.1 (9H, m),
2.28 (3H, s), 2.3–2.4 (4H, m),
3.6–3.7 (4H, m), 3.7–3.9 (1H, m),
3.88 (3H, s), 4.77 (2H, s),
5.39 (1H, d, J=8 Hz),
6.20 (1H, d, J=16 Hz),
6.89 (1H, d, J=8 Hz), 7.02 (1H, s),
7.02 (1H, d, J=8 Hz),
7.48 (1H, d, J=16 Hz)
MS [(M+H)+]: 429

HRMS (C₂₄H₃₅N₃O₄):
Theoretical value: 429.26276.
Measured value: 429.26326.

The compound described above was reacted in the ordinary method, converting it into 1-{4-{2-[N-(trans-4-methylcyclohexyl) carbamoyl]vinyl}-2-methoxyphenoxyacetyl}-4-methylpiperazine hydrochloride, which had the following physiochemical properties:

Proton nuclear magnetic resonance
spectrum (δ ppm in CD₃OD):
0.91 (3H, d, J=6 Hz),
0.9–2.0 (9H, m),
2.95 (3H, s), 3.0–3.2 (2H, m),
3.4–3.8 (5H, m), 3.90 (3H, s),
4.2–4.4 (1H, m), 4.5–4.7 (1H, m),
4.88 (2H, s)
6.44 (1H, d, J=16 Hz),
6.96 (1H, t, J=8 Hz),
7.00 (1H, dd, J=2, 8 Hz),
7.18 (1H, d, J=2 Hz),
7.41 (1H, d, J=16 Hz)
MS [M⁻]: 465

EXAMPLE 189

Reduction

Using 0.2 g of 1-{4-{2-[N-(trans-4-methylcyclohexyl) carbamoyl]vinyl}-2-methoxyphenoxyacetyl}-4-methylpiperazine (Example 188 ), 0.01 g of 10% palladium-carbon, and 30 ml of methanol, a reaction similar to that conducted in Example 147 was carried out. As a result, 0.13 g of 1-{4-{2-[N-(trans-4-methylcyclohexyl) carbamoyl]ethyl}-2methoxyphenoxyacetyl}-4-methylpiperazine (a compound of the present invention) was obtained as white crystal, which had the following physiochemical properties:

Proton nuclear magnetic resonance
spectrum (δ ppm in CD₃OD):
0.86 (3H, d, J=6 Hz),
0.9–2.0 (3H, s), 2.29 (3H, s), 20 2.3–2.5 (6H, m),
2.34 (2H, t, J=5 Hz),
3.5–3.7 (5H, m),
3.83 (3H, s), 4.69 (2H, s),
5.29 (1H, d, J=8 Hz),
6.66 (1H, dd, J=2, 8 Hz),
6.74 (1H, d, J=2 Hz), 7.02 (1H, s),
7.02 (1H, d, J=8 Hz),
6.83 (1H, d, J=8 Hz)
MS [M⁺]: 431

EXAMPLE 190

Esterification and Amidation, and Conversion into Non-toxic Salt

Using 1.9 g of N-(trans-4-methylcyclohexyl)-4-(carboxymethoxy)-3-methoxycinnamamide (Example 172), 1.2 ml of diethyl chlorophosphate, 2.3 ml of triethylamine, 0.92 g of 4-piperidinopiperidine, 0.04 g of 4-dimethylaminopyridine, and 100 ml of methylene chloride, a reaction similar to that conducted in Example 188 was carried out. As a result, 1.51 g of 1-{4-{2-[N-(trans-4-methylcyclohexyl)carbamoyl]vinyl}-2-methoxyphenoxyacetyl}-4-piperidinopiperidine (a compound of the present invention) was obtained as white crystal, which had the following physiochemical properties:

Proton nuclear magnetic resonance
spectrum (δ ppm in CDCl₃):
0.89 (3H, d, J=6 Hz),
0.9–2.1 (17H, m),
2.3–2.4 (6H, m), 2.9–3.1 (1H, m),
3.7–3.9 (1H, m), 3.88 (3H, s),
4.0–4.2 (1H, m), 4.5–4.7 (1H, m),
4.76 (2H, s), 5.39 (1H, d, J=8 Hz),
6.19 (1H, d, J=16 Hz),
6.88 (1H, d, J=8 Hz),
7.02 (1H, s), 7.02 (1H, d, J=8 Hz),
7.48 (1H, d, J=16 Hz)
MS [(M+H)⁺]: 498
HRMS (C₂₉H₄₄N₃O₄):
Theoretical value: 498.33318.
Measured value: 498.33402.

The compound described above was reacted in the ordinary method, converting it into 1-{4-{2-[N-(trans-4-methylcyclohexyl) carbamoyl]vinyl]-2-methoxyphenoxyacetyl}-4-piperidinopiperidine hydrochloride, which had the following physiochemical properties:

Proton nuclear magnetic resonance
spectrum (δ ppm in D₂O ):
0.91 (3H, d, J=6 Hz),
0.9–2.2 (19H, m),
2.6–2.7 (1H, m), 2.9–3.3 (2H, m),
3.4–3.8 (3H, m), 3.89 (3H, s),
4.1–4.3 (1H, m), 4.4–4.6 (1H, m),
4.8–4.9 (2H, m),
6.44 (1H, d, J=16 Hz),
6.93 (1H, d, J=8 Hz),
7.07 (1H, dd, J=2, 8 Hz),
7.18 (1H, d, J=2 Hz),
7.41 (1H, d, J=16 Hz)
MS [M⁻]: 533

EXAMPLE 191

Reduction

Using 0.2 g of 1-{4-{2-[N-(trans-4methylcyclohexyl)-carbamoyl]vinyl}-2-methoxyphenoxyacetyl}-4-piperidinopiperidine (Example 190), 0.01 g of 10% palladium-carbon, and 30 ml of methanol, a reaction similar to that conducted in Example 147 was carried out. As a result, 0.12 g of 1-{4-{2- [N-(trans-4-methylcyclohexyl) carbamoyl]ethyl}- 2-methoxyphenoxyacetyl}-4-piperidinopiperidine (a compound of the present invention) was obtained as white crystal, which had the following physiochemical properties:

Proton nuclear magnetic resonance
spectrum (δ ppm in CD₃OD):
0.85 (3H, d, J=6 Hz),
0.9–2.0 (19H, m),
2.2–2.3 (1H, m),
2.37 (2H, t, J=7 Hz),
2.5–2.7 (1H, m),
2.85 (2H, t, J=7 Hz),
3.0–3.8 (4H, m), 3.84 (3H, s),
4.2–4.4 (1H, m), 4.6–4.8 (1H, m),
4.66 (2H, d, J=6 Hz),
5.47 (1H, d, J=8 Hz),
6.65 (1H, dd, J=2, 8 Hz),
6.76 (1H, d, J=2 Hz),
6.81 (1H, d, J=8 Hz)
MS [M⁺]: 499

EXAMPLE 192

Esterification and Amidation

A solution of 3.5 g of N-(trans-4-methylcyclohexyl) -4-hydroxy-3-methoxycinnamamide (Example 131), 3.5 ml of diethyl chlorophosphate, and 4 ml of triethylamine, mixed in 60 ml of methylene chloride was stirred for 1 hour at room temperature. Next, 4 g of N-t-butoxycarbonylglycine hydrochloride and 1 g of 4-dimethylaminopiridine were added to the solution under ice-cooling. The solution was further stirred for 4 hours at room temperature.

After reaction, the reaction solution was washed five times with 200 ml of an aqueous sodium hydrogencarbonate solution. The organic layer obtained was dried over magnesium sulfate, and the solvent was removed in vacuo, yielding 3.83 g of N-(trans-4-methylcyclohexyl) -4-(N-t-butoxycarbonylglycyloxy)-3-methoxycinnamamide (a compound of the present invention), which had the following physiochemical properties:

Proton nuclear magnetic resonance spectrum ($\delta$ ppm in $CDCl_3$):
0.92 (3H, d, J=6 Hz),
0.9–1.8 (9H, m),
1.46 (9H, s), 3.1–3.3 (1H, m),
3.84 (3H, s), 4.75 (2H, s),
5.7–5.8 (1H, m),
6.31 (1H, d, J=16 Hz),
7.0–7.2 (3H, m),
7.52 (1H, d, J=16 Hz)
MS [M+]: 446

EXAMPLE 193

Esterification and Amidation, AA and Hydrolysis

Using 5.9 g of 3-acetoxy-4-methoxycinnamic acid derived from isoferulic acid by the acetylation thereof, 4.34 ml of diethyl chlorophosphate, 8.35 ml of triethylamine, 500 ml of methylene chloride, 3.74 g of trans-4-methylcyclohexylammonium chloride, and 0.18 g of 4-dimethylaminopyridine, a reaction similar to that conducted in Example 104 was carried out. As a result, 6.3 g of N-(trans-4-methylcyclohexyl)-3-acetoxy-4-methoxycinnamamide (a compound of the present invention) was obtained as white crystal, which had the following physiochemical properties: Proton nuclear magnetic resonance spectrum ($\delta$ ppm in $CDCl_3$):
0.88 (3H, d, J=6 Hz),
1.0–2.1 (9H, m),
2.31 (3H, s),
3.84 (3H, s), 5.43 (1H, m),
6.17 (1H, d, J=16 Hz),
6.90 (1H, d, J=8 Hz),
7.19 (1H, d, J=2 Hz),
7.28 (1H, dd, J=2, 6 Hz),
7.47 (1H, d, J=16 Hz)
MS [M+]: 331

EXAMPLE 194

Alkylation and Conversion into Non-toxic Salt 2.07 g of potassium carbonate was added to a solution of 4.97 g of N-(trans-4-methylcyclohexyl)-3-acetoxy-4-methoxycinnamamide (Example 193) in 200 ml of ethanol. The solution was stirred for 20 minutes, while it was refluxed. Next, 2.0 ml of ethyl bromoacetate was slowly added dropwise to the solution by means of a dropping funnel. Thereafter, the solution was stirred for 2 hours. After reaction, the solution was allowed to cool to room temperature. The crystal and the potassium carbonate, both precipitated from the reaction solution, were filtered out, and the solvent was removed in vacuo from the filtrate. The product obtained was recrystallized from methylene chloride/ether, yielding 1.46 g of N-(trans-4-methylcyclohexyl)-3-(ethoxycarbonylmethoxy)-4-methoxycinnamamide (a compound of the present invention) as white crystal, which had the following physiochemical properties:

Proton nuclear magnetic resonance spectrum ($\delta$ ppm in $CD_3OD$):
0.90 (3H, d, J=6 Hz),
0.9–2.0 (9H, m),
1.25 (3H, t, J=7 Hz),
3.6–3.8 (1H, m),
3.89 (3H, s), 4.20 (2H, q, J=7 Hz),
4.73 (2H, s),
6.39 (1H, d, J=16 Hz),
6.99 (1H, d, J=8 Hz),
7.13 (1H, d, J=2 Hz),
7.17 (1H, dd, J=2, 8 Hz),
7.38 (1H, d, J=16 Hz)
MS [M+]: 375

Water was added to the crystal and the potassium carbonate, both filtered out. Then, 100 ml of methylene chloride and 100 ml of 2 N hydrochloric acid were added to the solution, which was subjected to extraction. The aqueous layer obtained was again extracted with 100 ml of methylene chloride. The obtained organic layers were combined, washed with an aqueous sodium chloride solution, and dried over magnesium sulfate. Thereafter, the solvent was removed in vacuo.

The product obtained was recrystallized from methylene chloride, yielding 2.58 g of N-(trans-4-methylcyclohexyl) -3-(carboxymethoxy)-4methoxycinnamamide (a compound of the present invention) as white crystal, which had the following physiochemical properties:

Proton nuclear magnetic resonance spectrum ($\delta$ ppm in $CD_3OD$):
0.90 (3H, d, J=6 Hz),
0.9–2.0 (9H, m),
3.6–3.8 (1H, m), 3.87 (3H, s),
4.70 (2H, s),
6.37 (1H, d, J=16 Hz),
6.97 (1H, d, J=8 Hz),
7.01 (1H, d, J=2 Hz),
7.15 (1H, dd, J=2, 8 Hz),
7.38 (1H, d, J=16 Hz)
MS [M+]: 347

The compound described above was reacted in the ordinary method, converting it into N-(trans-4-methylcyclohexyl) -3-(carboxymethoxy)-4-methoxycinnamamide sodium salt, which had the following physiochemical properties:

Proton nuclear magnetic resonance spectrum ($\delta$ ppm in $CD_3OD$):
0.90 (3H, d, J=6 Hz),
0.9–2.0 (9H, m),
3.6–3.8 (1H, m), 3.88 (3H, s),
4.43 (2H, s),
6.39 (1H, d, J=16 Hz),
6.94 (1H, d, J=8 Hz),
7.05 (1H, dd, J=2, 6 Hz),
7.13 (1H, d, J=2 Hz),
7.39 (1H, d, J=16 Hz)
MS [M+]: 369

EXAMPLE 195

Alkylation 1.03 g of potassium carbonate was added to a solution of 2.15 g of N-(cis-4-methylcyclohexyl)-4-hydroxy -3-methoxycinnamamide (Example 105) in 200 ml of ethanol. The solution was stirred for 20 minutes, while it was refluxed. Next, 8.0 ml of ethyl bromoacetate was slowly added dropwise to the solution by means of a dropping funnel. Thereafter, the solution was stirred for 4 hours. After reaction, the potassium carbonate was filtered from the reaction solution, and the solvent was removed in vacuo from the filtrate. The product obtained was recrystallized from methylene chloride/ether, yielding 2.12 g of N-(cis-4-methylcyclohexyl)-4-(ethoxycarbonylmethoxy)-3-methoxycinnamamide (a compound of the present invention) as white crystal, which had the following physiochemical properties:

Proton nuclear magnetic resonance
spectrum (δ ppm in CDCl$_3$):
0.91 (3H, d, J=7 Hz),
0.9–1.8 (9H, m),
1.25 (3H, t, J=7 Hz), 3.91 (3H, s),
4.1–4.3 (1H, m),
4.21 (2H, q, J=7 Hz),
4.70 (2H, s), 5.64 (1H, s),
6.26 (1H, d, J=16 Hz),
6.75 (1H, d, J=9 Hz),
7.00 (1H, dd, J=2, 7 Hz),
7.05 (1H, d, J=2 Hz),
7.50 (1H, d, J=16 Hz),
MS [M+]: 375

EXAMPLE 196

Esterification and Amidation 30 ml of diisopropylethylamine and 1.3 ml of 1-iodopentane were added to a solution of 1.84 g of N-(trans-4-methylcyclohexyl)-4-(carboxymethoxy )-3-methoxycinnamamide (Example 172) in 50 ml of methylene chloride. The solution was stirred for 16 hours, while it was refluxed. After reaction, the reaction solution was washed three times with 200 ml of an aqueous sodium thiosulfate solution and once with an aqueous sodium chloride solution, and was dried over magnesium sulfate. Then, the solvent was removed in vacuo. The product obtained was recrystallized from methylene chloride/ether, yielding 1.56 g of N-(trans-4-methylcyclohexyl)-4-(pentyloxycarbonylmethoxy)-3-methoxycinnamamide (a compound of the present invention) as white crystal, which had the following physiochemical properties:

Proton nuclear magnetic resonance
spectrum (δ ppm in CDCl$_3$):
0.90 (3H, d, J=6 Hz),
0.9–2.6 (13H, m),
0.98 (3H, s), 3.7–3.9 (1H, m),
3.89 (3H, s), 4.08 (2H, t, J=7 Hz),
4.72 (2H, s), 5.44 (1H, d, J=8 Hz),
6.22 (1H, d, J=16 Hz),
6.74 (1H, d, J=8 Hz),
7.00 (1H, dd, J=2, 7 Hz),
7.04 (1H, d, J=2 Hz),
7.49 (1H, d, J=16 Hz),
MS [M+]: 417

EXAMPLE 197

Esterification and Amidation 30 ml of diisopropylethylamine and 1.0 ml of iodomethane were added to a solution of 1.84 g of N-(trans-4-methylcyclohexyl)-4-(carboxymethoxy)-3-methoxycinnamamide (Example 172) in 50 ml methylene chloride. The solution was stirred for 16 hours, while it was refluxed. After reaction, the reaction solution was washed three times with 200 ml of an aqueous sodium thiosulfate solution and once with an aqueous sodium chloride solution, and was dried over magnesium sulfate. Then, the solvent was removed in vacuo. The product obtained was recrystallized from methylene chloride/ether, yielding 1.38 g of N-(trans-4-methylcyclohexyl)4-(methoxycarbonylmethoxy)-3-methoxycinnamamide (a compound of the present invention) as white crystal, which had the following physiochemical properties:

Proton nuclear magnetic resonance
spectrum (δ ppm in CDCl$_3$):
0.90 (3H, d, J=6 Hz),
0.9–2.1 (9H, m),
3.6–3.8 (1H, m), 3.73 (3H, s),
3.89 (3H, s), 4.70 (2H, s),
5.41 (1H, d, J=8 Hz),
6.23 (1H, d, J=16 Hz),
6.76 (1H, d, J=8 Hz),
7.01 (1H, dd, J=2, 7 Hz),
7.05 (1H, d, J=2 Hz),
7.50 (1H, d, J=16 Hz),
MS [M+]: 361

EXAMPLE 198

Halogenation 19.5 g of sodium iodide was added to a solution of 4.57 g of N-(trans-4-methylcyclohexyl)-4-(2-chloroethoxy)-3-methoxycinnamamide (Example 138) in 300 ml of methylethylketone. The solution was stirred for 19 hours, while it was refluxed. After reaction, the reaction solution was washed three times with 200 ml of an aqueous sodium thiosulfate solution and once with an aqueous sodium chloride solution, and was dried over magnesium sulfate. Then, the solvent was removed in vacuo. The product obtained was recrystallized from methylene chloride/ether, yielding 4.86 g of N-(trans-4-methylcyclohexyl)-4-(2-iodoethoxy)-3-methoxycinnamamide (a compound of the present invention) as white crystal, which had the following physiochemical properties:

Proton nuclear magnetic resonance
spectrum (δ ppm in CDCl$_3$):
0.89 (3H, d, J=6 Hz),
0.9–2.1 (9H, m),
3.42 (2H, t, J=7 Hz),
3.8–3.9 (1H, m),
3.89 (3H, s), 4.28 (2H, t, J=7 Hz),
5.46 (1H, d, J=8 Hz),
6.21 (1H, d, J=16 Hz),
6.80 (1H, d, J=8 Hz), 7.03 (1H, s),
7.04 (1H, dd, J=2, 7 Hz),
7.49 (1H, d, J=16 Hz),
MS [M+]: 443

EXAMPLE 199

| (i) | Corn starch | 44 g |
|---|---|---|
| (ii) | Crystalline cellulose | 40 g |
| (iii) | Carboxymethylcellulose calcium | 5 g |
| (iv) | Light anhydrous silicic acid | 0.5 g |
| (v) | Magnesium stearate | 0.5 g |
| (vi) | Compound obtained in Example 68 | 10 g |
| Total | | 100 g |

According to the formulation specified above, the components (i) to (vi) were mixed uniformly. The mixture was compressed and molded by a pelletizer into tablets weighing 200 mg each. Each tablet contains 10 mg of the compound obtained in Example 68. These tablets are to be administered to an adult a few times a day, 5 to 15 tablets each time.

EXAMPLE 200

| (i) | Crystalline cellulose | 84.5 g |
|---|---|---|
| (ii) | Magnesium stearate | 0.5 g |
| (iii) | Carboxymethylcellulose calcium | 5 g |
| (iv) | Compound obtained in Example 81 | 10 g |
| Total | | 100 g |

According to the formulation specified above, the components (i) and (iv), and a part of the component (ii) were mixed uniformly. The mixture was compressed and molded, and the molding formed was pulverized. The component (iii) and the remaining part of the component (ii) were added to the pulverized material, and mixed. The mixture was compressed and molded by the pelletizer into tablets weighing 200 mg each. Each tablet contains 10 mg of the compound obtained in Example 68. These tablets are to be administered to an adult several times a day, 5 to 15 tablets each time.

EXAMPLE 201

| (i) | Crystalline cellulose | 49.5 g |
|---|---|---|
| (ii) | 10% ethanol solution of hydroxypropylcellulose | 35 g |
| (iii) | Carboxymethylcellulose calcium | 5 g |
| (iv) | Magnesium stearate | 0.5 g |
| (v) | Compound obtained in Example 94 | 10 g |
| Total | | 100 g |

According to the formulation specified above, the components (i), (ii) and (v) were mixed uniformly. The mixture was kneaded and granulated by a granulator, dried and crushed. Thereafter, the components (iii) and (iv) were mixed with the crushed material. The resultant mixture was compressed and molded by the pelletizer into tablets weighing 200 mg each. Each tablet contains 20 mg of the compound obtained in Example 94. These tablets are to be administered to an adult several times a day, 5 to 15 tablets each time.

EXAMPLE 202

| (i) | Corn starch | 34.5 g |
|---|---|---|
| (ii) | Magnesium stearate | 50 g |
| (iii) | Carboxymethylcellulose calcium | 5 g |
| (iv) | Light anhydrous silicic acid | 0.5 g |
| (v) | Compound obtained in Example 97 | 10 g |
| Total | | 100 g |

According to the formulation specified above, the components (i)–(v) were mixed uniformly. The mixture was compressed and molded by a compression molder. The molding obtained was pulverized by a pulverizer and sieved, forming granules. Each gram of the granules contains 100 mg of the compound obtained in Example 97. The granules are to be administered to an adult in an amount of 1 to 3 g each day, in several portions.

EXAMPLE 203

| (i) | Crystalline cellulose | 55 g |
|---|---|---|
| (ii) | 10% methanol solution of hydroxypropylcellulose | 35 g |

-continued

| (iii) | Compound obtained in Example 105 | 10 g |
|---|---|---|
| Total | | 100 g |

According to the formulation specified above, the components (i)–(iii) were mixed uniformly. The mixture was kneaded and granulated by an extruding granulater, dried and sieved, obtaining granules. Each gram of the granules contains 100 mg of the compound obtained in Example 105. The granules are to be administered to an adult in an amount of 1 to 3 g each day, in several portions.

EXAMPLE 204

| (i) | Corn starch | 89.5 g |
|---|---|---|
| (ii) | Light anhydrous silicic acid | 0.5 g |
| (iii) | Compound obtained in Example 114 | 10 g |
| Total | | 100 g |

According to the formulation specified above, the components (i)–(iii) were mixed uniformly. The mixture was filled in No. 2 capsules, in an amount of 200 mg in each capsule, thereby preparing drug capsules. Each capsule contains 10 mg of the compound obtained in Example 114. The capsules are to be administered to an adult several times a day, 5 to 15 capsules each time.

EXAMPLE 205

| (i) | Soybean oil | 5 g |
|---|---|---|
| (ii) | Distilled water for injection | 89.5 g |
| (iii) | Soybean phospholipid | 2.5 g |
| (iv) | Glycerin | 2 g |
| (v) | Compound obtained in Example 131 | 1 g |
| Total | | 100 g |

According to the formulation specified above, the component (v) is dissolved in the components (i) and (iii). To the resultant solution, a solution of the components (ii) and (iv) was added, and emulsified, thereby obtaining an injection.

We claim:

1. A compound represented by formula (I) shown below or a pharmaceutically acceptable salt thereof:

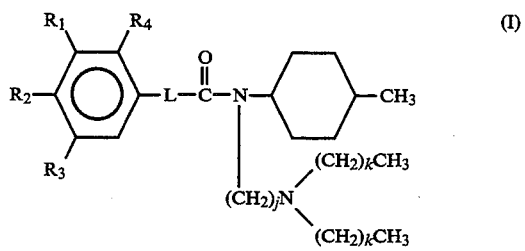

where L represents —(CH=CH)$_k$— or —(CH$_2$)k—; j represents an integer of 1 to 6; k represents an integer of 0 to 5; and R$_1$, R$_2$, R$_3$ and R$_4$ are either identical or different, and each represents a hydrogen atom, an amino group, an acylamino group, a dialkylamino group in which each alkyl moiety has 1 to 5 carbon atoms, a halogen atom, a hydroxyl group, an acetoxy group, an alkoxy group having 1 to 3 carbon atoms, a trifluoromethyl group, a nitro group, tetrahydropyranyloxy group, or a benzyloxy group.

2. A compound represented by formula II shown below, or a pharmaceutically acceptable salt thereof:

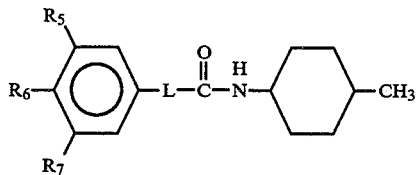

(II)

where L represents —(CH═CH)$_k$— or —(CH$_2$)k—; each k represents an integer of 1 to 5; R$_5$, R$_6$ and R$_7$ are either identical or different, and each represents a hydrogen atom, a hydroxyl group, an acetoxy group, an amino acid ester group in which the amino moiety may be protected by a protective group, an alkoxy group having 1 to 3 carbon atoms, or —O—(CH$_2$)j—Y$_1$; j represents an integer of 1 to 6; and Y1 is a halogen atom, an amino group, an amino group substituted with 1 or 2 thioethanol groups, an amino group substituted with 1 or 2 allyl groups, a monoalkylamino group having 1 to 10 carbon atoms, a dialylamino group in which each alkyl moiety has 1 to 10 carbon atoms, an imidazole group substituted with 1 to 3 substituent groups, a benzimidazole group substituted with 1 to 3 substituent groups, a diazole group, a triazole group, a tetrazole group, a piperidine group, a piperidinopiperidine group, an isonipecotic acid group or an ester thereof with an alkyl group having 1 to 5 carbon atoms, a thiazolidine group, a pyrrolidine group, a morpholine group, a 4-methylpiperazine group, a carboxyl group, a carboxylic acid alkylester group in which the alkyl moiety has 1 to 5 carbon atoms or a carboxamide group.

3. The compound or pharmaceutically acceptable salt according to claim 2, wherein L in formula (II) is —(CH$_2$)$_k$— where k is an integer of 1 to 4.

4. The compound or a pharmaceutically acceptable salt according to claim 2, wherein L in formula (II) is —(CH═CH)$_k$— where k is an integer of 1 to 4.

5. A VI-type allergy suppressive drug containing, as an effective component, a compound represented by formula (I) or a pharmaceutical, acceptable salt thereof:

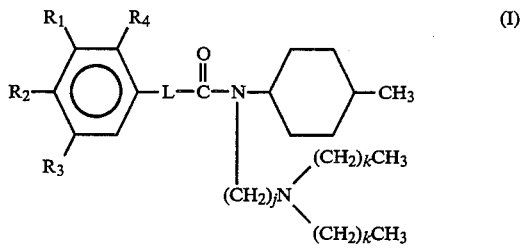

(I)

where L represents —(CH═CH)$_k$— or —(CH$_2$)$_k$—; j represents an integer of 1 to 6; k represents an integer of 0 to 5; and R$_1$, R$_2$, R$_3$ and R$_4$ are either identical or different, and each represents a hydrogen atom, an amino group, an acylamino group, a dialkylamino group in which each alkyl moiety has 1 to 5 carbon atoms, a halogen atom, a hydroxyl group, an acefoxy group, an alkoxy group having 1 to 3 carbon atoms, a trifluoromethyl group, a nitro group, tetrahydropyranyloxy group, or a benzyloxy group;

6. A IV-type allergy suppressive drug containing, a IV-type allergy suppressive amount of a compound represented by formula (II) or a pharmaceutical acceptable salt thereof:

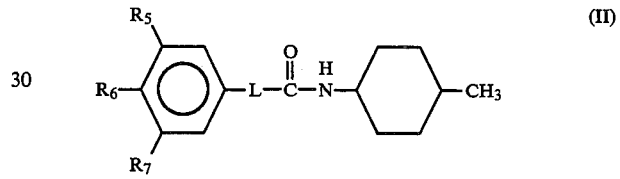

(II)

where L represents —(CH═CH)$_k$— or —(CH$_2$)$_k$—; each k represents an integer of 0 to 5; identical or different, and each represents a hydrogen atom, a hydroxyl group, an acetoxy group, an amino acid ester group in which the amino moiety may be protected by a protective group, an alkoxy group having 1 to 3 carbon atoms, or —O—(CH$_2$)$_j$—Y$_1$; j represents an integer of 1 to 6; and Y1 is a halogen atom, an amino group, an amino group substituted with 1 or 2 thioethanol groups, an amino group substituted with 1 or 2 allyl groups, a monoalkylamino group having 1 to 10 carbon atoms, a dialylamino group in which each alkyl moiety has 1 to 10 carbon atoms, an imidazole group substituted with 1 to 3 substituent groups, a benzimidazole group substituted with 1 to 3 substituent groups, a diazole group, a triazole group, a tetrazole group, a piperidine group, a piperidinopiperidine group, an isonipecotic acid group or an ester thereof with an alkyl group having 1 to 5 carbon atoms, a thiazolidine group, a pyrrolidine group, a morpholine group, a 4-methylpiperazine group, a carboxyl group, a carboxylic acid alkylester group in which the alkyl moiety has 1 to 5 carbon atoms or a carboxamide group.

7. The drug according to claim 6, which further comprises a pharmaceutically acceptable carrier.

* * * * *